(12) United States Patent
Jung et al.

(10) Patent No.: US 11,746,117 B2
(45) Date of Patent: Sep. 5, 2023

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Wanpyo Hong, Daejeon (KR); Sang Duk Suh, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG Chem, LTD., Seoul (KR)

( * ) Notice: Subject to any disclaimer, the term of this patent is extended or adjusted under 35 U.S.C. 154(b) by 324 days.

(21) Appl. No.: 17/275,664

(22) PCT Filed: Nov. 14, 2019

(86) PCT No.: PCT/KR2019/015558
§ 371 (c)(1),
(2) Date: Mar. 11, 2021

(87) PCT Pub. No.: WO2020/111602
PCT Pub. Date: Jun. 4, 2020

(65) Prior Publication Data
US 2022/0056047 A1 Feb. 24, 2022

(30) Foreign Application Priority Data

Nov. 27, 2018 (KR) ......................... 10-2018-0148563
Nov. 13, 2019 (KR) ......................... 10-2019-0145261

(51) Int. Cl.
*C07D 519/00* (2006.01)
*C07D 209/82* (2006.01)
(Continued)

(52) U.S. Cl.
CPC ......... *C07D 519/00* (2013.01); *H10K 85/654* (2023.02); *H10K 85/6572* (2023.02);
(Continued)

(58) Field of Classification Search
CPC .. C07D 519/00; C07D 209/82; C07D 251/24; C07D 403/14; C07D 491/048; H10K 85/654; H10K 85/657; H10K 8/6572
See application file for complete search history.

(56) References Cited

U.S. PATENT DOCUMENTS 9,577,199 B2 2/2017 Lecloux et al.
2004/0251816 A1 12/2004 Leo et al.
(Continued)

FOREIGN PATENT DOCUMENTS

CN 101087776 A 12/2007
CN 100366703 C 2/2008
(Continued)

OTHER PUBLICATIONS

U.S. Appl. No. 17/278,406.
(Continued)

*Primary Examiner* — Vu A Nguyen
(74) *Attorney, Agent, or Firm* — Bryan Cave Leighton Paisner LLP

(57) ABSTRACT

A heterocyclic compound represented by Chemical Formula 1 or 2, and an organic light emitting device including the same, and the heterocyclic compound which is used as a material of an organic material layer of the organic light emitting device and provides improved efficiency, low driving voltage, and improved lifetime characteristics of the organic light emitting device.

(Continued)

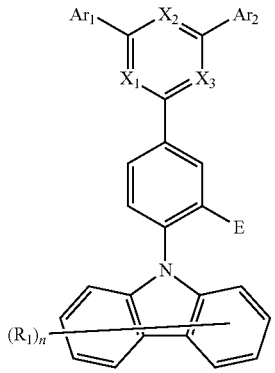

[Chemical Formula 1]

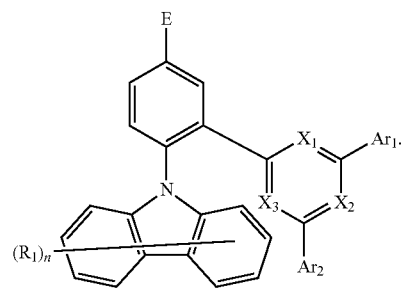

[Chemical Formula 2]

9 Claims, 1 Drawing Sheet

(51) Int. Cl.
  *C07D 251/24* (2006.01)
  *C07D 403/14* (2006.01)
  *H01L 51/00* (2006.01)
  *H01L 51/50* (2006.01)
  *H10K 85/60* (2023.01)
  *H10K 50/11* (2023.01)
  *H10K 101/30* (2023.01)
  *H10K 101/40* (2023.01)

(52) U.S. Cl.
  CPC ......... *H10K 85/6574* (2023.02); *H10K 50/11* (2023.02); *H10K 2101/30* (2023.02); *H10K 2101/40* (2023.02)

(56) References Cited

U.S. PATENT DOCUMENTS

| | | | |
|---|---|---|---|
| 2009/0191426 | A2 | 7/2009 | Yabe et al. |
| 2012/0126221 | A1 | 5/2012 | Kitamura et al. |
| 2012/0126692 | A1 | 5/2012 | Ise et al. |
| 2012/0205640 | A1 | 8/2012 | Kai et al. |
| 2013/0292654 | A1 | 11/2013 | Matsunaga et al. |
| 2014/0114069 | A1 | 4/2014 | Kim et al. |
| 2015/0218191 | A1 | 8/2015 | Sannomiya et al. |
| 2015/0380662 | A1 | 12/2015 | Kim et al. |
| 2016/0329502 | A1 | 11/2016 | Dyatkin et al. |
| 2017/0047522 | A1 | 2/2017 | Noda et al. |
| 2017/0117488 | A1 | 4/2017 | Ahn et al. |
| 2017/0244043 | A1 | 8/2017 | Kim et al. |
| 2018/0123049 | A1 | 5/2018 | Lee et al. |
| 2018/0145262 | A1 | 5/2018 | Zeng et al. |
| 2018/0170914 | A1 | 6/2018 | Miyata et al. |
| 2018/0248127 | A1 | 8/2018 | Lee et al. |
| 2019/0019960 | A1 * | 1/2019 | Zink .................... C07D 405/14 |
| 2019/0237680 | A1 | 8/2019 | Kim et al. |
| 2020/0115364 | A1 | 4/2020 | Aguilera-Iparraguirre et al. |
| 2020/0331898 | A1 | 10/2020 | Seifermann |
| 2022/0271233 | A1 | 8/2022 | Yoon et al. |

FOREIGN PATENT DOCUMENTS

| | | |
|---|---|---|
| CN | 103764786 | 4/2014 |
| CN | 107667102 | 2/2018 |
| CN | 107880028 | 4/2018 |
| CN | 107935914 | 4/2018 |
| CN | 107987009 | 5/2018 |
| CN | 109251199 A | 1/2019 |
| CN | 112533900 A | 3/2021 |
| DE | 102016112377 | 1/2018 |
| JP | 2009-155300 A | 7/2009 |
| JP | 2009-158848 A | 7/2009 |
| JP | 2010-030937 A | 2/2010 |
| JP | 4474493 B1 | 6/2010 |
| JP | 4590020 B1 | 12/2010 |
| JP | 4729642 B1 | 7/2011 |
| JP | 2014-141571 | 8/2014 |
| JP | 2018-035129 A | 3/2018 |
| KR | 10-2000-0051826 A | 8/2000 |
| KR | 10-2010-0131939 | 12/2010 |
| KR | 10-2012-0018231 | 2/2012 |
| KR | 10-2012-0033711 | 4/2012 |
| KR | 10-2012-0098694 | 9/2012 |
| KR | 10-2012-0109744 A | 10/2012 |
| KR | 10-2013-0020398 A | 2/2013 |
| KR | 10-2013-0130236 A | 12/2013 |
| KR | 10-2014-0014959 | 2/2014 |
| KR | 10-2014-0015240 | 2/2014 |
| KR | 10-1396171 | 5/2014 |
| KR | 10-2014-0139307 A | 12/2014 |
| KR | 10-2015-0061174 A | 6/2015 |
| KR | 10-2015-0063462 | 6/2015 |
| KR | 10-2015-0105201 A | 9/2015 |
| KR | 10-2015-0129282 A | 11/2015 |
| KR | 10-2015-0139459 A | 12/2015 |
| KR | 10-2016-0003362 A | 1/2016 |
| KR | 10-2016-0041768 | 4/2016 |
| KR | 10-2016-0066339 | 6/2016 |
| KR | 10-2016-0129190 A | 11/2016 |
| KR | 10-2017-0049291 | 5/2017 |
| KR | 10-2017-0060836 A | 6/2017 |
| KR | 10-2017-0076292 A | 7/2017 |
| KR | 10-2017-0079348 | 7/2017 |
| KR | 10-2017-0097820 A | 8/2017 |
| KR | 10-2017-0113808 A | 10/2017 |
| KR | 10-2017-0116993 A | 10/2017 |
| KR | 10-2018-0027468 A | 3/2018 |
| KR | 107954922 | 4/2018 |
| KR | 10-2018-0047306 A | 5/2018 |
| KR | 10-2018-0063708 | 6/2018 |
| KR | 10-2018-0065276 | 6/2018 |
| KR | 10-2018-0092035 | 8/2018 |
| KR | 10-2018-0098809 | 9/2018 |
| KR | 10-2018-0109747 A | 10/2018 |
| KR | 10-1926771 | 12/2018 |
| KR | 10-2019-0008129 | 1/2019 |
| KR | 10-2019-0108094 | 9/2019 |
| KR | 10-2020-0047418 | 5/2020 |
| KR | 10-2020-0063053 | 6/2020 |
| TW | 2019-12640 | 4/2019 |
| WO | 2003/012890 A2 | 2/2003 |
| WO | 2003-012890 A3 | 8/2003 |
| WO | 2012-005362 | 1/2012 |
| WO | 2013/027906 A1 | 2/2013 |
| WO | 2016-089080 | 6/2016 |
| WO | 2016/181846 A1 | 11/2016 |
| WO | 2017-190885 | 11/2017 |
| WO | 2018/147638 A1 | 8/2018 |
| WO | 2018/237385 A1 | 12/2018 |
| WO | 2019-076844 | 4/2019 |
| WO | WO-2019076844 A1 * | 4/2019 ............. C09K 11/06 |

(56) References Cited

FOREIGN PATENT DOCUMENTS

WO    2019/086297 A1    5/2019
WO    WO-2019121112 A1 *   6/2019   ........... C07D 405/14

OTHER PUBLICATIONS

U.S. Appl. No. 17/278,757.
U.S. Appl. No. 17/281,335.
U.S. Appl. No. 17/282,071.
Lee, D. R. et al., "Bis(diphenyltriazine) as a new acceptor of efficient thermally activated delayed flourescent emitters," Dyes and Pigments (2018), doi: 10.1016/j.dyepig.2017.12.048, 32 pages.
Park, H. et al., "A directly coupled dual emitting core based molecular design of thermally activated delayed fluorescent emitters," J. Mater. Chem. C., 5:12143-12150 (2017).
Chan Seok Oh et al., "Dihedral Angle Control of Blue Thermally Activated Delayed Fluorescent Emitters through Donor Substitution Position for Efficient Reverse Intersystem Crossing", ACS Appl. Mater. Interfaces 10: 35420-35429 (2018).

* cited by examiner

[FIG. 1]
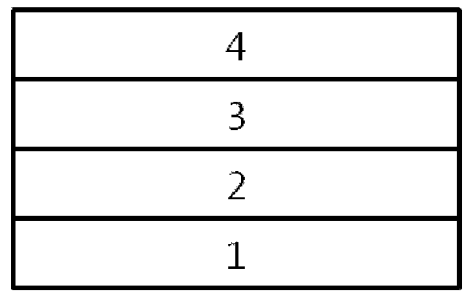
[FIG. 2]
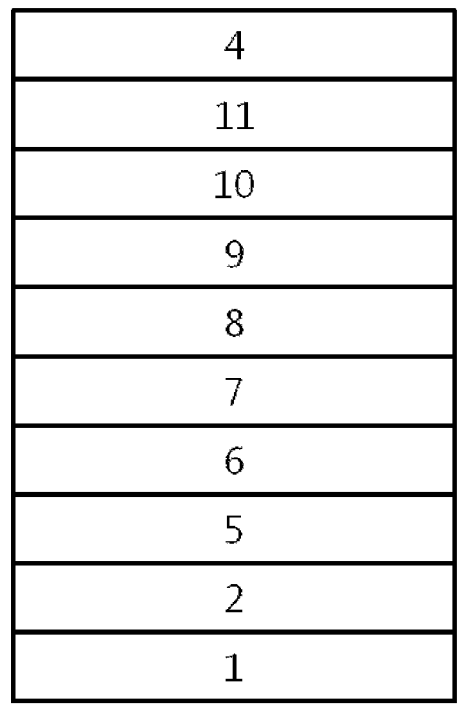

HETEROCYCLIC COMPOUND AND ORGANIC LIGHT EMITTING DEVICE COMPRISING SAME

CROSS-REFERENCE TO RELATED APPLICATION(S)

This application is a National Stage Application of International Application No. PCT/KR2019/015558 filed on Nov. 14, 2019, which claims priority to Korean Patent Application No. 10-2018-0148563 filed on Nov. 27, 2018, and Korean Patent Application No. 10-2019-0145261 filed on Nov. 13, 2019, disclosures of which are incorporated herein by reference in their entirety.

TECHNICAL FIELD

The present disclosure relates to a novel compound and an organic light emitting device including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

RELATED ARTS

Patent Literature 1: Korean Patent Laid-open Publication No. 10-2000-0051826

DETAILED DESCRIPTION

Technical Problem

It is an object of the present disclosure to provide a novel organic light emitting material and an organic light emitting device including the same.

Technical Solution

One aspect of the present disclosure provides a compound represented by the following Chemical Formula 1 or 2:

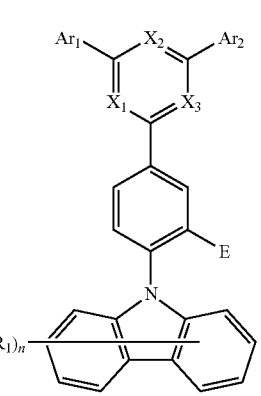

[Chemical Formula 1]

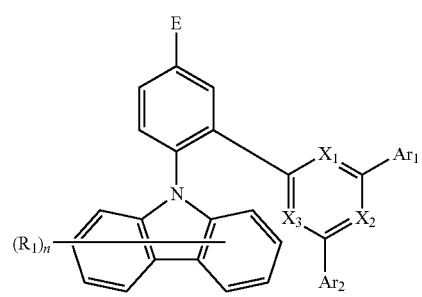

[Chemical Formula 2]

wherein, in Chemical Formulas 1 and 2, $X_1$ to $X_3$ are each independently, CH or N, and at least one of $X_1$ to $X_3$ is N, $Ar_1$ and $Ar_2$ are each independently a substituted or unsubstituted $C_{6-60}$ aryl; or a substituted or unsubstituted $C_{2-60}$ heteroaryl containing at least one heteroatom selected from the group consisting of N, O, and S, $R_1$ is each independently deuterium; a substituted or unsubstituted $C_{6-60}$ aryl; or a substituted or unsubstituted $C_{2-60}$ heteroaryl containing at least one heteroatom selected from the group consisting of N, O, and S, n is an integer of 0 to 8, E is a substituent represented by the following Chemical Formula 3-1 or 3-2,

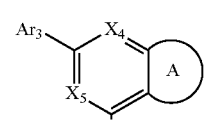

[Chemical Formula 3-1]

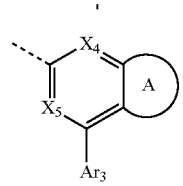

[Chemical Formula 3-2]

wherein, in Chemical Formulas 3-1 and 3-2, $X_4$ and $X_5$ are each independently, CH or N, and at least one of $X_4$ and $X_5$ is N, $Ar_3$ is a substituted or unsubstituted $C_{6-60}$ aryl; or a substituted or unsubstituted $C_{2-60}$ heteroaryl containing at least one heteroatom selected from the group consisting of N, O, and S, wherein A is represented by the following Chemical Formula 4-1 or 4-2,

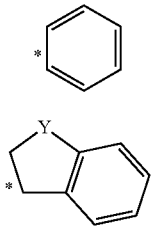

[Chemical Formula 4-1]

[Chemical Formula 4-2]

wherein, in Chemical Formulas 4-1 and 4-2,

\* Is a bond shared with an adjacent hexagonal ring,

Y is O, S, C(R')$_2$, or NR',

R' is each independently hydrogen; deuterium; a substituted or unsubstituted C$_{6-60}$ aryl; or a substituted or unsubstituted C$_{2-60}$ heteroaryl containing at least one heteroatom selected from the group consisting of N, O, and S.

In another aspect of the present disclosure, an organic light emitting device is provided, including a first electrode; a second electrode provided to face the first electrode; and one or more organic material layers provided between the first electrode and the second electrode, wherein one or more layers of the organic material layers include the compound represented by Chemical Formula 1 or 2.

Advantageous Effects

The compound represented by Chemical Formula 1 or 2 described above can be used as a material of an organic material layer of an organic light emitting device and may improve the efficiency and achieve a low driving voltage and/or improve lifetime characteristics in the organic light emitting device. In particular, the compound represented by Chemical Formula 1 or 2 may be used as a hole injection material, a hole transport material, a hole injection and transport material, a light emitting material, an electron transport material, or an electron injection material.

BRIEF DESCRIPTION OF DRAWINGS

FIG. 1 depicts an example of an organic light emitting device including a substrate 1, an anode 2, a organic material layer 3, and a cathode 4.

FIG. 2 depicts an example of an organic light emitting device including a substrate 1, an anode 2, a hole injection layer 5, a hole transport layer 6, an electron blocking layer 7, a light emitting layer 8, a hole blocking layer 9, an electron transport layer 10, an electron injection layer 11, and a cathode 4.

DETAILED DESCRIPTION

Hereinafter, the present disclosure is described in more detail to help understanding of the present disclosure.

One embodiment of the disclosure provides a compound represented by Chemical Formula 1 or 2.

In the present specification, the notation

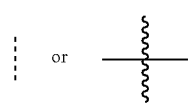

or means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification the number of carbon atoms in a carbonyl group is not particularly limited, but is preferably 1 to 40 carbon atoms. Specifically, the carbonyl group may be compounds having the following structures, but is not limited thereto.

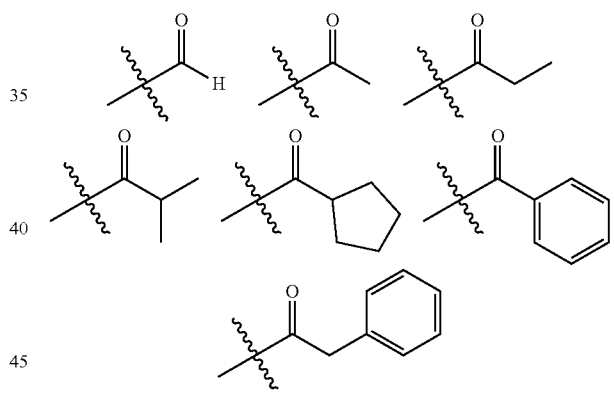

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

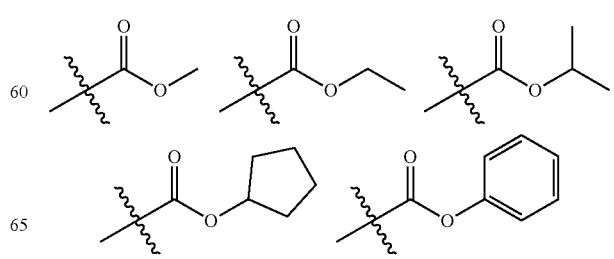

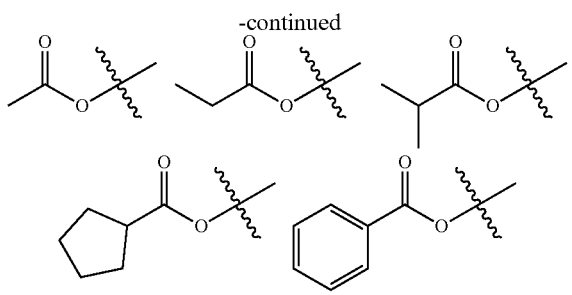

In the present specification, the number of carbon atoms in an imide group is not particularly limited, but is preferably 1 to 25. Specifically, the imide group may be compounds having the following structures, but is not limited thereto.

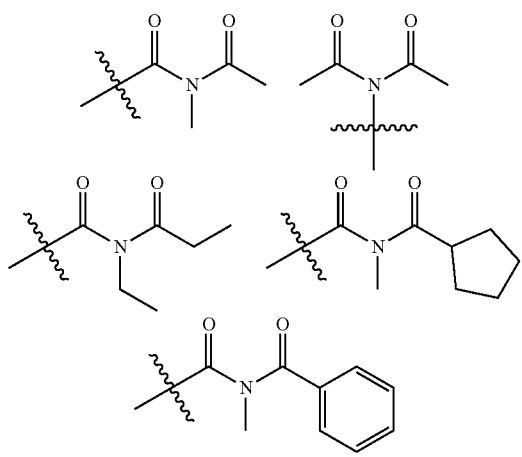

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl- propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to still another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a spiro structure. In the case where the fluorenyl group is substituted,

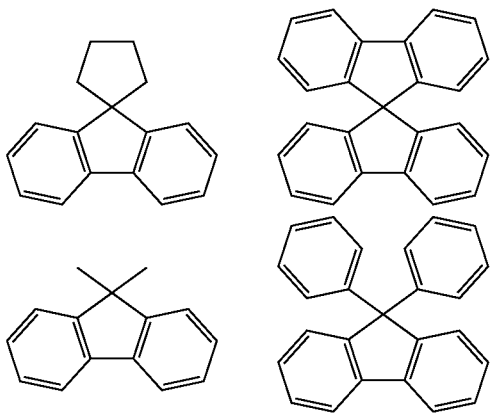

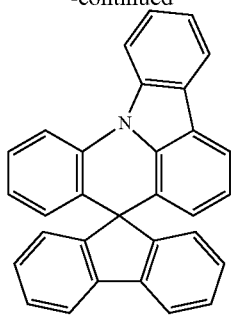

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an thiazolyl group, an isoxazolyl group, an oxadiazolyl group, an thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Preferably, $R_1$ may be each independently deuterium; a substituted or unsubstituted $C_{6-20}$ aryl; or a substituted or unsubstituted $C_{2-20}$ heteroaryl containing one or more heteroatoms selected from the group consisting of N, O, and S, and more preferably, each $R_1$ may be independently, a hydrogen or phenyl.

Preferably, n may be an integer of 0 to 2.

$X_1$ to $X_3$ are each independently, CH or N, and at least one of $X_1$ to $X_3$ is N. Preferably at least two of $X_1$ to $X_3$ may be N, or all of $X_1$ to $X_3$ may be N.

For example, E may be any one selected from the group consisting of the following:

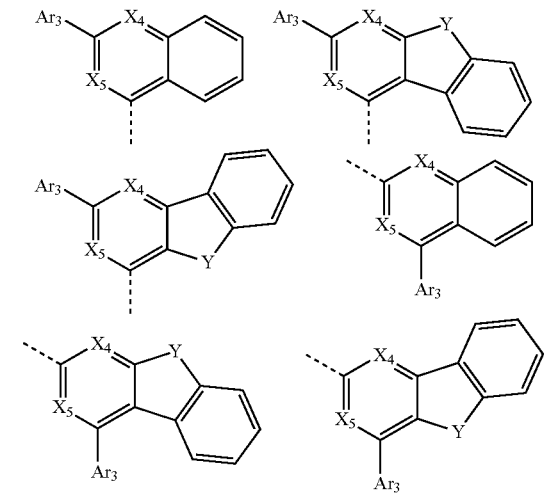

wherein, $Ar_3$, $X_4$, $X_5$, and Y are the same as those defined in Chemical Formulas 3-1 and 3-2.

$X_4$ and $X_5$ are each independently, CH or N, and at least one of $X_4$ and $X_5$ is N. Preferably both $X_4$ and $X_5$ may be N.

Preferably, Y may be O or S.

Preferably, $Ar_1$ to $Ar_3$ are each independently a substituted or unsubstituted $C_{6-20}$ aryl; or a substituted or unsubstituted $C_{2-20}$ heteroaryl containing one or more heteroatoms selected from the group consisting of N, O, and S. More preferably, $Ar_1$ to $Ar_3$ may be each independently, phenyl, biphenyl, phenyl substituted with five deuteriums, or dibenzofuranyl.

More preferably, $Ar_1$ and $Ar_2$ may be each independently phenyl or phenyl substituted with five deuteriums.

Representative examples of the compound represented by Chemical Formula 1 or 2 are as follows:

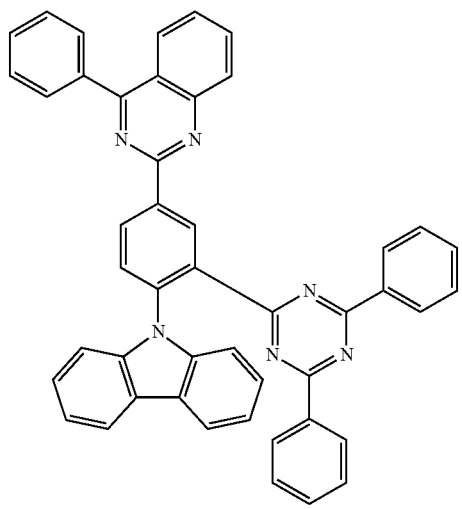

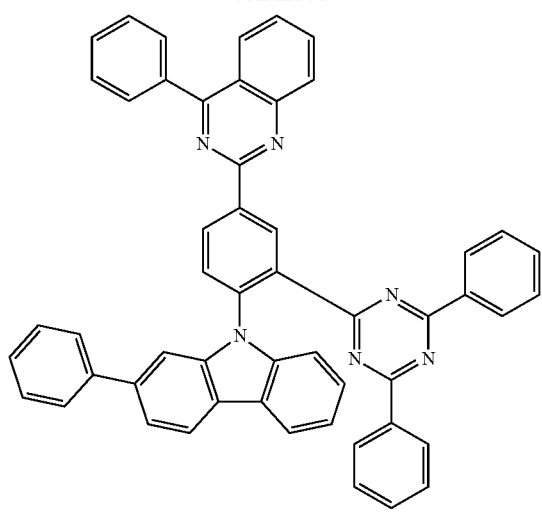
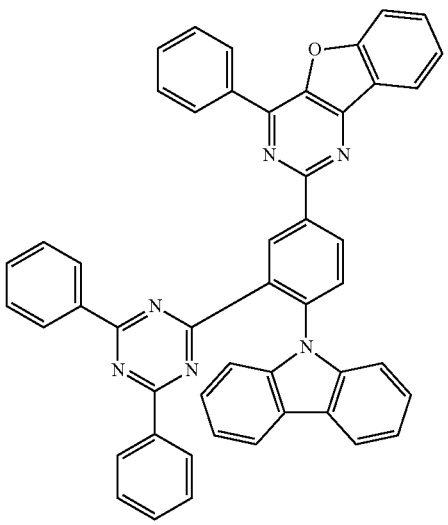
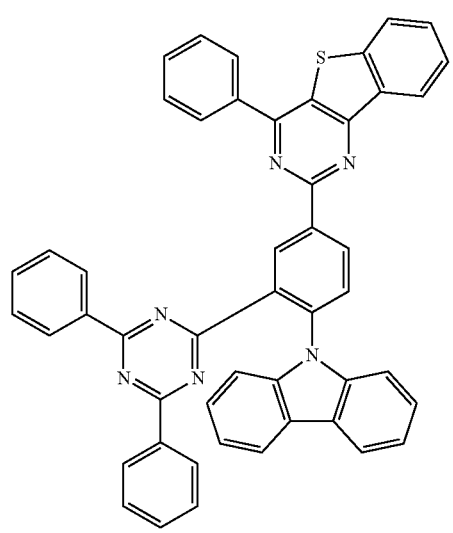
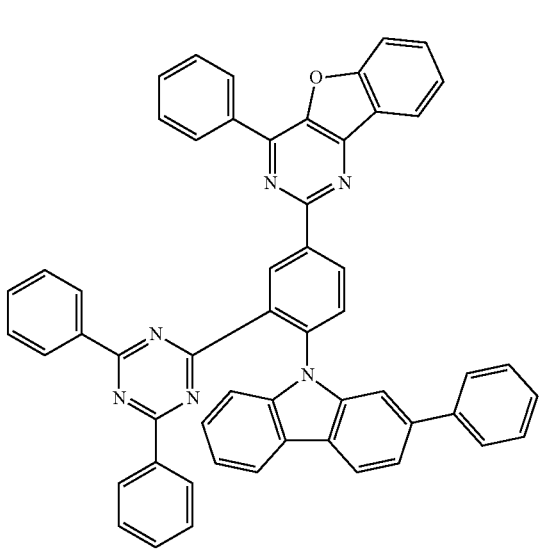
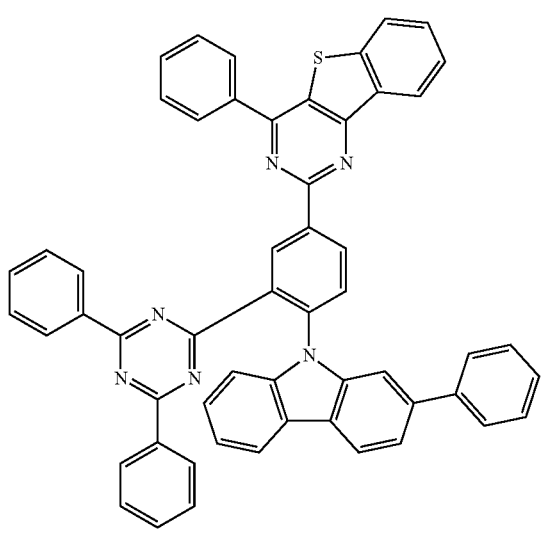
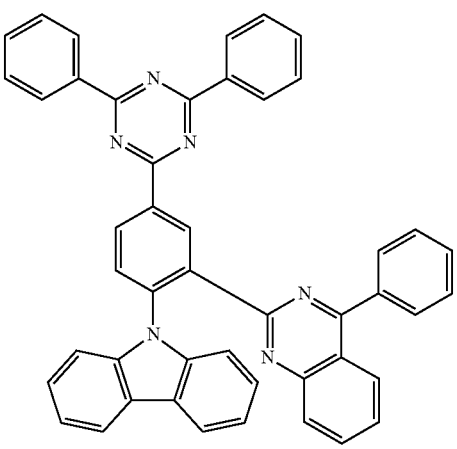

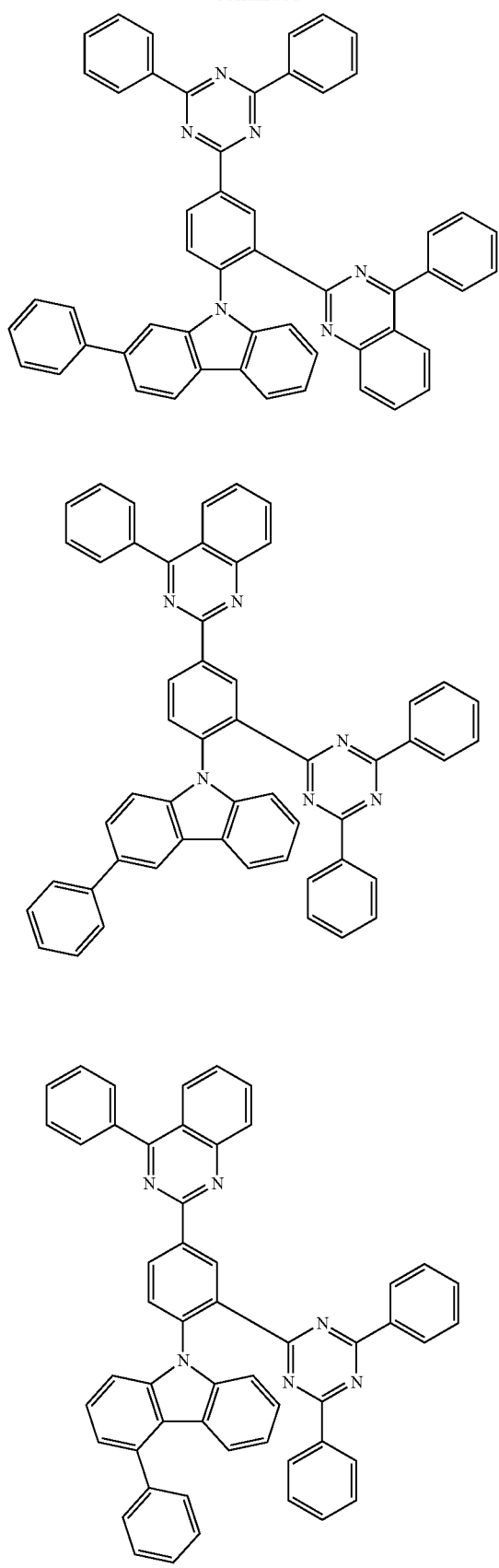

-continued
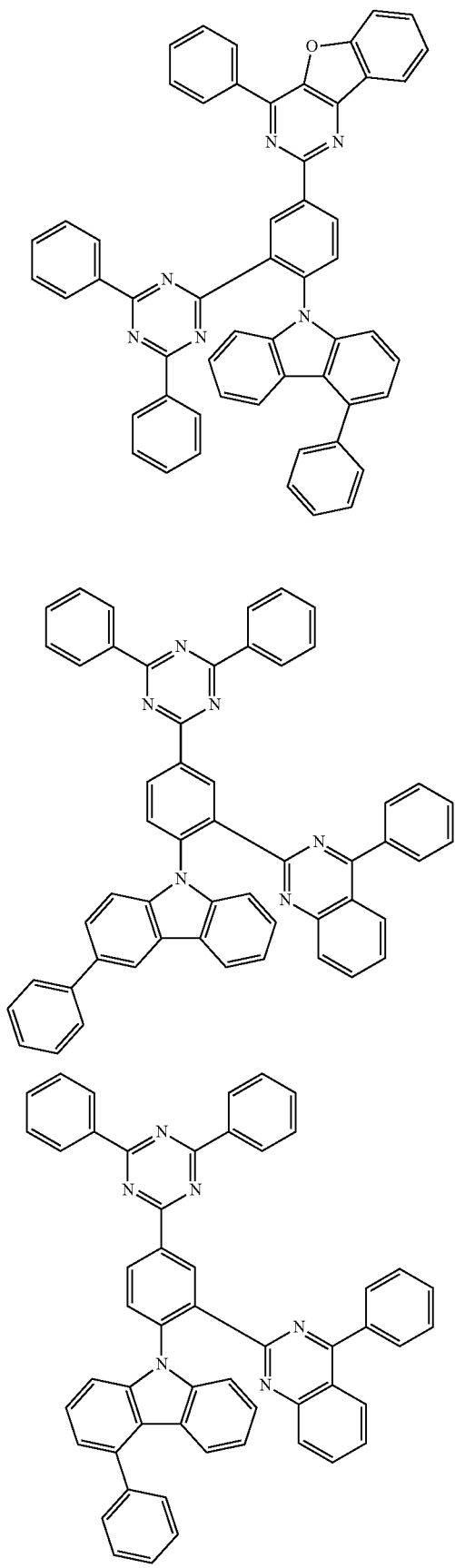
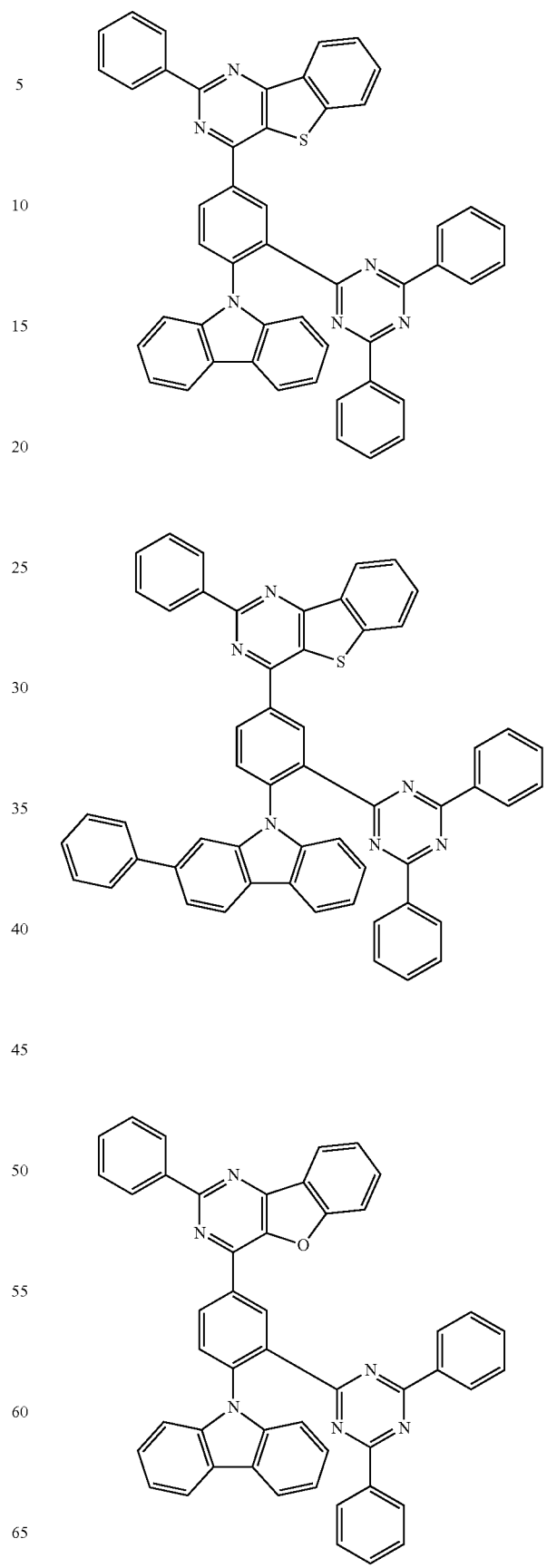

15
-continued
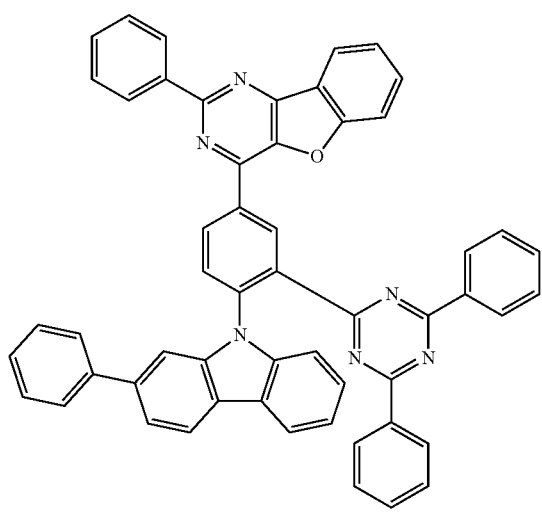
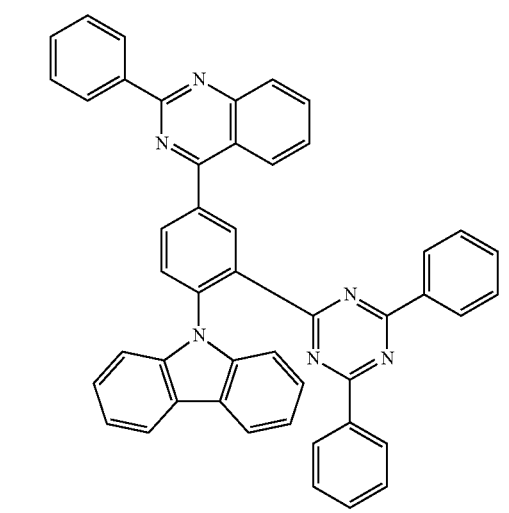
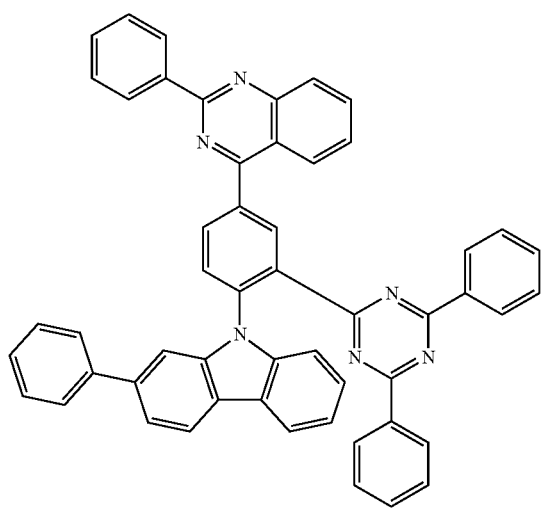
16
-continued
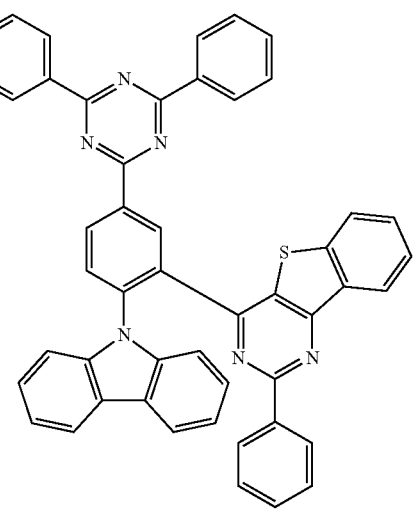
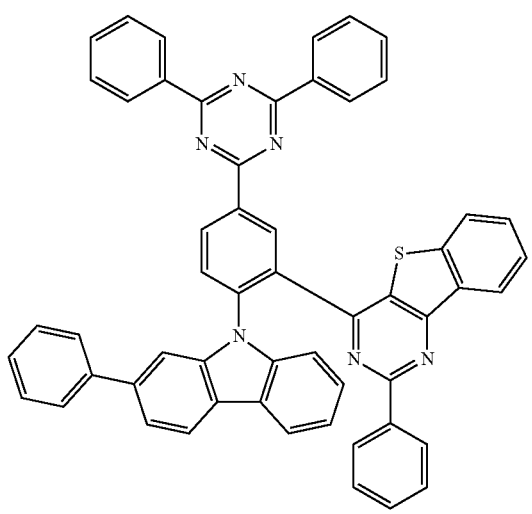
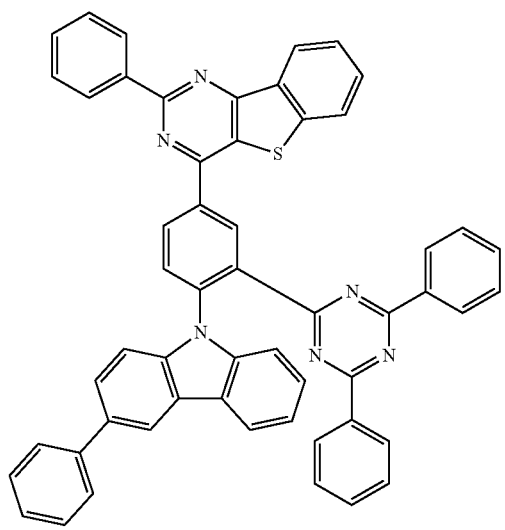

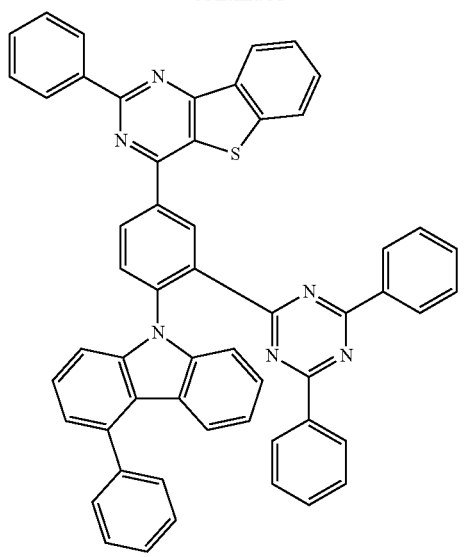
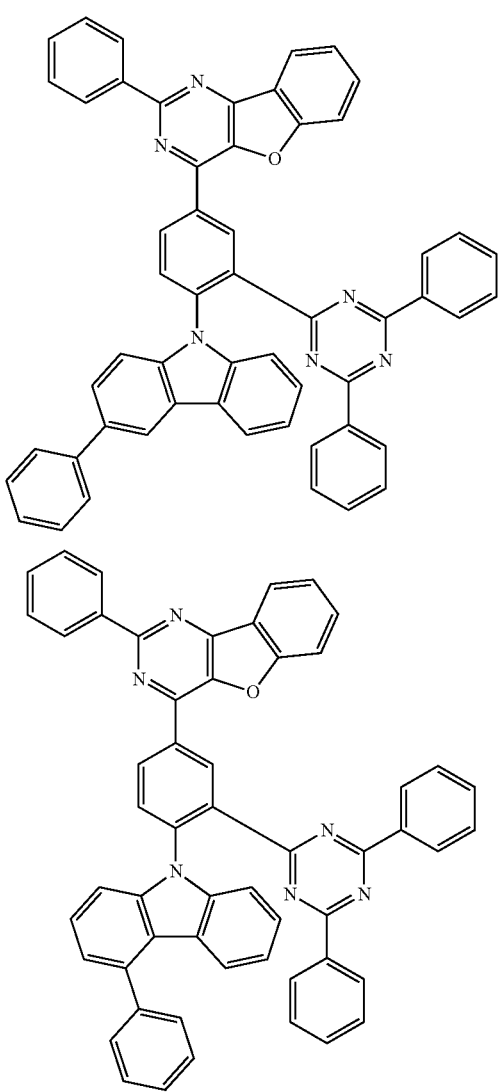
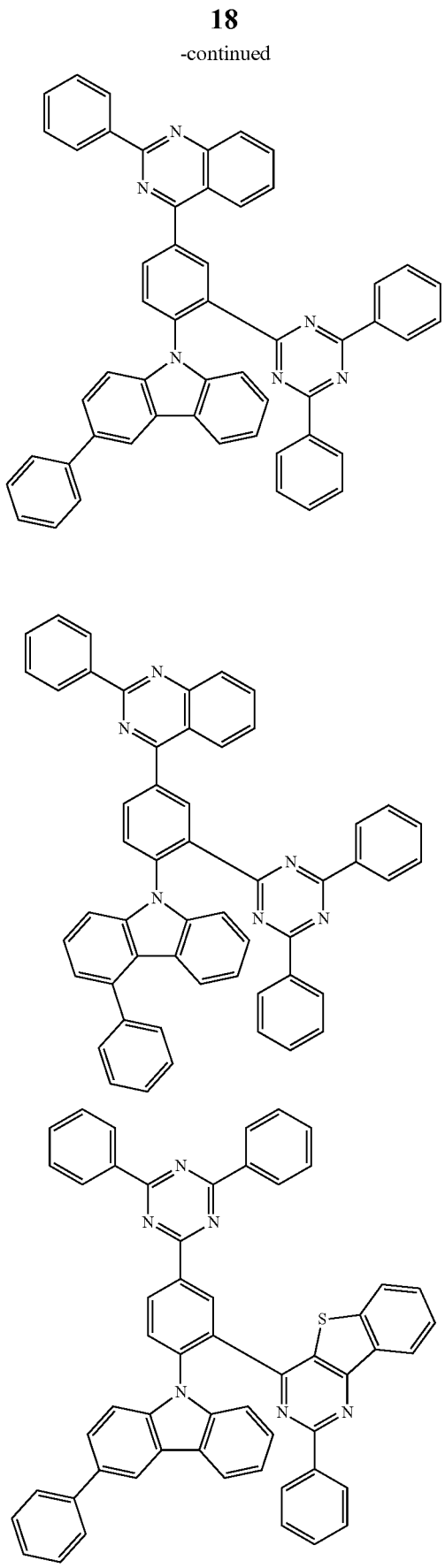

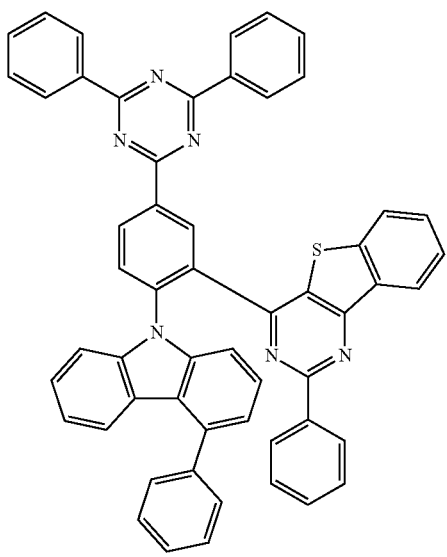
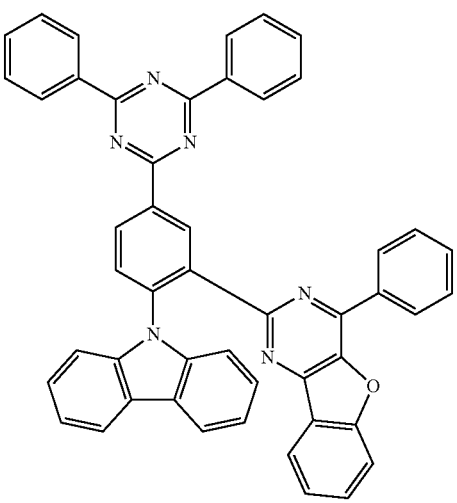
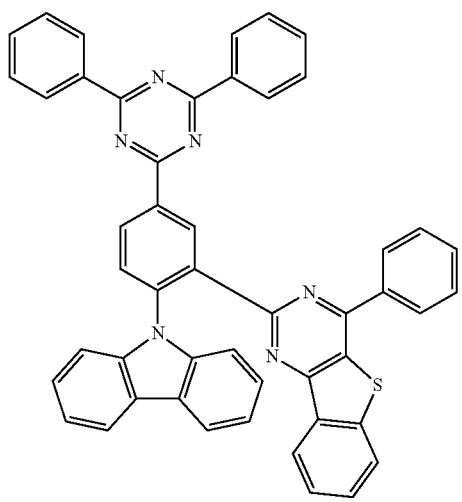
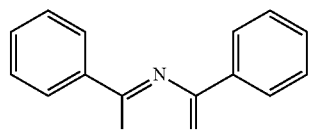
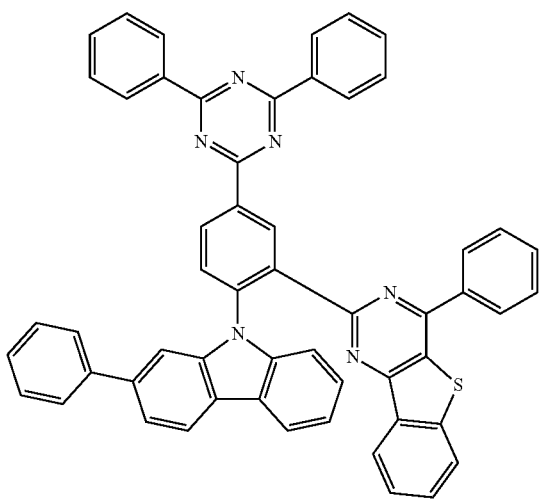
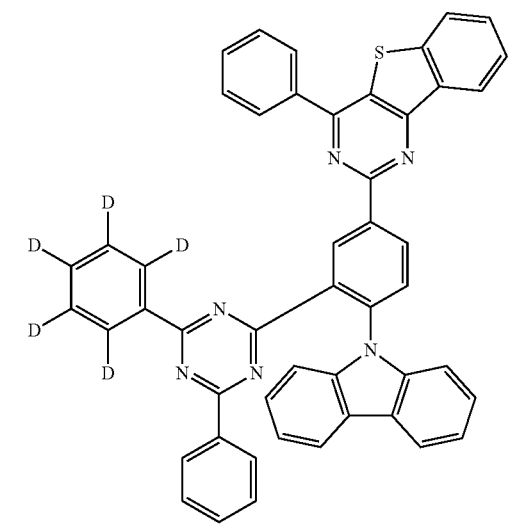

-continued
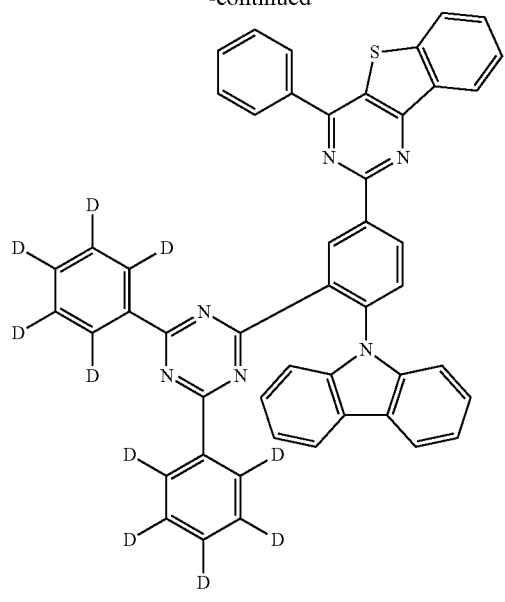
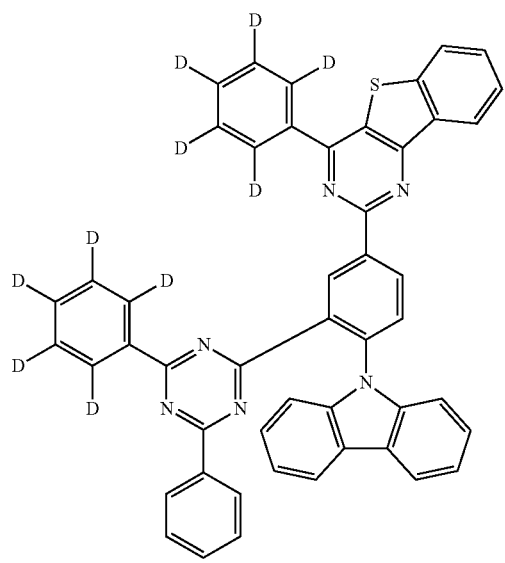
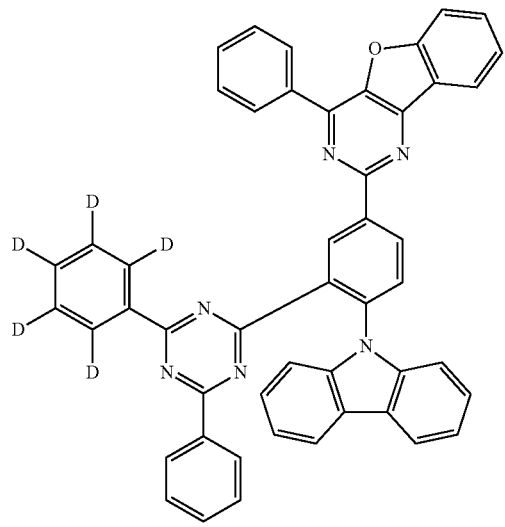
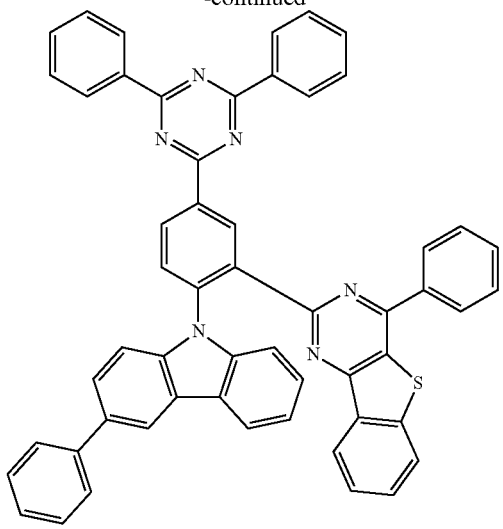
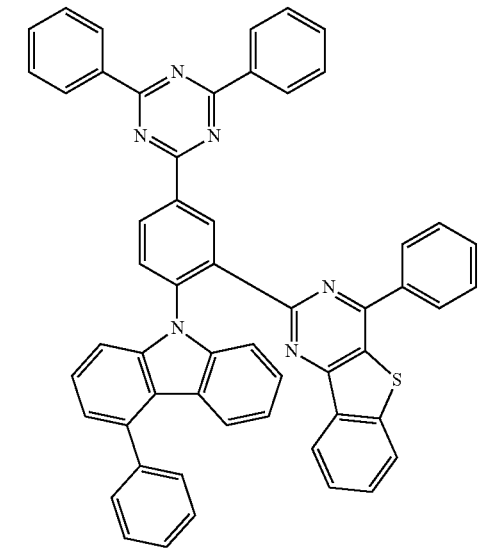
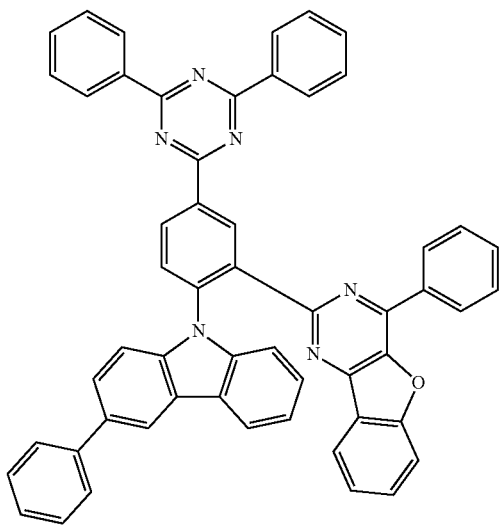

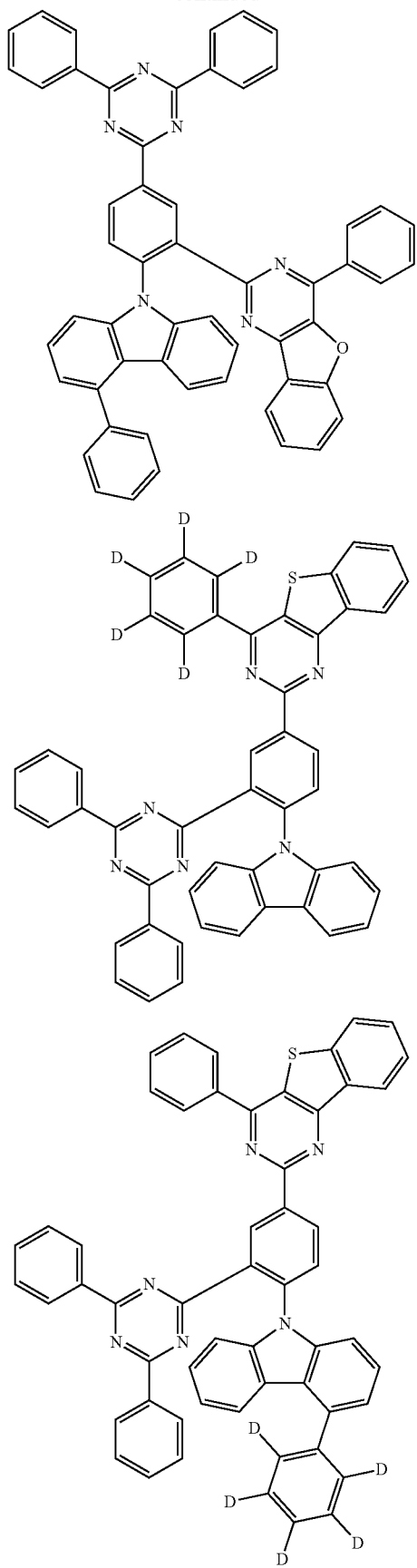
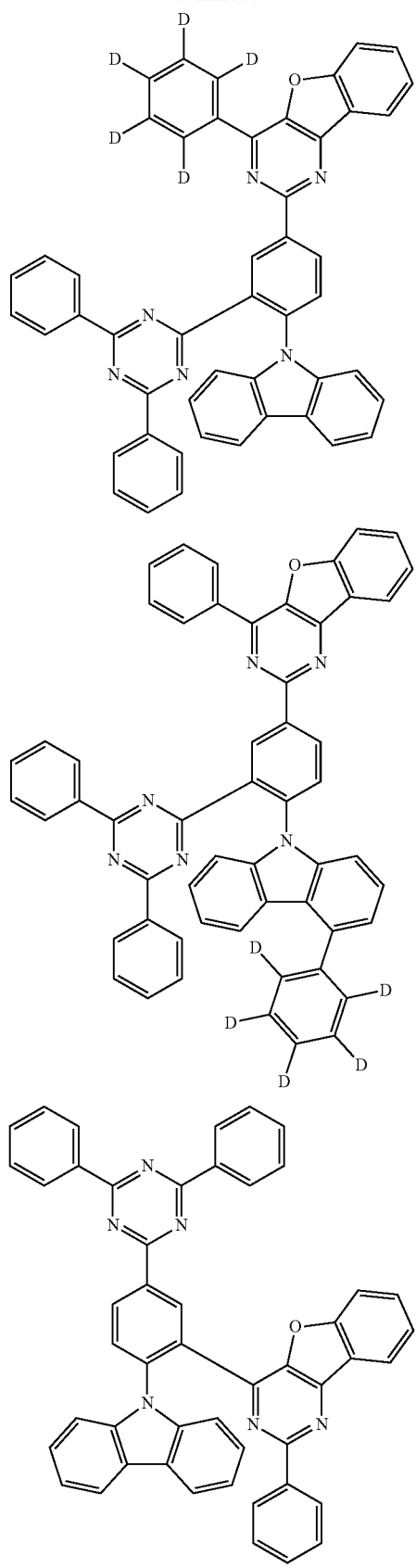

-continued
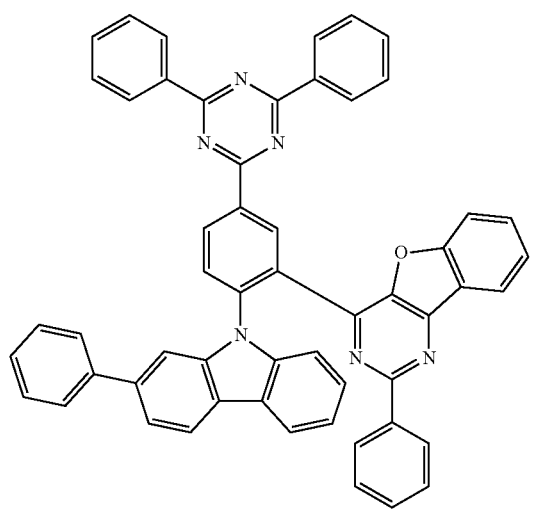
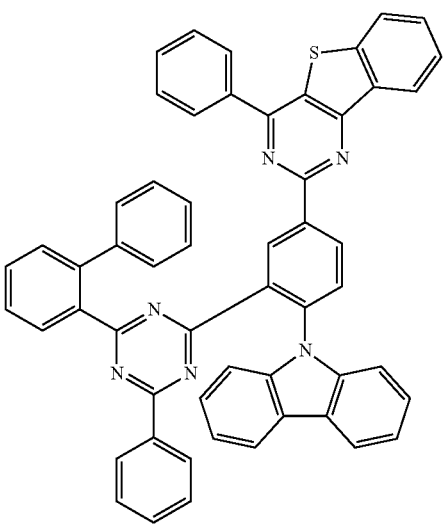

27
-continued
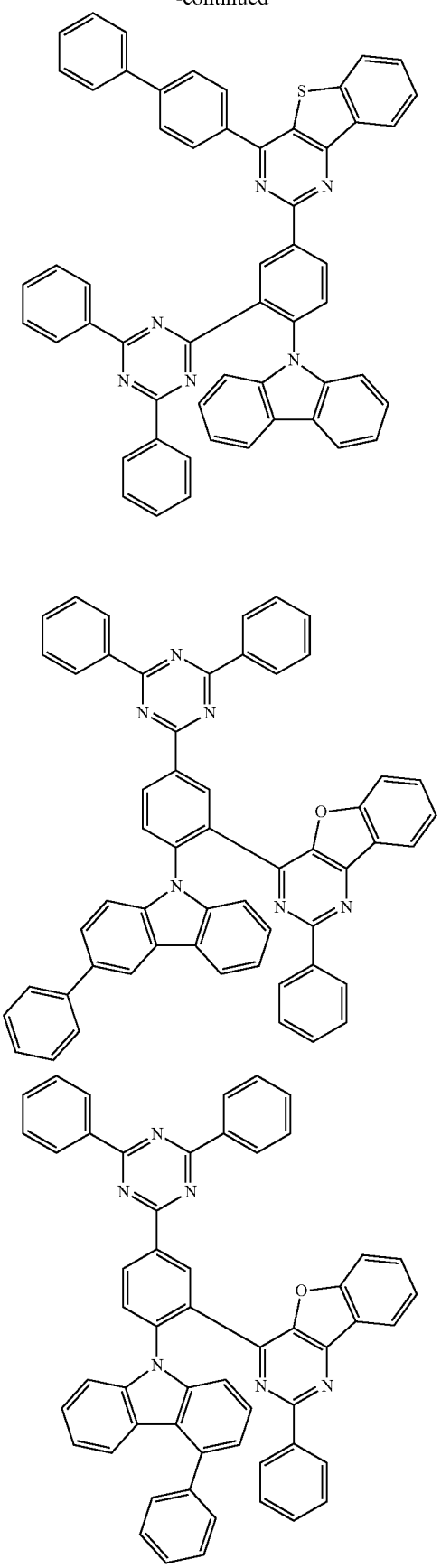
28
-continued
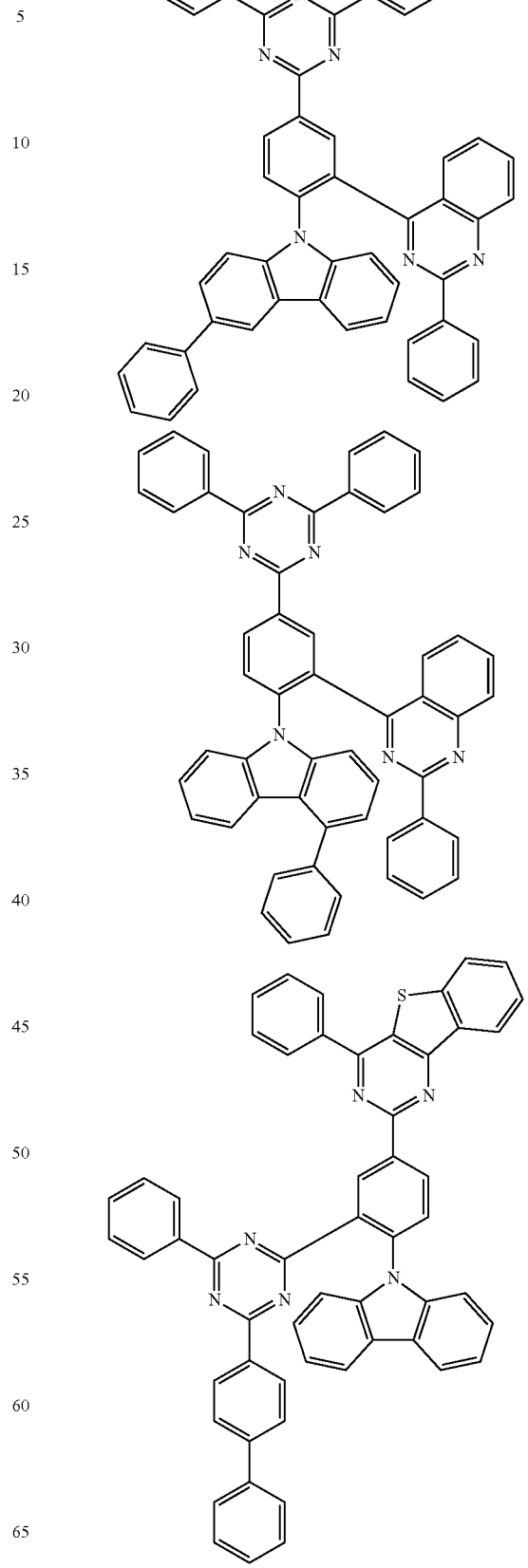

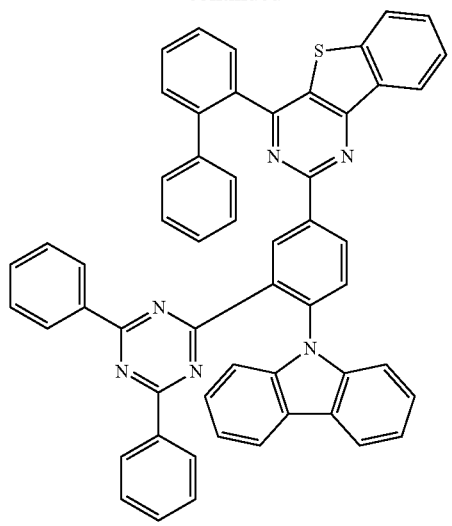
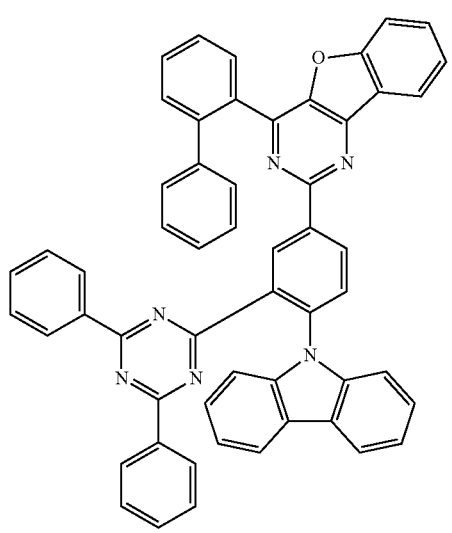
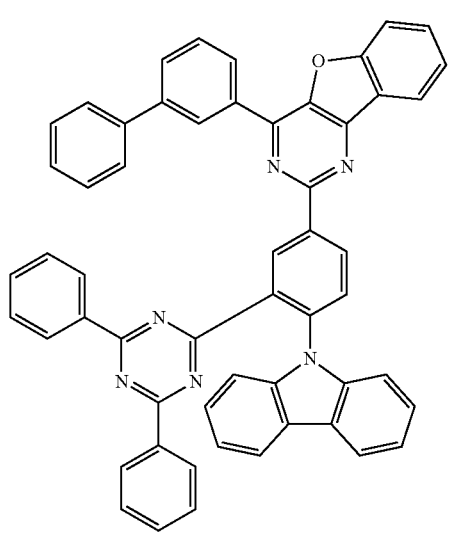
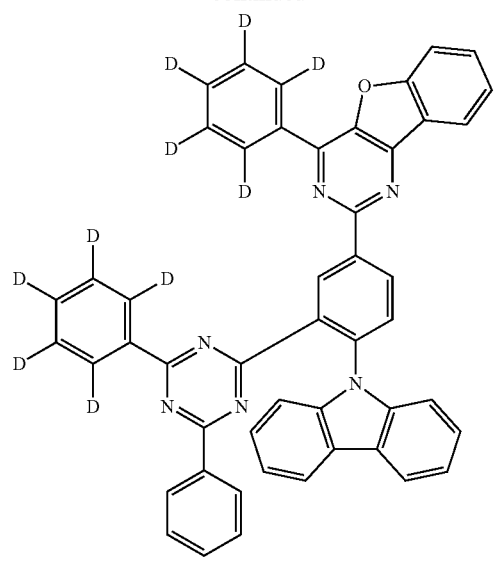
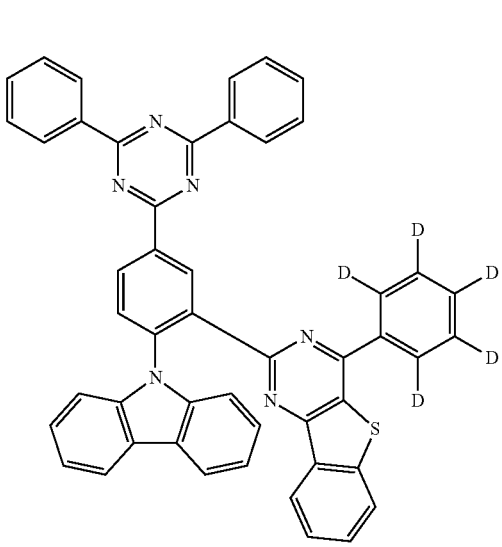
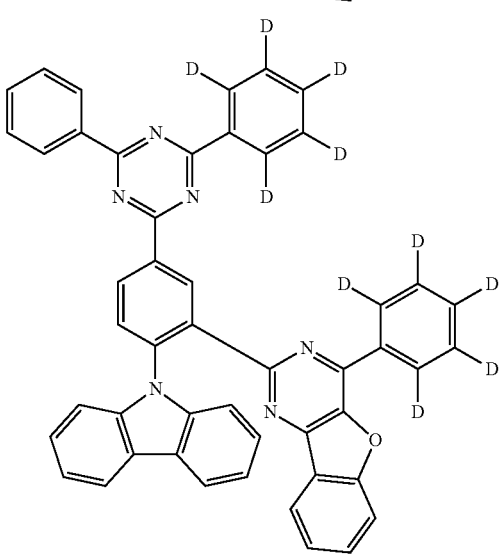

31
-continued
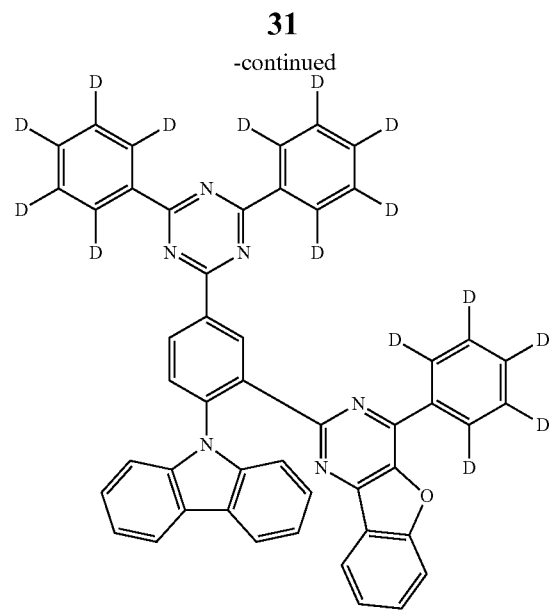
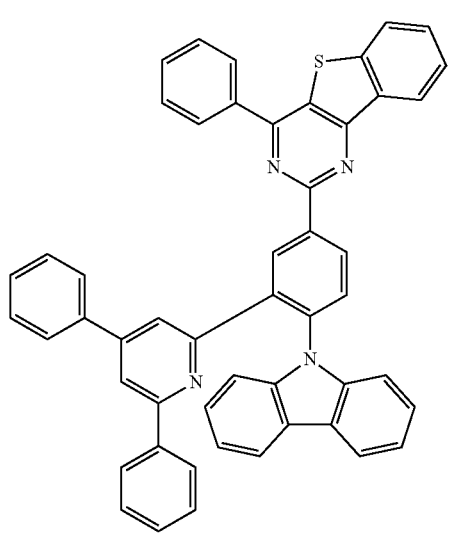
32
-continued
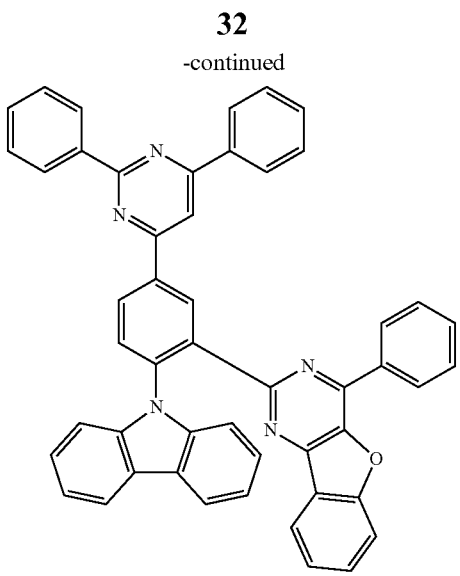
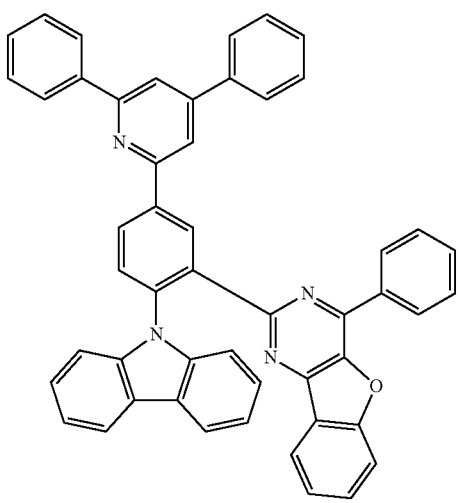
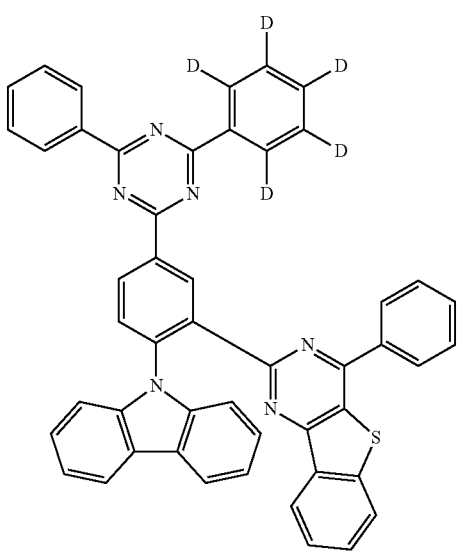
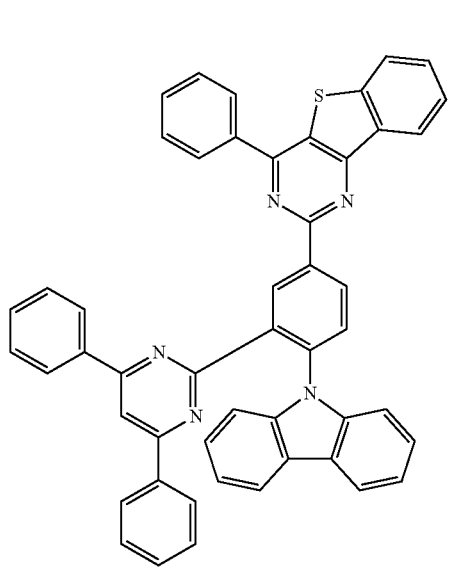

33
-continued
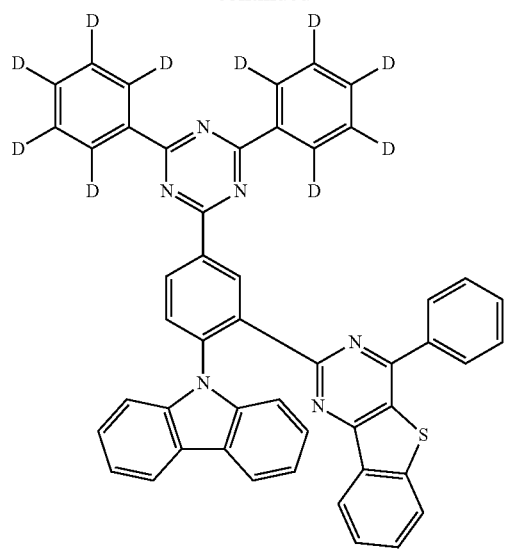
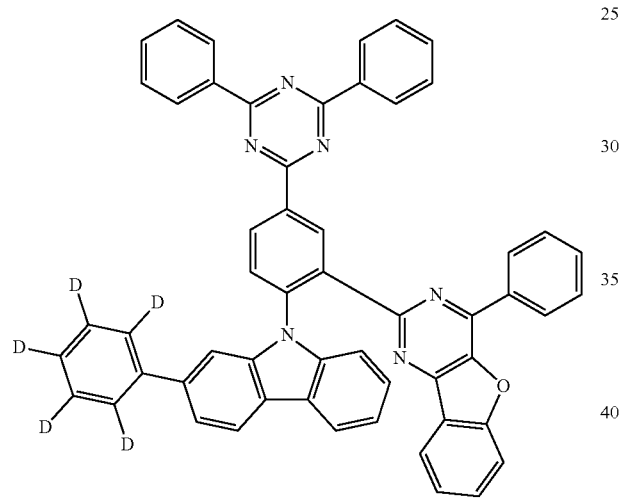
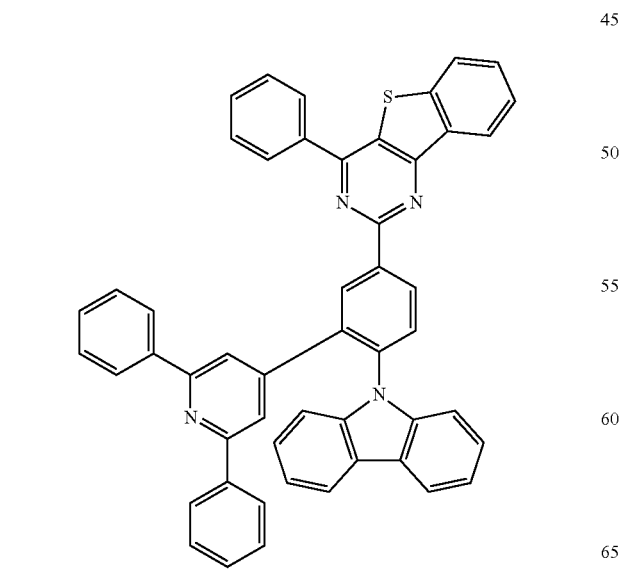
34
-continued
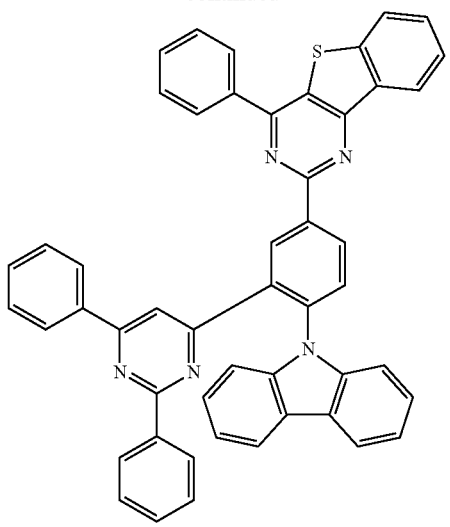
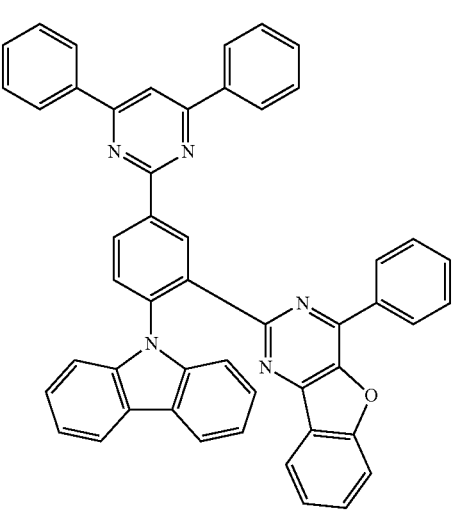
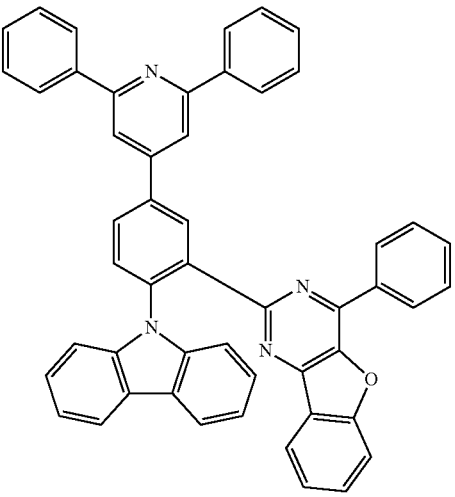

35
-continued
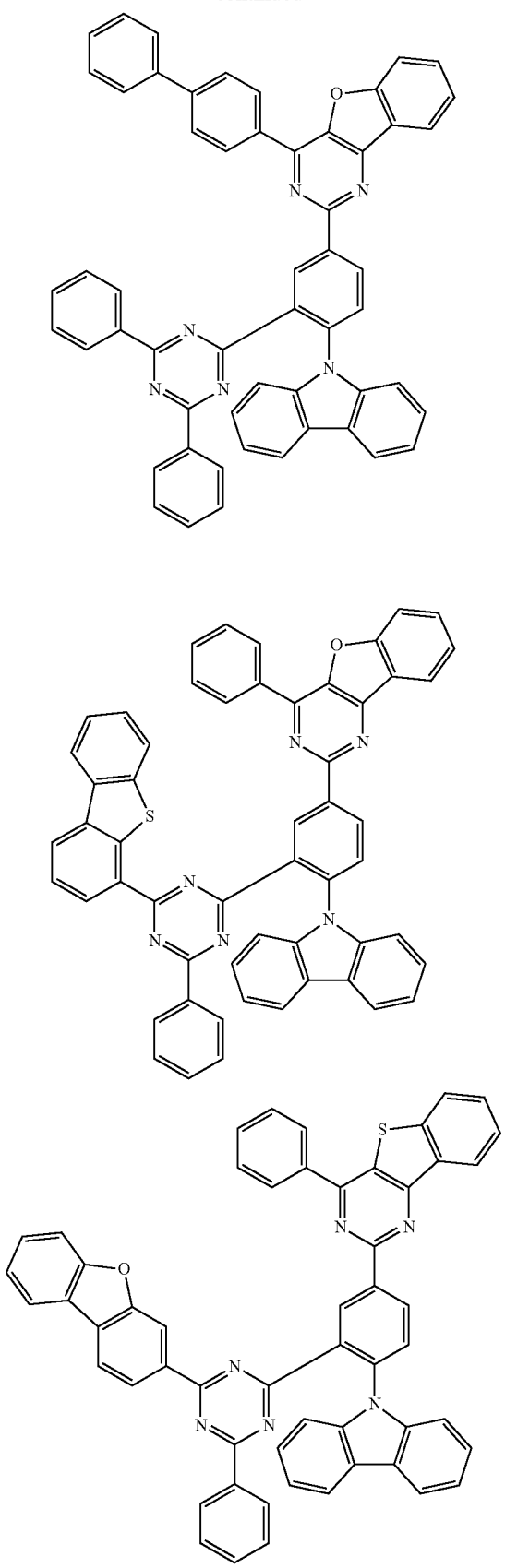
36
-continued
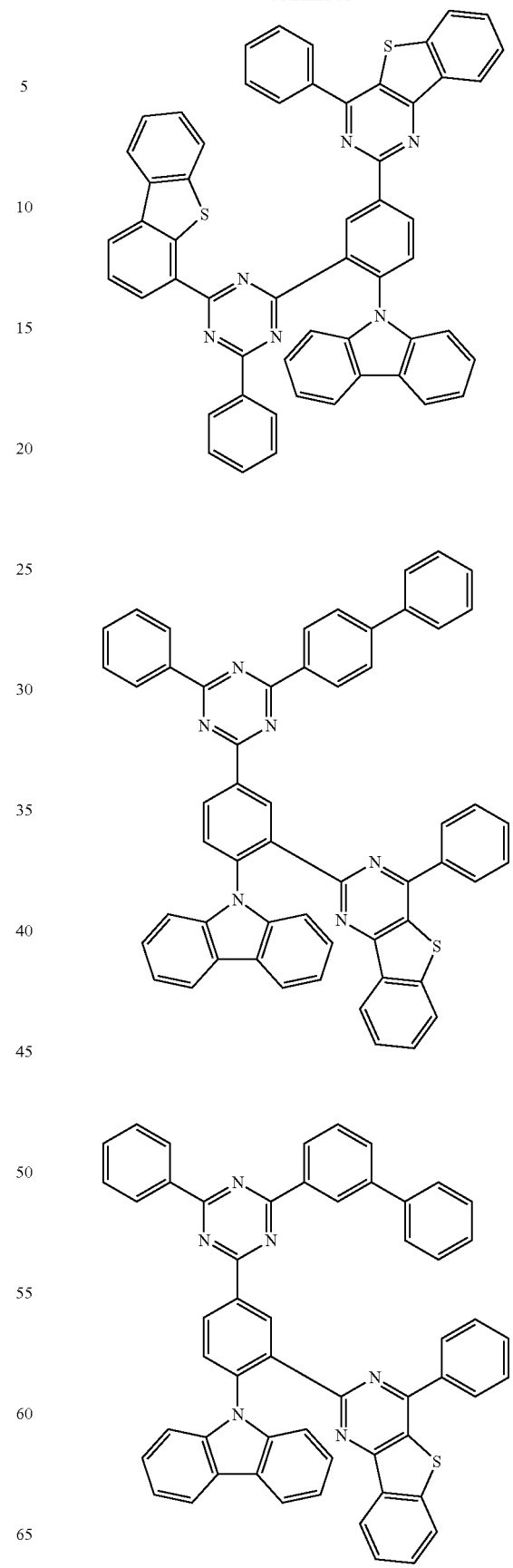

37
-continued
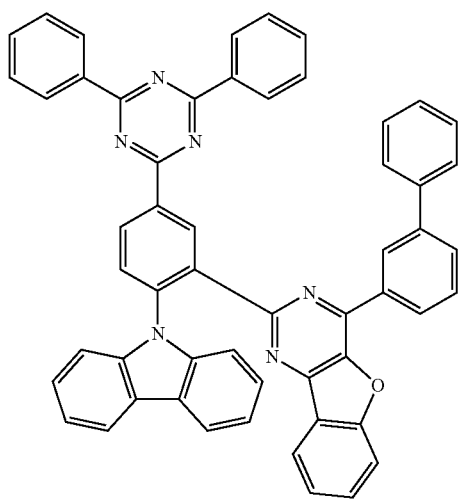
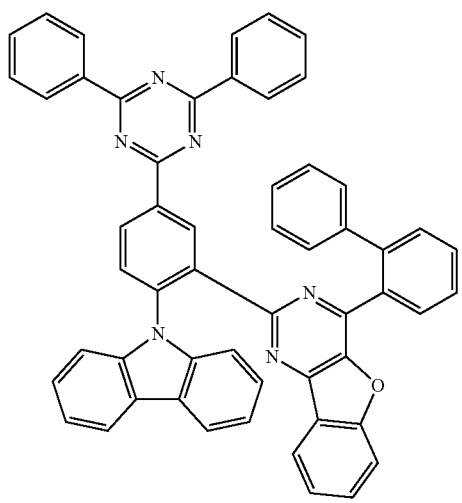
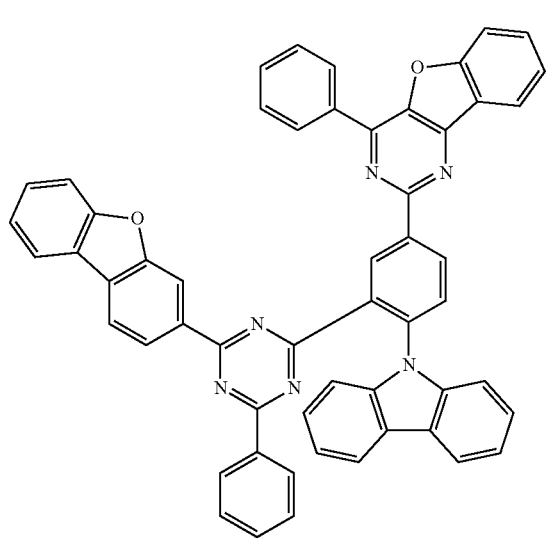
38
-continued
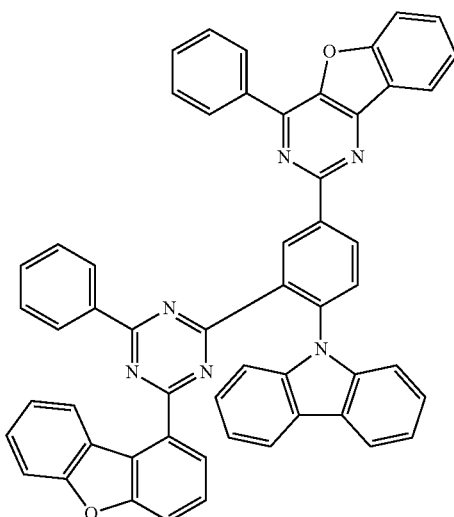
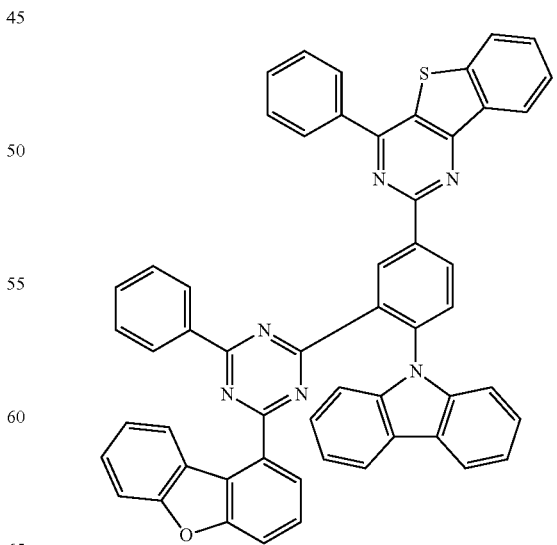

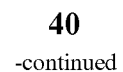
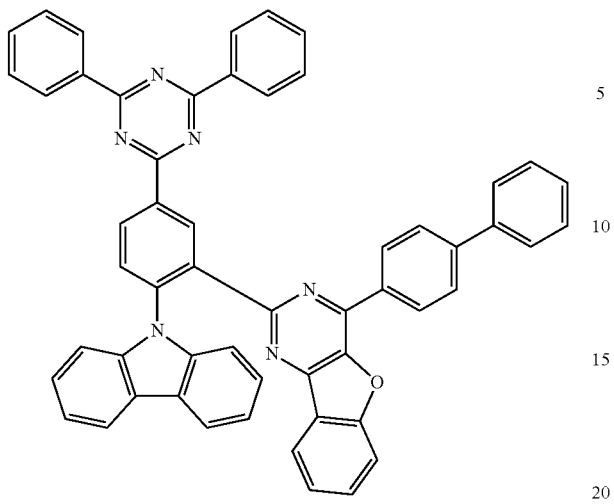
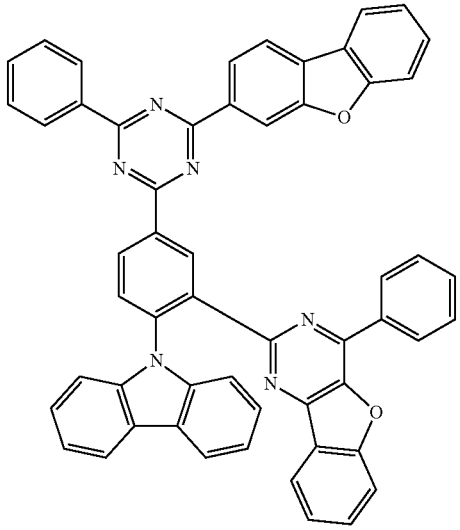
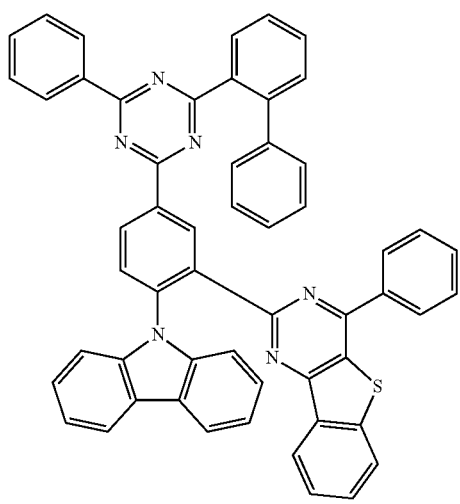
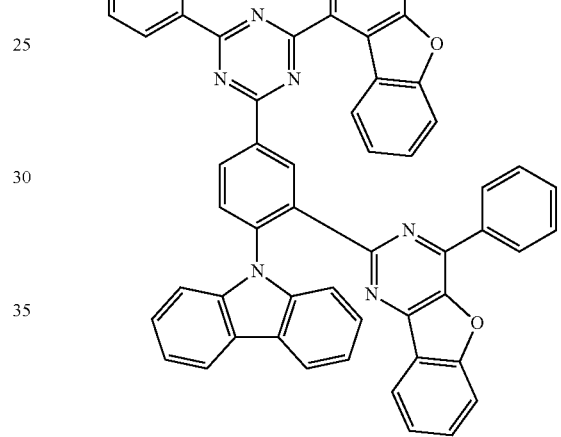
The compound represented by Chemical Formula 1 or 2 may be prepared in accordance with a preparation method as shown in Reaction Scheme 1 or 2 below.
[Reaction Scheme 1]
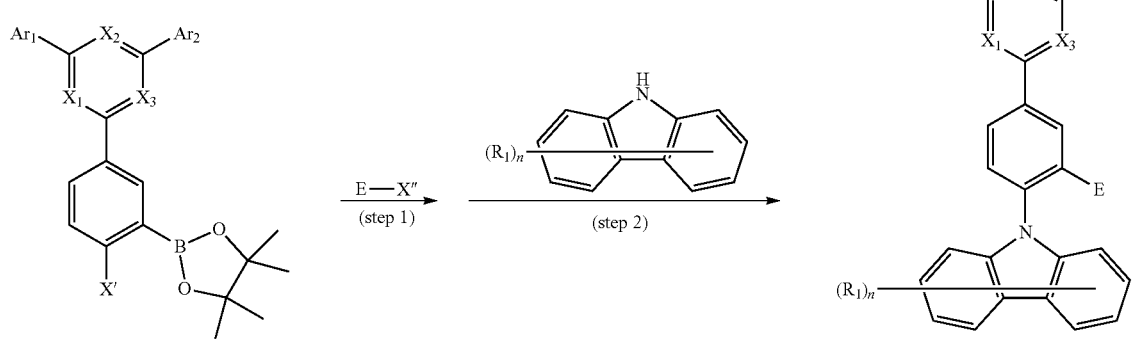

[Reaction Scheme 2]

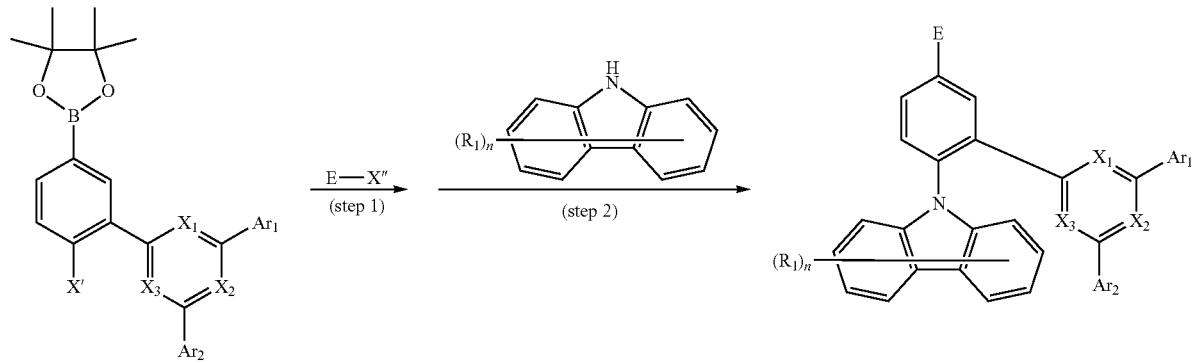

In Reaction Schemes 1 and 2, the definitions of the substituents except X' and X" are the same as those described above, and X' and X" are each independently a halogen. Preferably, X' is fluoro, and X" is chloro or bromo.

The step 1 of Reaction Schemes 1 and 2 is a Suzuki coupling reaction, which is preferably carried out in the presence of a palladium catalyst and a base, and a reactive group for the Suzuki coupling reaction can be modified as known in the art. Further, the step 2 of Reaction Schemes 1 and 2 is an amine substitution reaction, which is preferably carried out in the presence of a palladium catalyst and a base, and a reactive group for the amine substitution reaction can be modified as known in the art.

The above preparation method can be further specified in the preparation examples described later.

Another embodiment of the present disclosure provides an organic light emitting device including a compound represented by Chemical Formula 1 or 2 described above. As an example, there is provided an organic light emitting device including a first electrode; a second electrode provided to face the first electrode; and one or more organic material layers provided between the first electrode and the second electrode, wherein one or more layers of the organic material layers include the compound represented by Chemical Formula 1 or 2.

The organic material layer of the organic light emitting device of the present disclosure may have a single-layer structure, or it may have a multilayered structure in which two or more organic material layers are stacked. For example, the organic light emitting device of the present disclosure may have a structure including a hole injection layer, a hole transport layer, a light emitting layer, an electron blocking layer, an electron transport layer, an electron injection layer and the like as the organic material layer. However, the structure of the organic light emitting device is not limited thereto, and it may include a smaller number of organic material layers.

Further, the organic material layer may include a light emitting layer, wherein the light emitting layer may include the compound represented by Chemical Formula 1 or 2.

Further, the organic material layer may include a hole transport layer, a hole injection layer, or a layer for simultaneously performing hole transport and hole injection, wherein the hole transport layer, the hole injection layer, or the layer for simultaneously performing hole transport and hole injection may include the compound represented by Chemical Formula 1 or 2.

Further, the electron transport layer, the electron injection layer, or the layer for simultaneously performing electron transport and electron injection may include the compound represented by Chemical Formula 1 or 2.

In addition, the organic material layer includes a light emitting layer and a hole transport layer, wherein the light emitting layer and the hole transport layer may include a compound represented by Chemical Formula 1 or 2.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, an organic material layer 3, and a cathode 4. In such a structure, the compound represented by Chemical Formula 1 may be included in the organic material layer.

FIG. 2 shows an example of an organic light emitting device including a substrate 1, an anode 2, a hole injection layer 5, a hole transport layer 6, an electron blocking layer 7, a light emitting layer 8, a hole blocking layer 9, an electron transport layer 10, an electron injection layer 11, and a cathode 4. In such a structure, the compound represented by Chemical Formula 1 or 2 may be included in one or more layers of the hole injection layer, the hole transport layer, the electron blocking layer, the light emitting layer, the hole blocking layer, the electron transport layer, and the electron injection layer.

The organic light emitting device according to the present invention may be manufactured by materials and methods known in the art, except that at least one layer of the organic material layers includes the compound represented by Chemical Formula 1 or 2. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by Chemical Formula 1 or 2 may be formed into an organic material layer by a solution coating method as well as a vacuum deposition method at the time of manufacturing an organic light emitting device. Herein, the solution coating method means spin coating, dip coating, doctor blading, inkjet printing, screen printing, spraying, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

As an example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metalporphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is a layer provided between the hole transport layer and the light emitting layer in order to prevent the electrons injected from the cathode from being transferred to the hole transport layer without being recombined in the light emitting layer, which may also be referred to as an electron inhibition layer. The electron blocking layer is preferably a material having a smaller electron affinity than the electron transport layer.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylene vinylene) (PPV)-based polymer; a spiro compound; polyfluorene; rubrene; and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocycle-containing compounds include carbazole derivatives, dibenzofuran derivatives, ladder-type furan compounds, pyrimidine derivatives, and the like, but are not limited thereto. In one embodiment of the present invention, the compound represented by Chemical Formula 1 or Chemical Formula 2 can be used as a host material of the light emitting layer, and may achieve a low driving voltage, high efficiency, and/or long lifetime characteristics in the organic light emitting device.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including Alq₃; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the material used.

In addition, the compound represented by Chemical Formula 1 may be included in an organic solar cell or an organic transistor in addition to an organic light emitting device.

Hereinafter, embodiments will be described in more detail to facilitate understanding of the invention. However, the following examples are provided for illustrative purposes only and are not intended to limit the scope of the present disclosure.

PREPARATION EXAMPLES

Preparation Example 1: Preparation of Compound 1

Step 1) Preparation of Compound 1-a

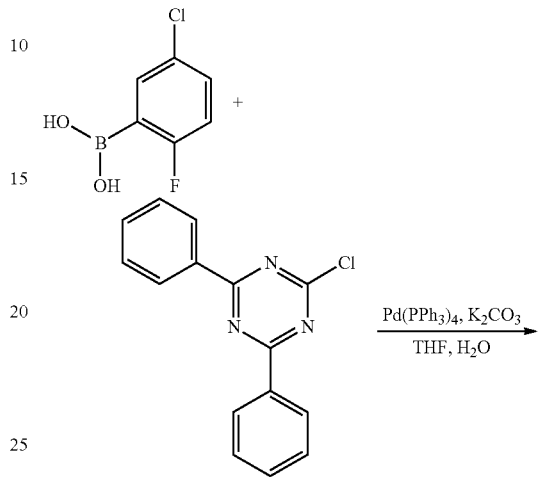

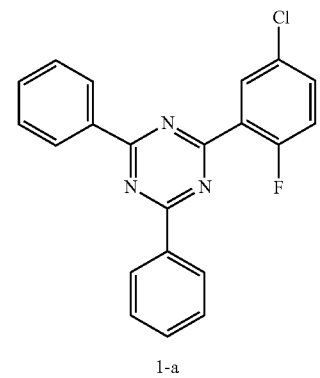

1-a (5-chloro-2-fluorophenyl) boronic acid (20 g, 114.7 mmol) and 2-chloro-4,6-diphenyl-1,3,5-triazine (30.7 g, 114.7 mmol) were added to 400 ml of tetrahydrofuran under a nitrogen atmosphere, and the mixture was stirred and refluxed. Then, potassium carbonate (47.6 g, 344.1 mmol) was dissolved in 48 ml of water, added thereto and sufficiently stirred, and then tetrakistriphenyl-phosphinopalladium (4 g, 3.4 mmol) was added. After reaction for 2 hours, the reaction mixture was cooled to room temperature, the organic layer and the water layer was separated, and then the organic layer was distilled. This was added again to 830 mL of chloroform, dissolved and washed twice with water. The organic layer was then separated, anhydrous magnesium sulfate was added, stirred, and then filtered. The filtrate was distilled under reduced pressure. The concentrated compound was purified by silica gel column chromatography to give a white solid compound 1-a (32.4 g, 78%, MS: $[M+H]^+= 362.8$).

Step 2) Preparation of Compound 1-b

Step 3) Preparation of Compound 1-c

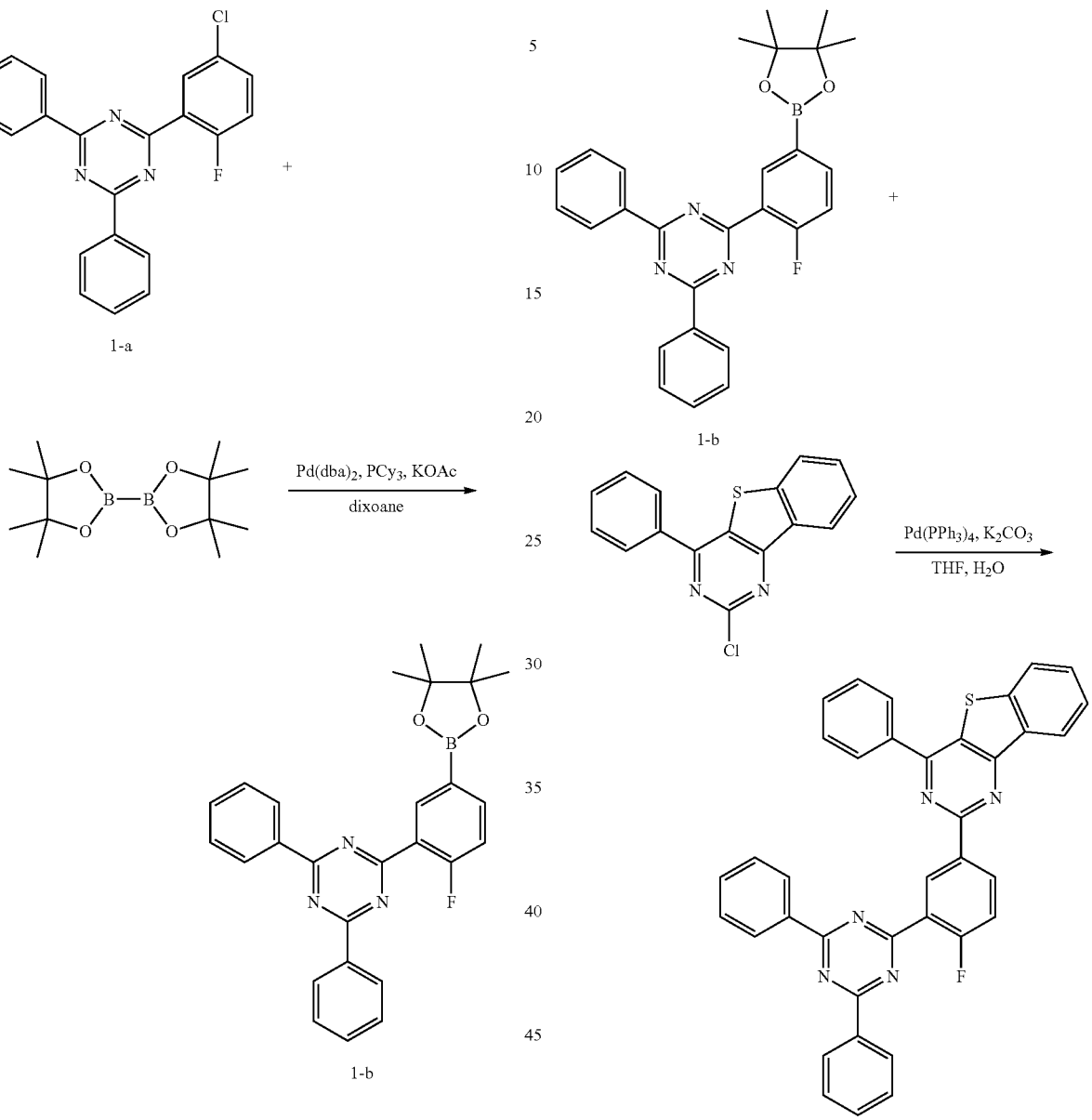

Compound 1-a (20 g, 55.3 mmol) and bis(pinacolato) diboron (14 g, 55.3 mmol) were added to 400 ml of dioxane under a nitrogen atmosphere, and the mixture was stirred and refluxed. Then, anhydrous potassium acetate (16.3 g, 165.8 mmol) was added thereto and sufficiently stirred, and then palladium dibenzylidene acetone palladium (1 g, 1.7 mmol) and tricyclohexylphosphine (0.9 g, 3.3 mmol) were added. After reaction for 3 hours, the reaction mixture was cooled to room temperature and then the organic layer was subjected to filtration treatment to remove a salt, and then the filtered organic layer was distilled. This was added again to 251 mL of chloroform, dissolved and washed twice with water. The organic layer was then separated, anhydrous magnesium sulfate was added, stirred, and then filtered. The filtrate was distilled under reduced pressure. The concentrated compound was purified by recrystallization with chloroform and ethanol to give a white solid 1-b (17 g, 68%, MS: [M+H]$^+$=454.3).

Compound 1-b (20 g, 44.1 mmol) and 2-chloro-4-phenylbenzo[4,5]thieno[3,2-d]pyrimidine (13.1 g, 44.1 mmol) were added to 400 ml of tetrahydrofuran under a nitrogen atmosphere, and the mixture was stirred and refluxed. Then, potassium carbonate (18.3 g, 132.4 mmol) was dissolved in 18 ml of water, added thereto and sufficiently stirred, and then tetrakistriphenyl-phosphinopalladium (1.5 g, 1.3 mmol) was added. After reaction for 3 hours, the reaction mixture was cooled to room temperature and then the produced solid was filtered. The solid was added to 519 mL of choloroform, dissolved and washed twice with water. The organic layer was then separated, anhydrous magnesium sulfate was added, stirred, and then filtered. The filtrate was distilled under reduced pressure. The concentrated compound was purified by recrystallization with chloroform and ethyl acetate to give a white solid 1-c (16.6 g, 64%, MS: [M+H]$^+$=588.7).

Step 4) Preparation of Compound 1

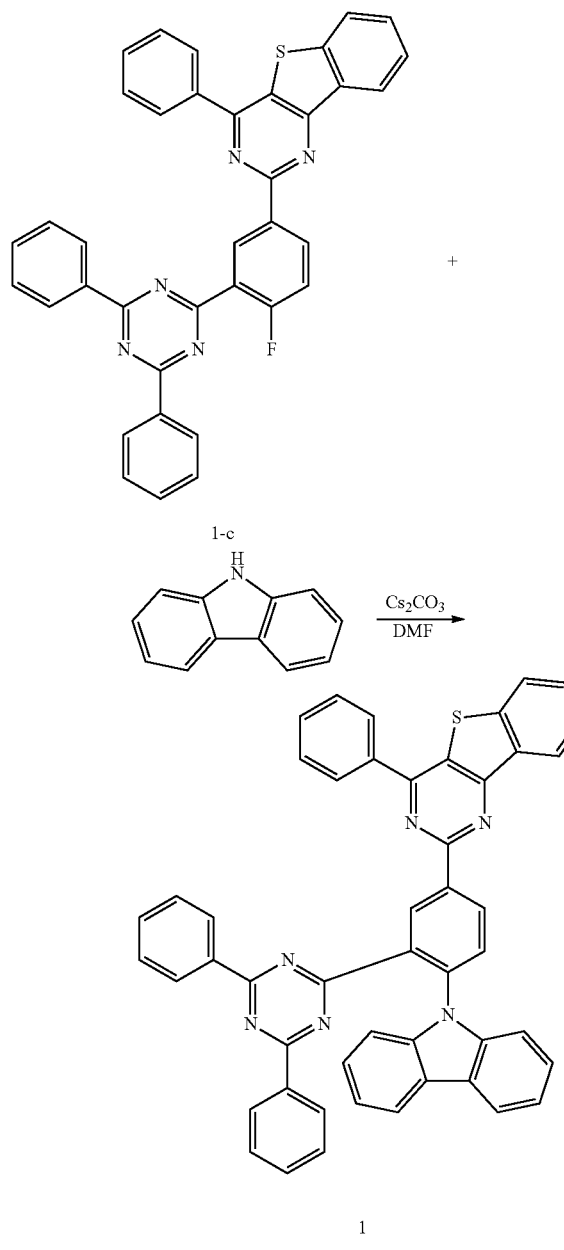

Compound 1-c (20 g, 34 mmol) and carbazole (5.7 g, 34 mmol) were added to 400 ml of dimethylformamide under a nitrogen atmosphere, and the mixture was stirred and refluxed. Then, cesium carbonate (33.3 g, 102.1 mmol) was added thereto and raised the temperature while stirring. After reaction for 3 hours, the reaction mixture was cooled to room temperature and then the organic layer was subjected to filtration treatment to remove a salt, and then the filtered organic layer was distilled. This was again added to 250 mL of chloroform, dissolved and washed twice with water. The organic layer was then separated, anhydrous magnesium sulfate was added, stirred, and then filtered. The filtrate was distilled under reduced pressure. The concentrated compound was purified by silica gel column chromatography and sublimation purification to give compound 1 (12.8 g, 51%, MS: [M+H]$^+$=735.9).

Preparation Example 2: Preparation of Compound 2

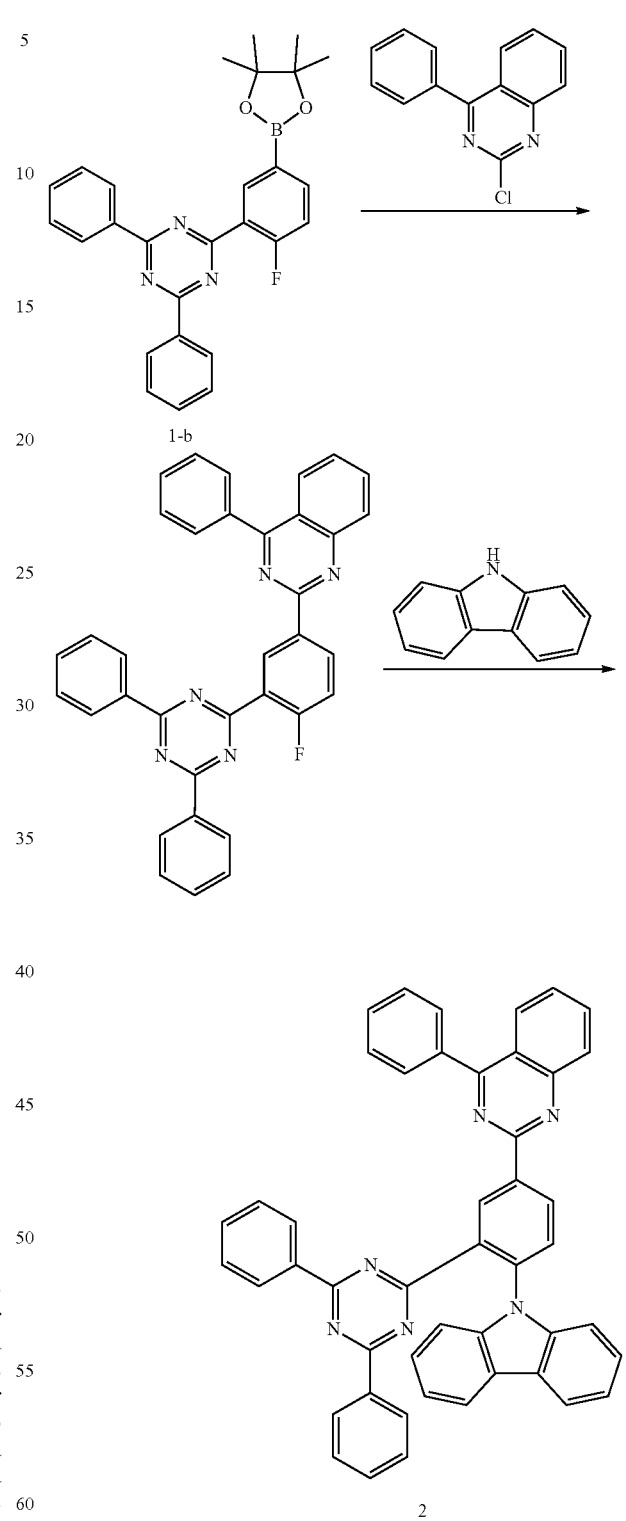

Compound 2 was prepared in the same manner as the preparation method of Compound 1, except that 2-chloro-4-phenylquinazoline was used instead of 2-chloro-4-phenyl-benzo[4,5]thieno[3,2-d]pyrimidine in Step 3 of Preparation Example 1 (MS [M+H]+=679.8).

Preparation Example 3: Preparation of Compound 3
Preparation Example 4: Preparation of Compound 4
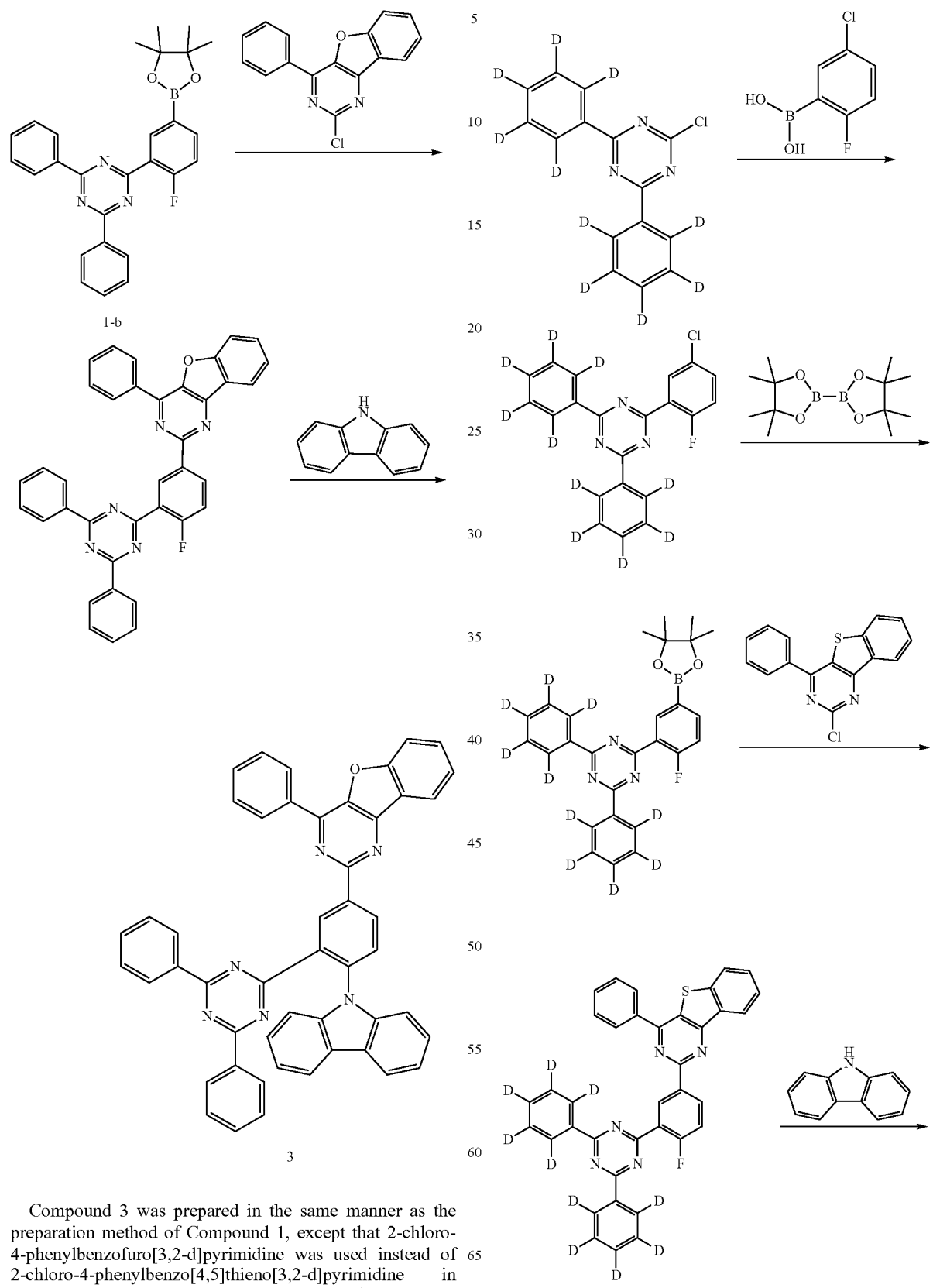
Compound 3 was prepared in the same manner as the preparation method of Compound 1, except that 2-chloro-4-phenylbenzofuro[3,2-d]pyrimidine was used instead of 2-chloro-4-phenylbenzo[4,5]thieno[3,2-d]pyrimidine in Step 3 of Preparation Example 1 (MS [M+H]$^+$=719.8).

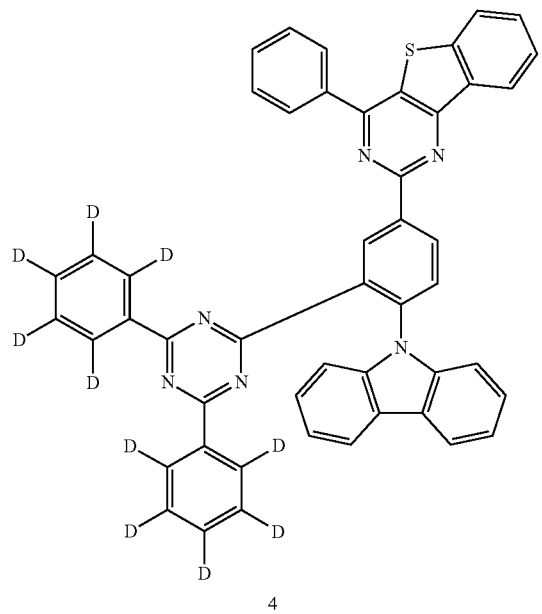 [SMILES: [2H]c1c([2H])c([2H])c(-c2nc(-c3cc(-c4nc(-c5ccccc5)c5sc6ccccc6c5n4)ccc3-n3c4ccccc4c4ccccc43)nc(-c3c([2H])c([2H])c([2H])c([2H])c3[2H])n2)c([2H])c1[2H]]

4

Compound 4 was prepared in the same manner as the preparation Example 1, except that 2-chloro-4,6-bis(phenyl-d5)-1,3,5-triazine was used instead of 2-chloro-4,6-diphenyl-1,3,5-triazine (MS [M+H]$^+$=745.0).

Preparation Example 5: Preparation of Compound 5

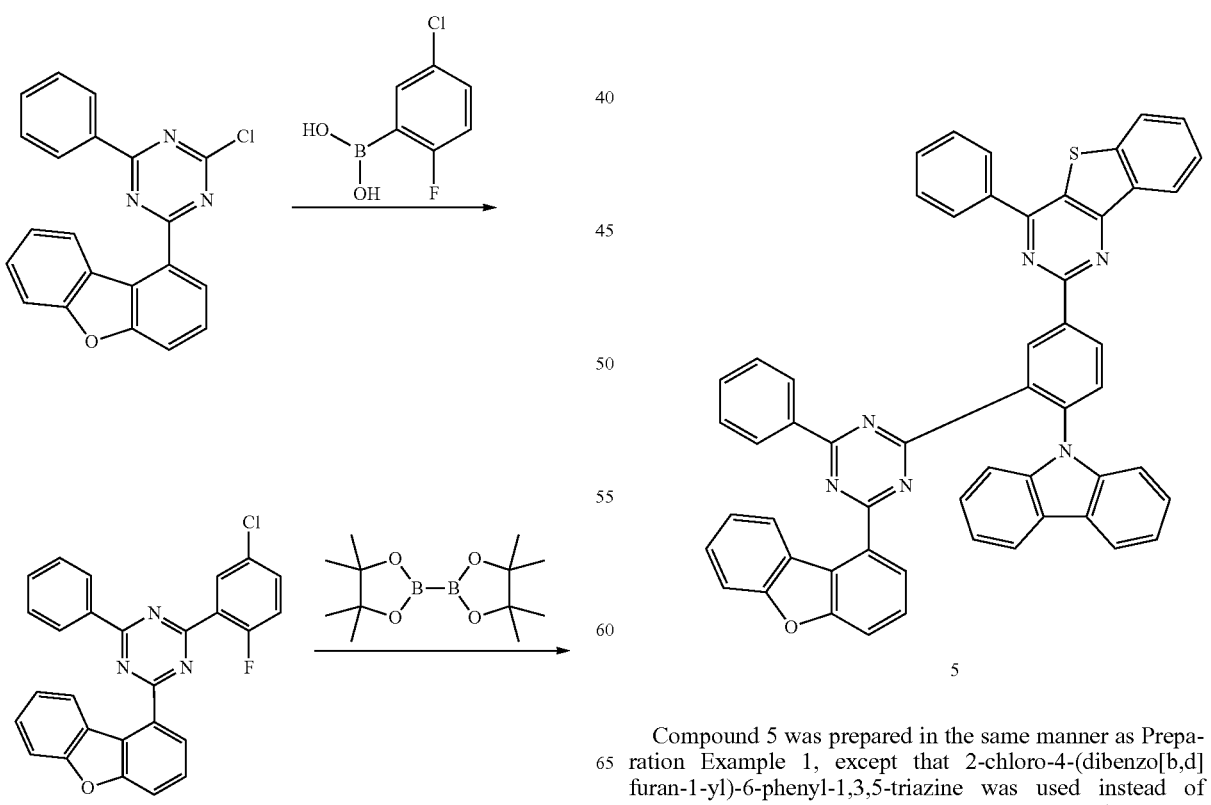

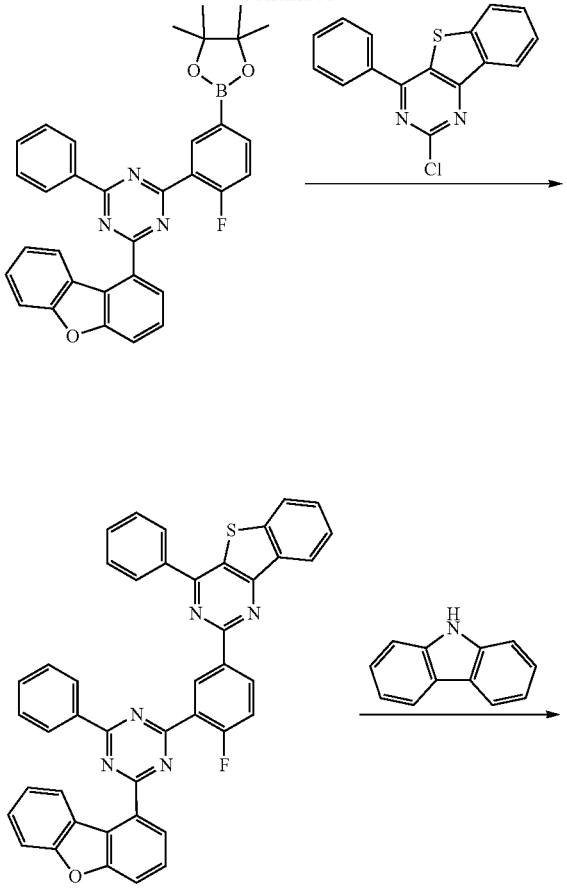

5

Compound 5 was prepared in the same manner as Preparation Example 1, except that 2-chloro-4-(dibenzo[b,d]furan-1-yl)-6-phenyl-1,3,5-triazine was used instead of 2-chloro-4,6-diphenyl-1,3,5-triazine (MS [M+H]$^+$=826.0).

Preparation Example 6: Preparation of Compound 6

Step 1) Preparation of Compound 6-a

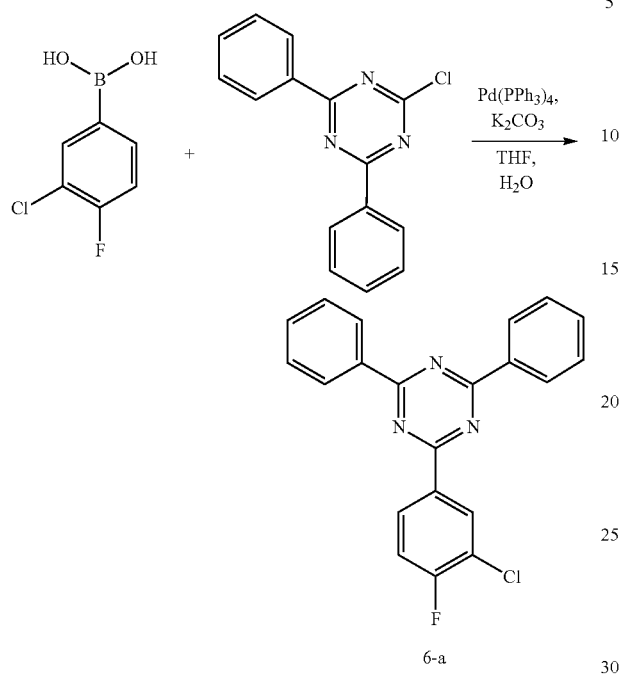

6-a 2-chloro-4,6-diphenyl-1,3,5-triazine (20 g, 74.7 mmol) and (3-chloro-4-fluorophenyl)boronic acid (13 g, 74.7 mmol) were added to 400 ml of tetrahydrofuran under a nitrogen atmosphere, and the mixture was stirred and refluxed. Then, potassium carbonate (31 g, 224.1 mmol) was dissolved in 31 ml of water, added thereto and sufficiently stirred, and then tetrakis triphenyl-phosphinopalladium (2.6 g, 2.2 mmol) was added. After reaction for 2 hours, the reaction mixture was cooled to room temperature, the organic layer and the water layer was separated, and then the organic layer was distilled. This was added again to 541 mL of choloroform, dissolved and washed twice with water. The organic layer was then separated, anhydrous magnesium sulfate was added, stirred, and then filtered. The filtrate was distilled under reduced pressure. The concentrated compound was purified by silica gel column chromatography to give a white solid compound 6-a (21.6 g, 80%, MS: [M+H]$^+$= 362.8).

Step 2) Preparation of Compound 6-b

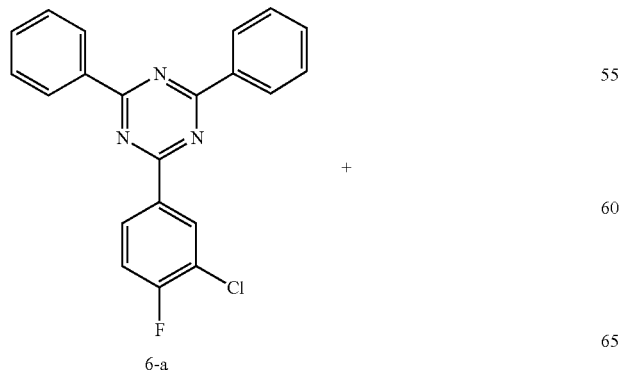

6-a

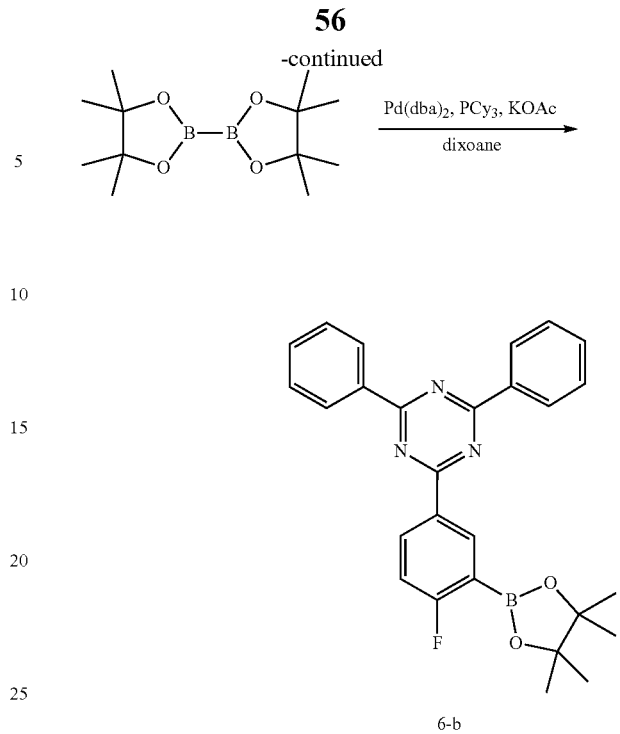

6-b

Compound 6-a (20 g, 55.3 mmol) and bis(pinacolato) diboron (14 g, 55.3 mmol) were added to 400 ml of dioxane under a nitrogen atmosphere, and the mixture was stirred and refluxed. Then, anhydrous potassium acetate (16.3 g, 165.8 mmol) was added thereto and sufficiently stirred, and then bis(dibenzylideneacetone)palladium (1 g, 1.7 mmol) and tricyclohexylphosphine (0.9 g, 3.3 mmol) were added. After reaction for 3 hours, the reaction mixture was cooled to room temperature and then the organic layer was subjected to filtration treatment to remove a salt, and then the filtered organic layer was distilled. This was added again to 251 mL of chloroform, dissolved and washed twice with water. The organic layer was then separated, anhydrous magnesium sulfate was added, stirred, and then filtered. The filtrate was distilled under reduced pressure. The concentrated compound was purified by recrystallization with chloroform and ethanol to give a white solid 6-b (18.5 g, 74%, MS: [M+H]$^+$=454.3).

Step 3) Preparation of Compound 6-c

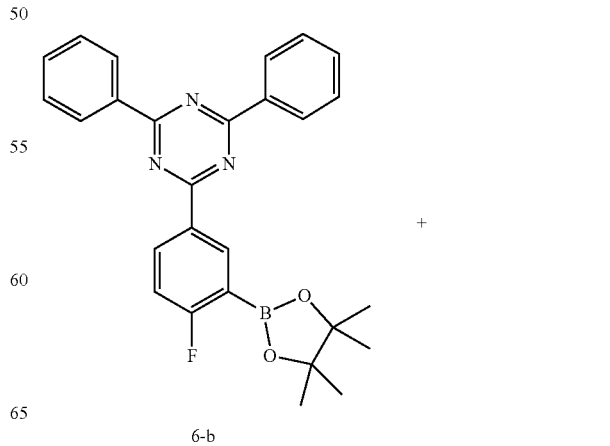

6-b

-continued

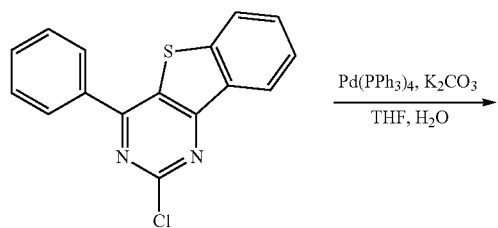

Step 4) Preparation of Compound 6

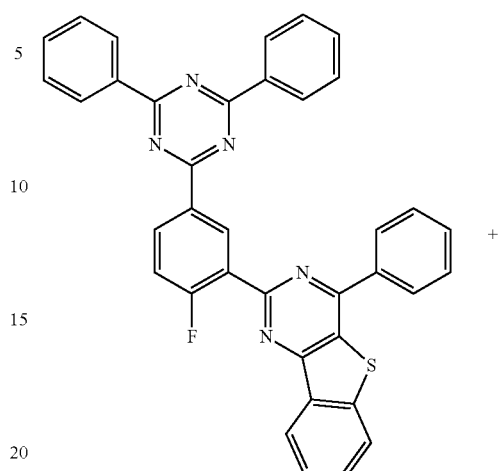

6-c

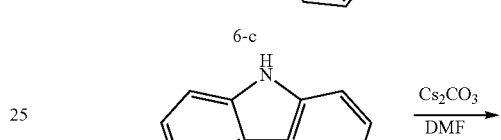

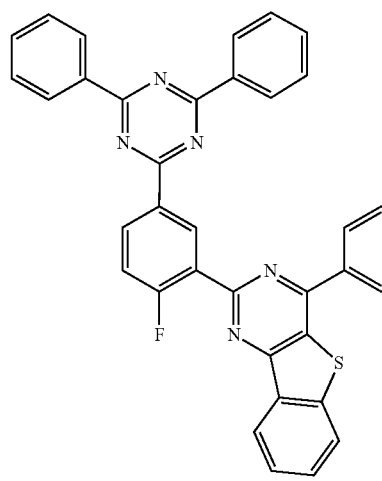

6-c

6

Compound 6-b (20 g, 44.1 mmol) and 2-chloro-4-phenylbenzo[4,5]thieno[3,2-d]pyrimidine (13.1 g, 44.1 mmol) were added to 400 ml of tetrahydrofuran under a nitrogen atmosphere, and the mixture was stirred and refluxed. Then, potassium carbonate (18.3 g, 132.4 mmol) was dissolved in 18 ml of water, added thereto and sufficiently stirred, and then tetrakistriphenyl-phosphinopalladium (1.5 g, 1.3 mmol) was added. After reaction for 3 hours, the reaction mixture was cooled to room temperature and then the produced solid was filtered. The solid was added to 519 mL of choloroform, dissolved and washed twice with water. The organic layer was then separated, anhydrous magnesium sulfate was added, stirred, and then filtered. The filtrate was distilled under reduced pressure. The concentrated compound was purified by recrystallization with chloroform and ethyl acetate to give a white solid 6-c (13 g, 50%, MS: [M+H]$^+$=588.7).

Compound 6-c (20 g, 34 mmol) and carbazole (5.7 g, 34 mmol) were added to 400 ml of dimethyl formamide under a nitrogen atmosphere, and the mixture was stirred and refluxed. Then, cesium carbonate (33.3 g, 102.1 mmol) was added thereto and the temperature was raised while stirring. After reaction for 3 hours, the reaction mixture was cooled to room temperature and then the organic layer was subjected to filtration treatment to remove a salt, and then the filtered organic layer was distilled. This was again added to 250 mL of chloroform, dissolved and washed twice with water. The organic layer was then separated, anhydrous magnesium sulfate was added, stirred, and then filtered. The filtrate was distilled under reduced pressure. The concentrated compound was purified by silica gel column chromatography and sublimation purification to give compound 6 (15.5 g, 62%, MS: [M+H]$^+$=735.9).

Preparation Example 7: Preparation of Compound 7

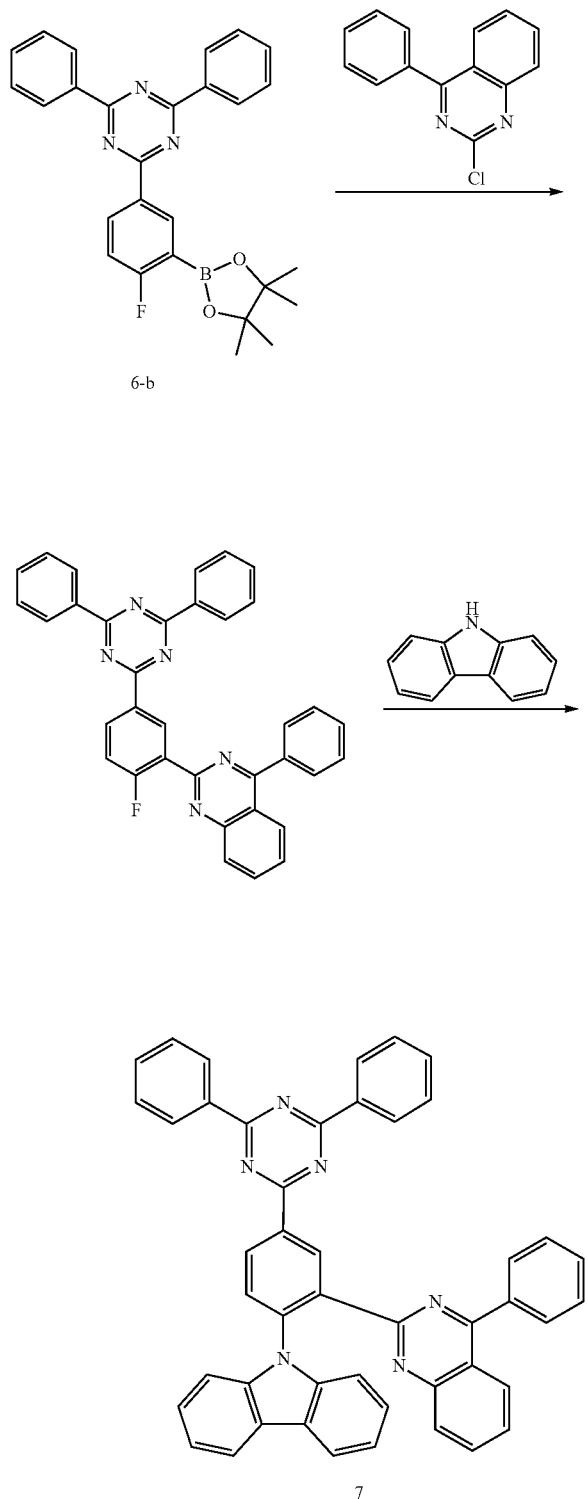

Compound 7 was prepared in the same manner as the preparation method of Compound 6, except that 2-chloro-4-phenylquinazoline was used instead of 2-chloro-4-phenyl-benzo[4,5]thieno[3,2-d]pyrimidine in Step 3 of Preparation Example 6 (MS [M+H]$^+$=679.8).

Preparation Example 8: Preparation of Compound 8

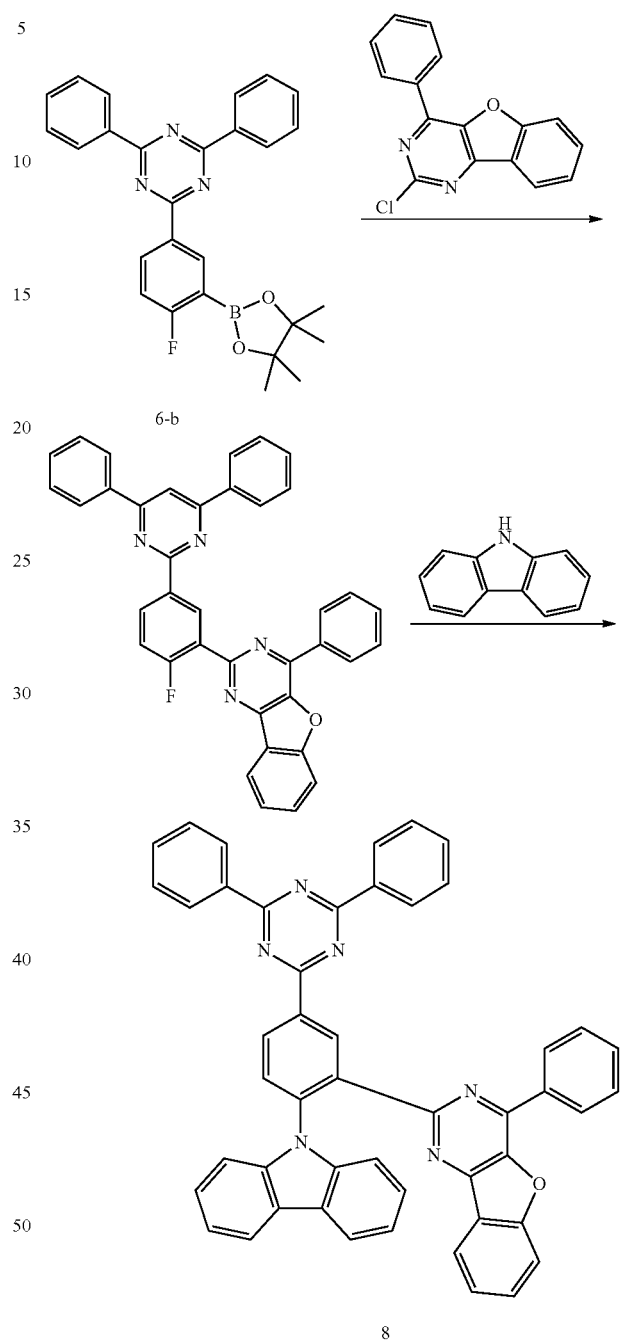

Compound 8 was prepared in the same manner as the preparation method of Compound 6, except that 2-chloro-4-phenylbenzofuro[3,2-d]pyrimidine was used instead of 2-chloro-4-phenylbenzo[4,5]thieno[3,2-d]pyrimidine in Step 3 of Preparation Example 6 (MS [M+H]$^+$=719.8).

EXAMPLES

Example 1

A glass substrate on which ITO (indium tin oxide) was coated as a thin film to a thickness of 1400 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, a compound HT-A and a compound PD below were thermally vacuum-deposited to a thickness of 100 Å in a weight ratio of 95:5, and then the compound HT-A was deposited to a thickness of 1150 Å to form a hole transport layer. A compound HT-B below was thermally vacuum-deposited to a thickness of 450 Å on the hole transport layer to form an electron blocking layer. Compound 1 prepared in the previous preparation example and a compound GD below were deposited in a weight ratio of 85:15 on the electron blocking layer with a thickness of 400 Å to form a light emitting layer. A compound ET-A below was vacuum-deposited to a thickness of 50 Å on the light emitting layer to form a hole blocking layer. A compound ET-B and a compound Liq below were thermally vacuum-deposited in a weight ratio of 2:1 on the hole blocking layer with a thickness of 250 Å, and then LiF and magnesium were vacuum-deposited in a weight ratio of 1:1 with a thickness of 30 Å to form an electron transport and injection layer. Magnesium and silver were deposited to a thickness of 160 Å in a weight ratio of 1:4 on the electron transport and injection layer to form a cathode, to prepare an organic emitting device.

-continued

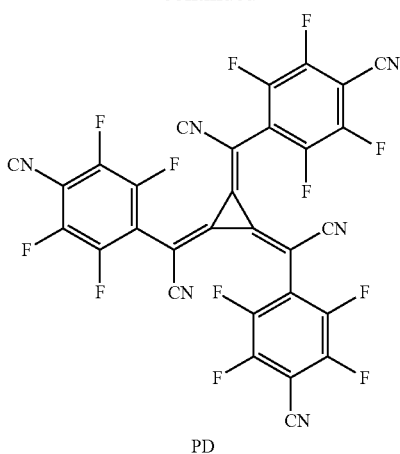

PD

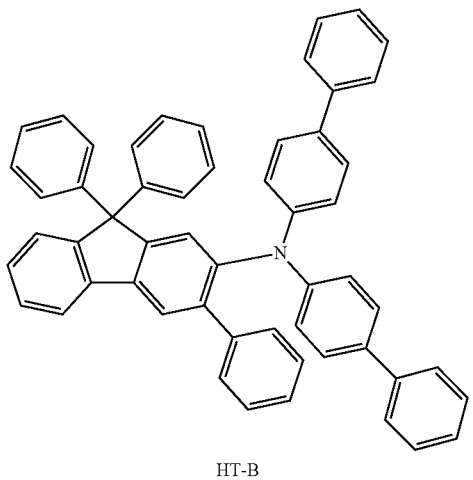

HT-B

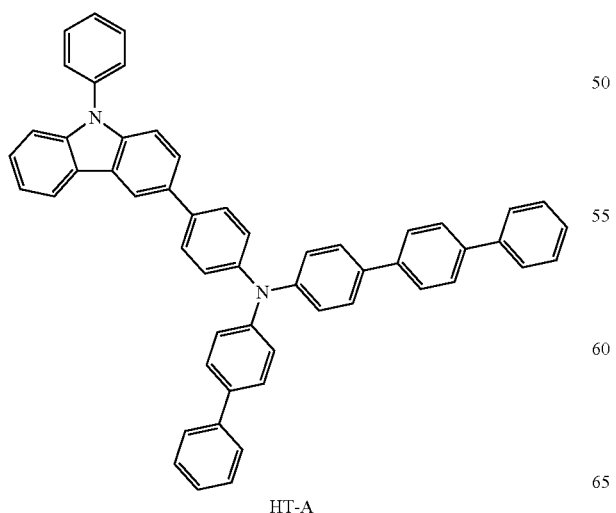

HT-A

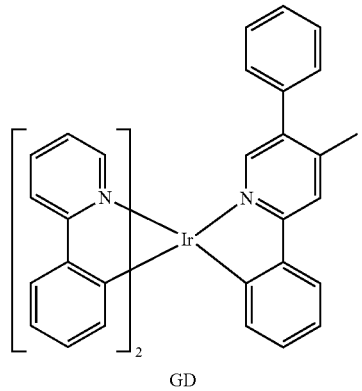

GD

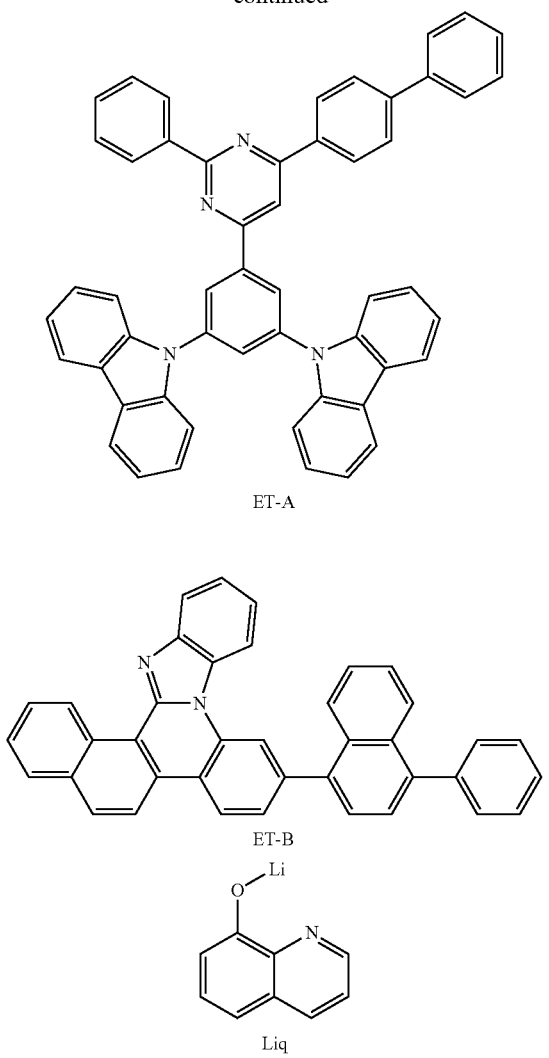

ET-A

ET-B

Liq

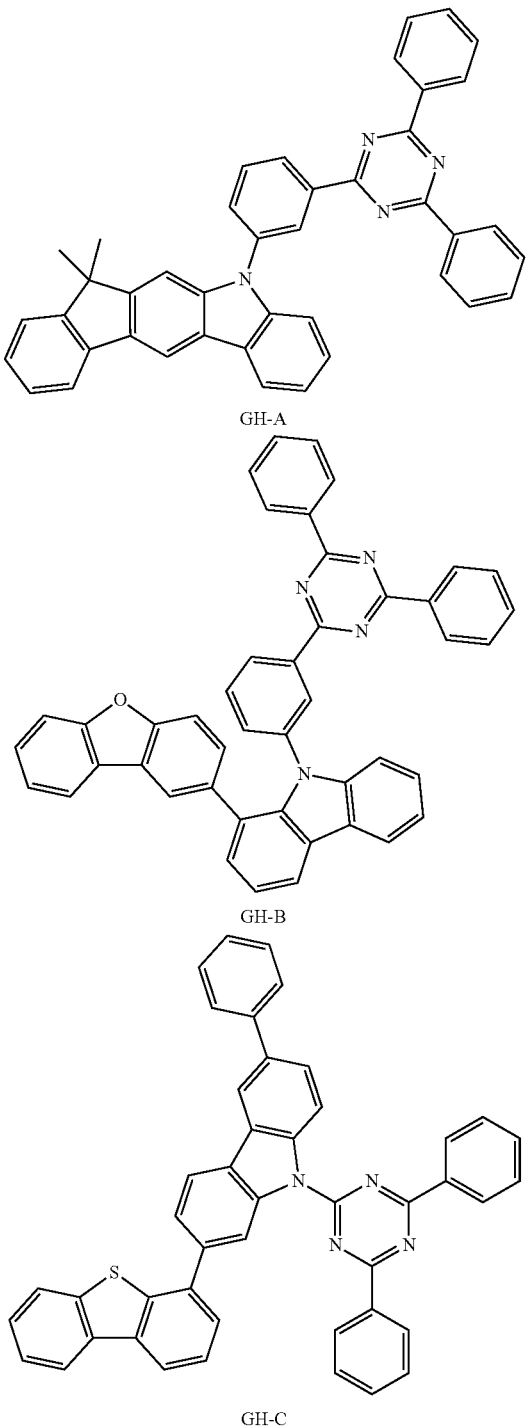

GH-A

GH-B

GH-C

In the above-mentioned process, the vapor deposition rate of the organic material was maintained at 0.4~0.7 Å/sec, the deposition rate of lithium fluoride of anode was maintained at 0.3 Å/sec, the deposition rate of silver and magnesium was maintained at 2 Å/sec, and the degree of vacuum during the deposition was maintained $2\times10^{-7}$ to $5\times10^{-6}$ torr to form an organic light emitting device.

Examples 2 to 8

The organic light emitting devices were manufactured in the same manner as in Example 1, except that the compounds shown in Table 1 below were used instead of Compound 1.

Comparative Examples 1 to 3

The organic light emitting devices were manufactured in the same manner as in Example 1, except that the compounds shown in Table 1 below were used instead of Compound 1. In Table 1, the compounds GH-A, GH-B and GH-C are as follows.

Experimental Example

The voltage, efficiency, and lifetime (T95) of the organic light emitting devices manufactured in the examples and comparative examples were measured by applying current, and the results are shown in Table 1 below. At this time, the voltage and efficiency were measured at a current density of 10 mA/cm². Further, the T95 means the time required for the luminance to be reduced to 95% of the initial luminance at a current density of 20 mA/cm².

TABLE 1

| | Light emitting layer (host) | Voltage (V) | Efficiency (cd/A) | Lifetime (T95, hr) |
|---|---|---|---|---|
| Example 1 | compound 1 | 4.98 | 38.2 | 83 |
| Example 2 | compound 2 | 5.03 | 36.2 | 92 |
| Example 3 | compound 3 | 4.95 | 37.1 | 82 |
| Example 4 | compound 4 | 4.97 | 38.3 | 93 |
| Example 5 | compound 5 | 5.09 | 36.1 | 71 |
| Example 6 | compound 6 | 5.05 | 36.9 | 83 |
| Example 7 | compound 7 | 5.11 | 37.3 | 82 |
| Example 8 | compound 8 | 5.19 | 37.6 | 85 |
| Comparative Example 1 | GH-A | 5.12 | 33.2 | 43 |
| Comparative Example 2 | GH-B | 5.21 | 33.8 | 56 |
| Comparative Example 3 | GH-C | 6.12 | 27.5 | 50 |

In the compound represented by Chemical Formula 1 and 2, an intra charge transfer can be easily occur since a carbazole group having hole transferring characteristics is in ortho position with triazine, benzothienopyrimidine, quinazoline, or benzofuropyrimidine, which have electron transferring characteristics. Thus, molecular stability is high and the compound is advantageous for both hole and electron transport. In addition, the electron transport characteristics may be adjusted variously with the combination of $Ar_1$, $Ar_2$, and E of Chemical Formula 1 or 2, and therefore the compound is advantageous in balancing charges in accordance with change of the common layer.

Therefore, as shown in Table 1, when the compound represented by Chemical Formula 1 or 2 was used as a host material of organic light emitting device, it was confirmed that it exhibited low driving voltage, high efficiency, and long lifetime characteristics as compared with Comparative Examples having similar molecular structure.

<Description of Reference Numerals>

| | |
|---|---|
| 1: substrate | 2: anode |
| 3: organic material layer | 4: cathode |
| 5: hole injection layer | 6: hole transport layer |
| 7: electron blocking layer | 8: light emitting layer |
| 9: hole blocking layer | 10: electron transport layer |
| 11: electron injection layer | |

The invention claimed is:

1. A compound represented by Chemical Formula 1 or 2:

[Chemical Formula 1]

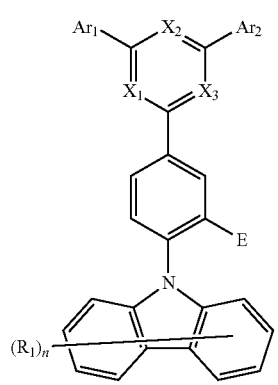

[Chemical Formula 2]

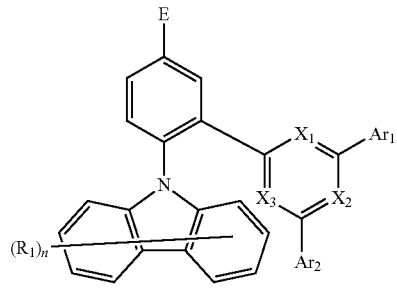

wherein, in Chemical Formulas 1 and 2, $X_1$ to $X_3$ are each independently, CH or N, and at least one of $X_1$ to $X_3$ is N, $Ar_1$ and $Ar_2$ are each independently a substituted or unsubstituted $C_{6-60}$ aryl; or a substituted or unsubstituted $C_{2-60}$ heteroaryl containing at least one heteroatom selected from the group consisting of N, O, and S, $R_1$ is each independently deuterium; a substituted or unsubstituted $C_{6-60}$ aryl; or a substituted or unsubstituted $C_{2-60}$ heteroaryl containing at least one heteroatom selected from the group consisting of N, O, and S, n is an integer of 0 to 8, E is a substituent represented by Chemical Formula 3-1 or 3-2,

[Chemical Formula 3-1]

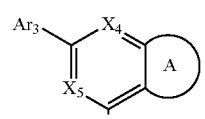

[Chemical Formula 3-2]

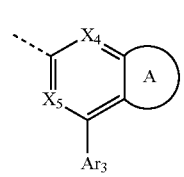

wherein, in Chemical Formulas 3-1 and 3-2, $X_4$ and $X_5$ are each independently, CH or N, and at least one of $X_4$ and $X_5$ is N, $Ar_3$ is a substituted or unsubstituted $C_{6-60}$ aryl; or a substituted or unsubstituted $C_{2-60}$ heteroaryl containing at least one heteroatom selected from the group consisting of N, O, and S, wherein A is represented by Chemical Formula 4-1 or 4-2,

[Chemical Formula 4-1]

[Chemical Formula 4-2]

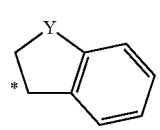

wherein, in Chemical Formulas 4-1 and 4-2,

* Is a bond shared with an adjacent hexagonal ring,

Y is O, S, C(R')₂, or NR',

R' is each independently hydrogen; deuterium; a substituted or unsubstituted $C_{6-60}$ aryl; or a substituted or unsubstituted $C_{2-60}$ heteroaryl containing at least one heteroatom selected from the group consisting of N, O, and S.

2. The compound of claim 1, wherein $R_1$ is phenyl.

3. The compound of claim 1, wherein all of $X_1$ to $X_3$ are N.

4. The compound of claim 1, wherein

E is any one selected from the group consisting of the following:

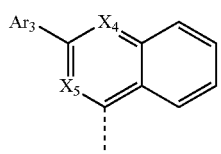 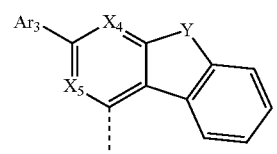

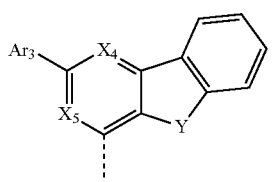 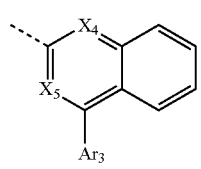

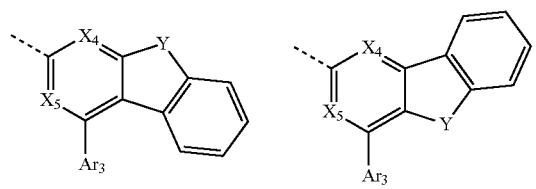

wherein, $Ar_3$, $X_4$, $X_5$, and Y are the same as those defined in claim 1.

5. The compound of claim 1, wherein both $X_4$ and $X_5$ are N.

6. The compound of claim 1, wherein

Y is O or S.

7. The compound of claim 1, wherein $Ar_1$ to $Ar_3$ are each independently phenyl, biphenyl, phenyl substituted with five deuteriums, or dibenzofuranyl.

8. The compound of claim 1, wherein the compound is any one selected from the group consisting of the following:

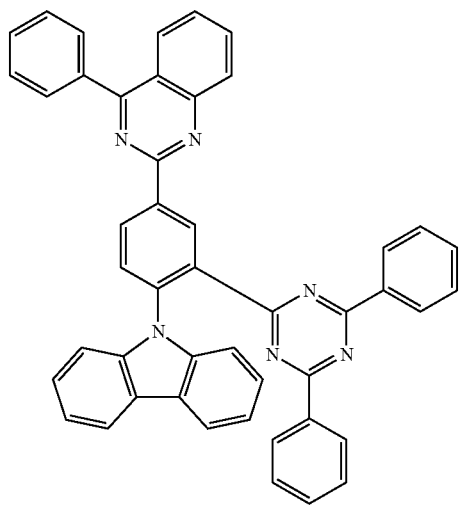

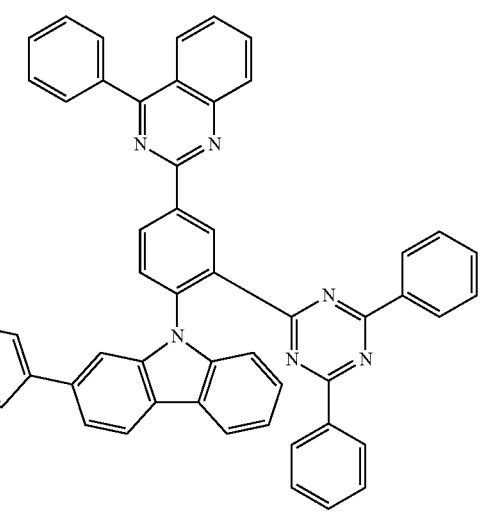

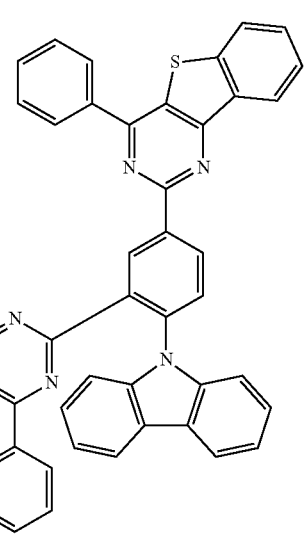

69
-continued
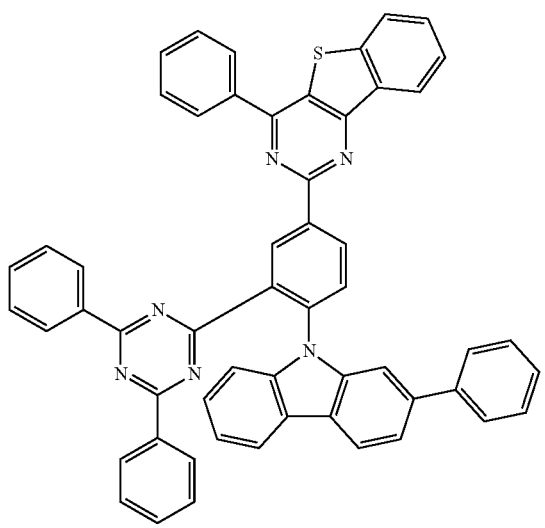
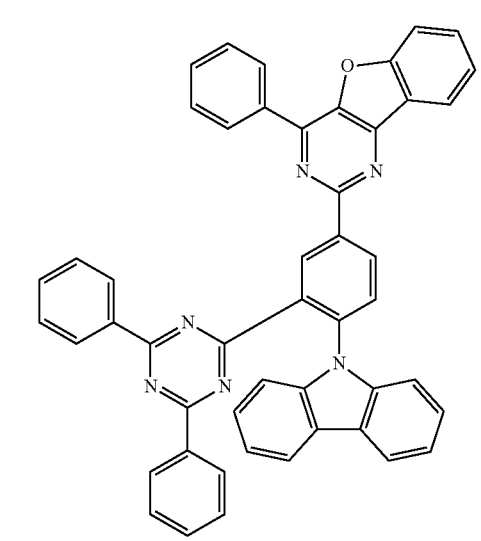
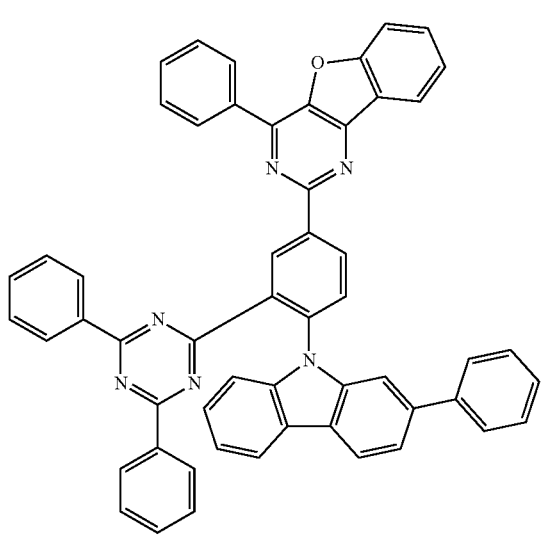
70
-continued
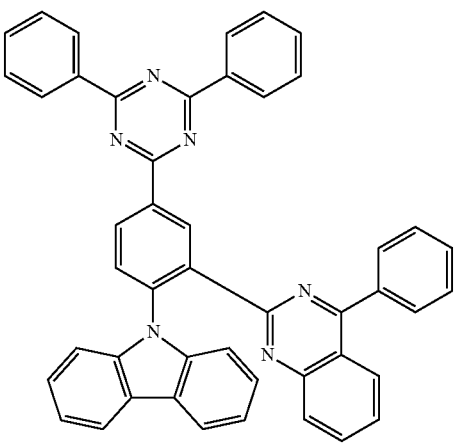
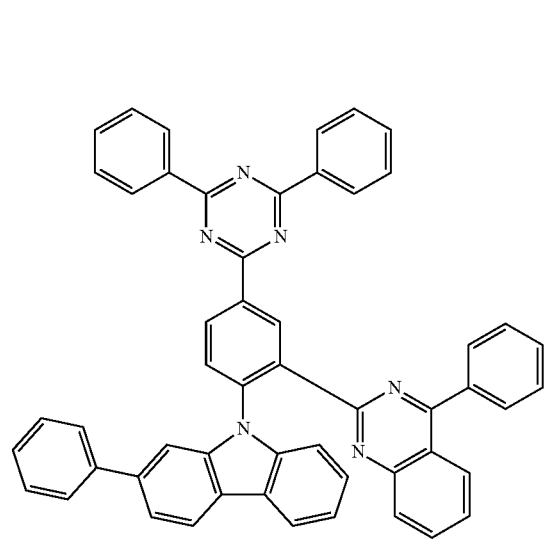
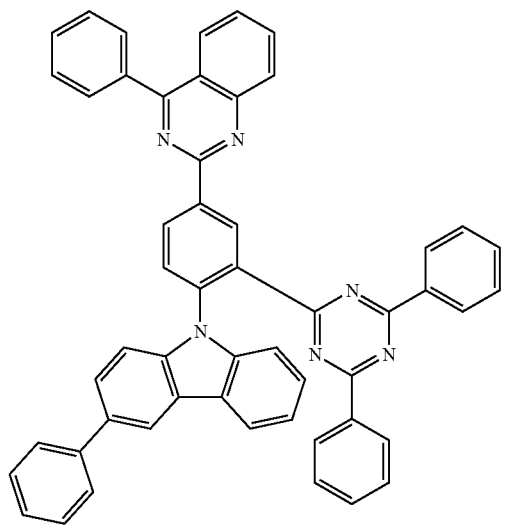

71
-continued
72
-continued
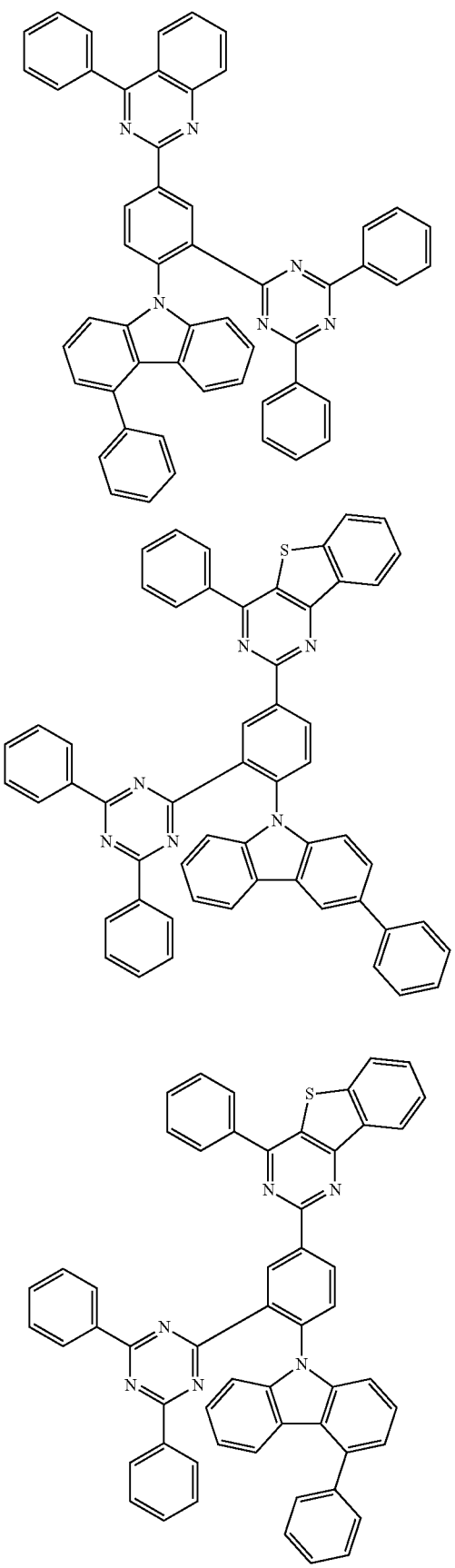
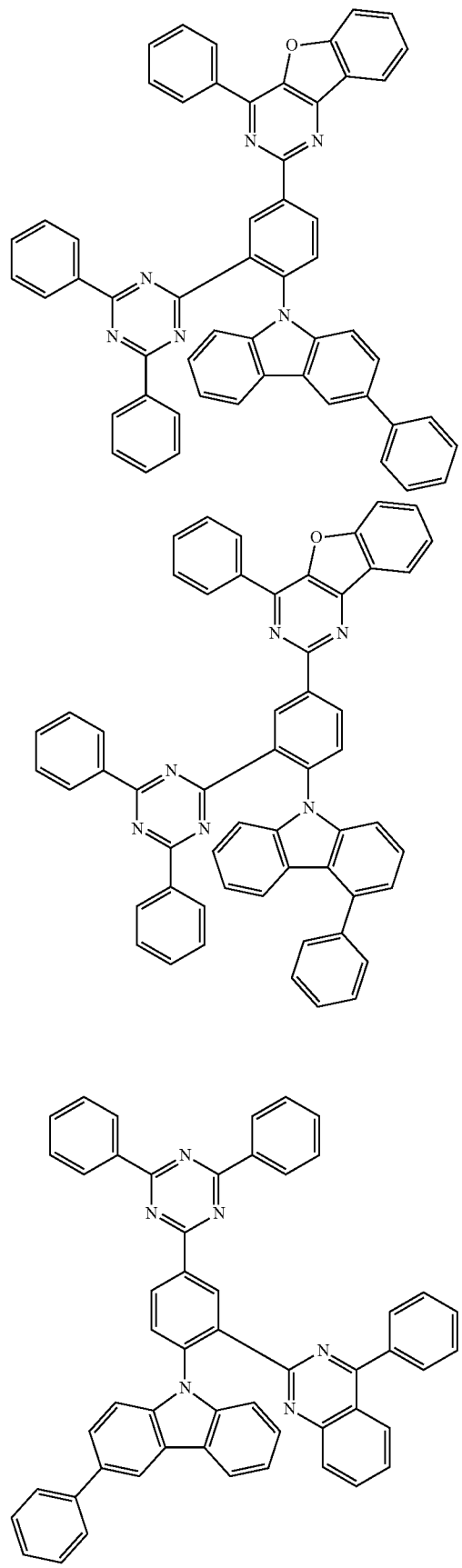

73
-continued
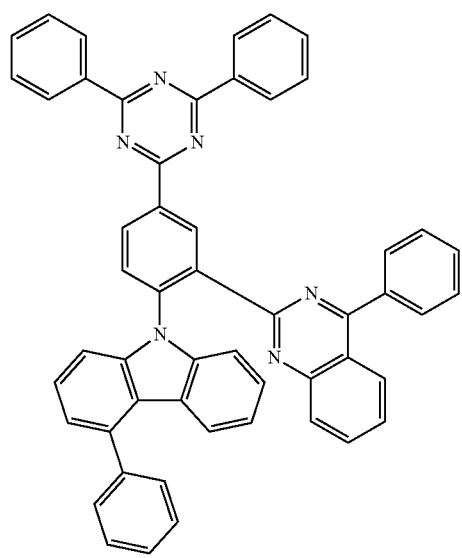
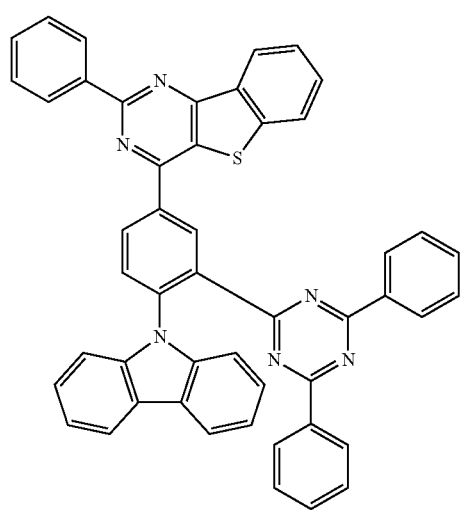
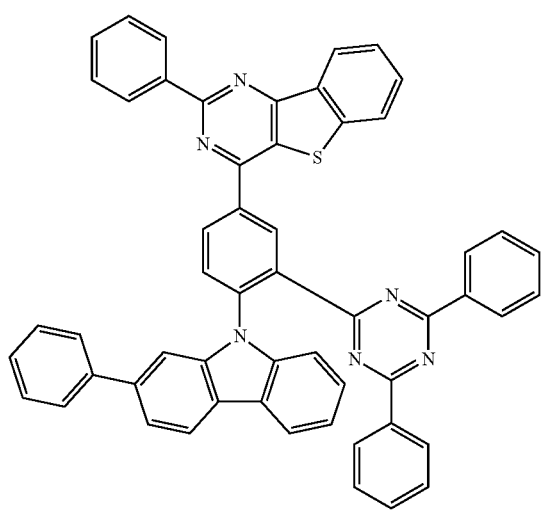
74
-continued
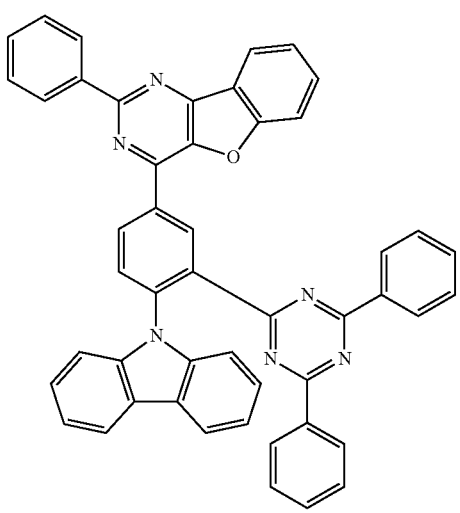
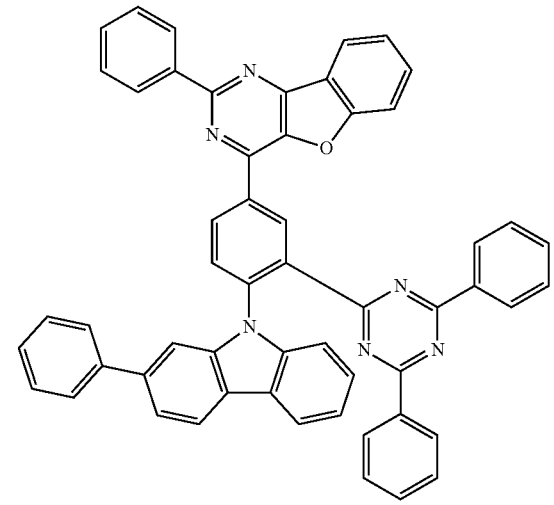
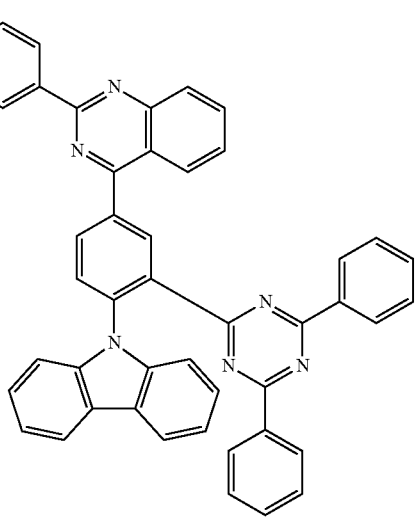

75
-continued
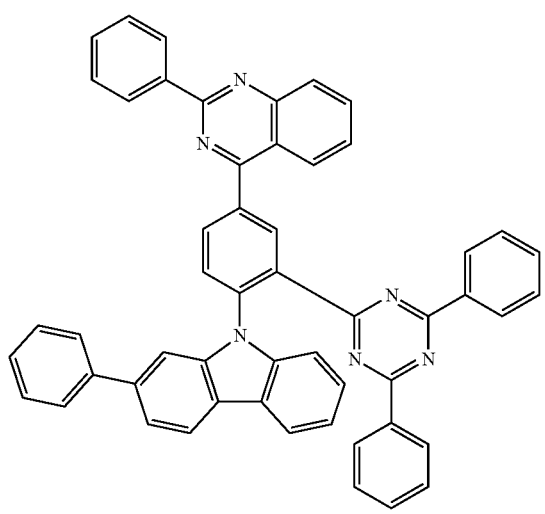
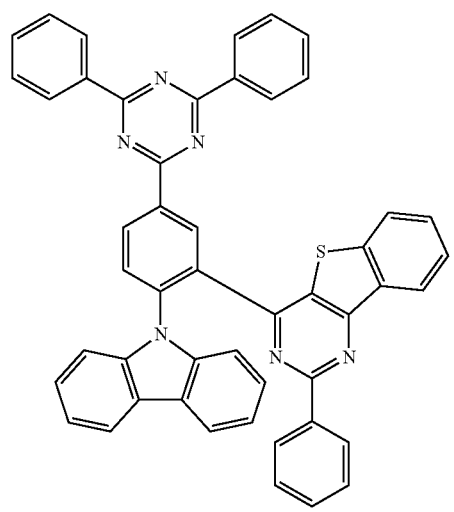
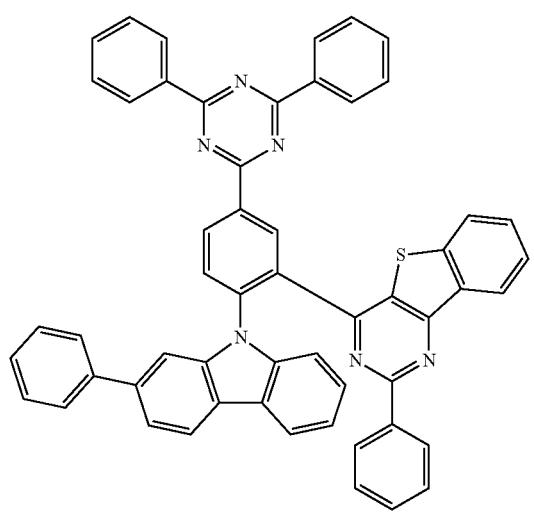
76
-continued
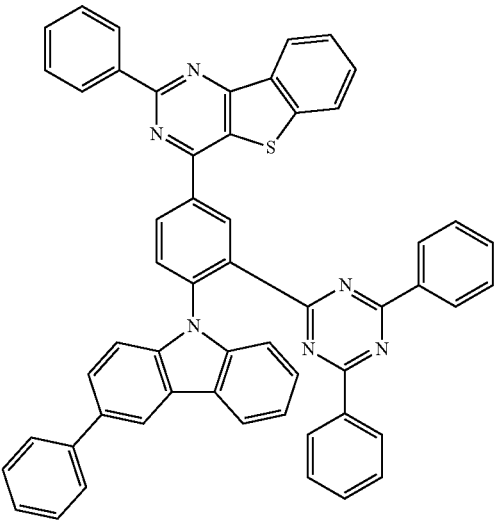
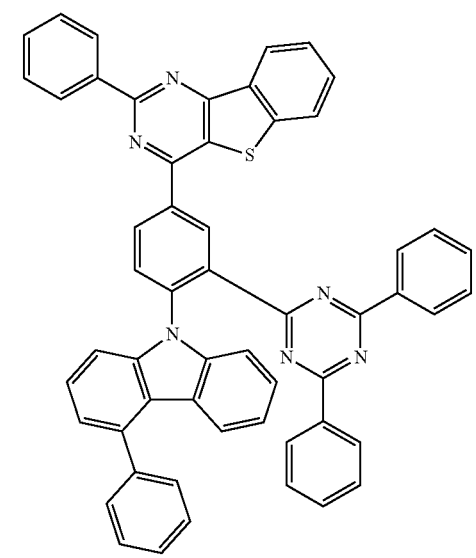
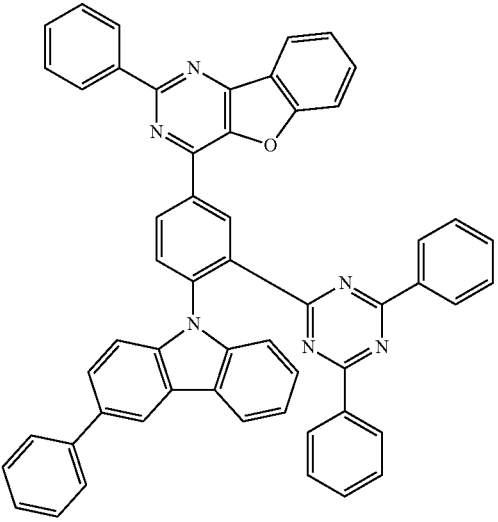

77
-continued
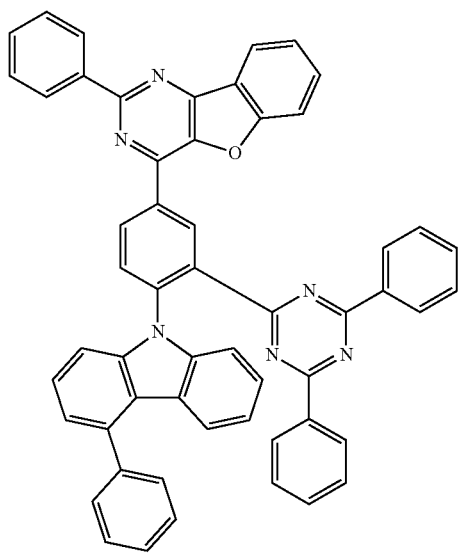
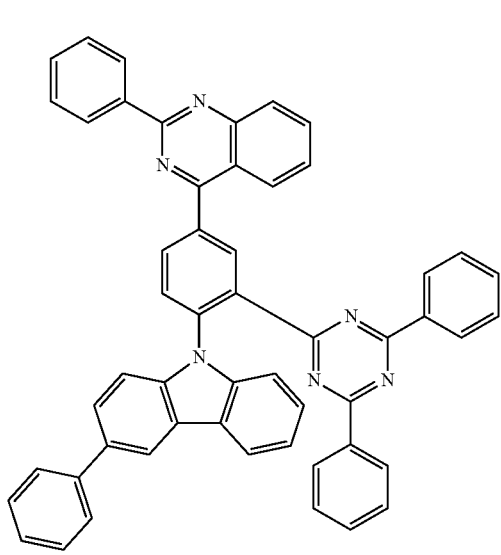
78
-continued
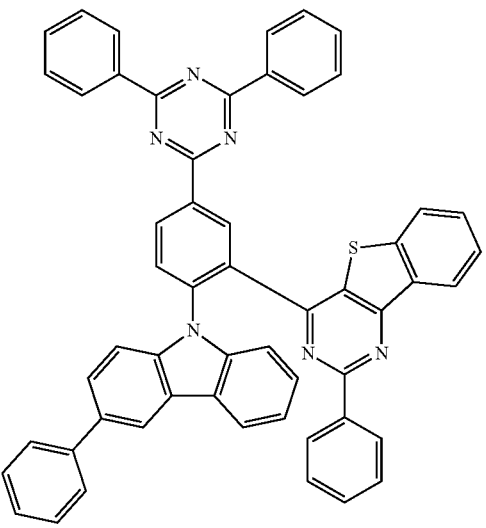
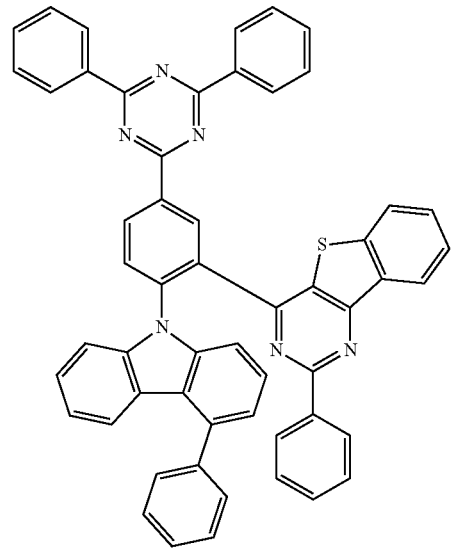
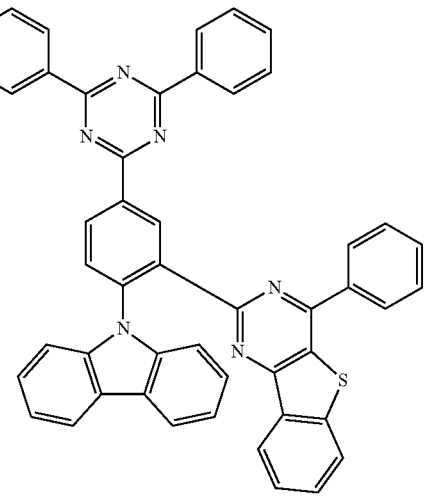

79
-continued
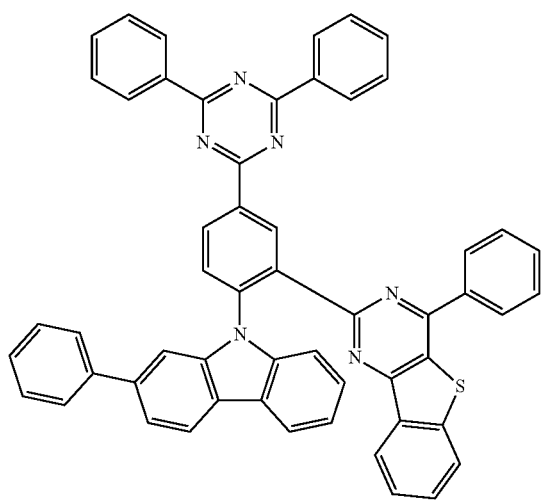
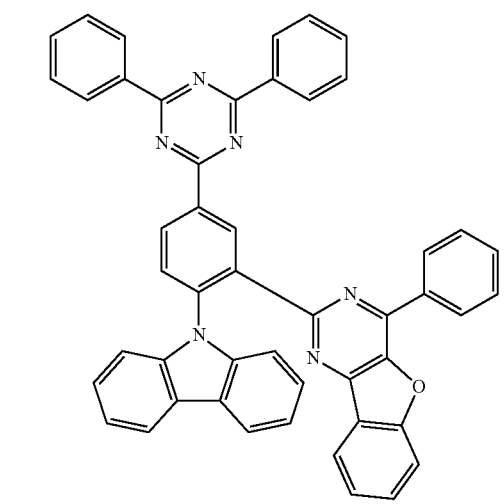
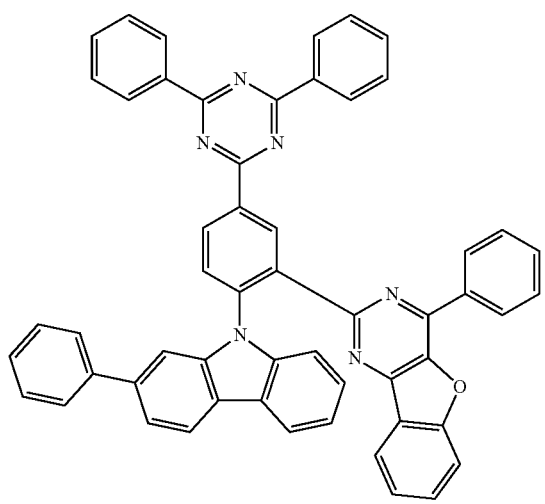
80
-continued
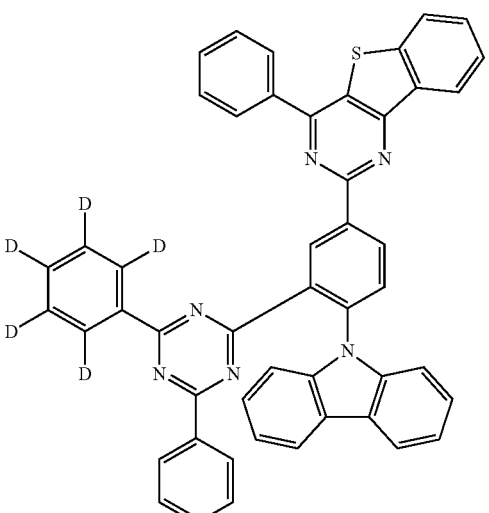
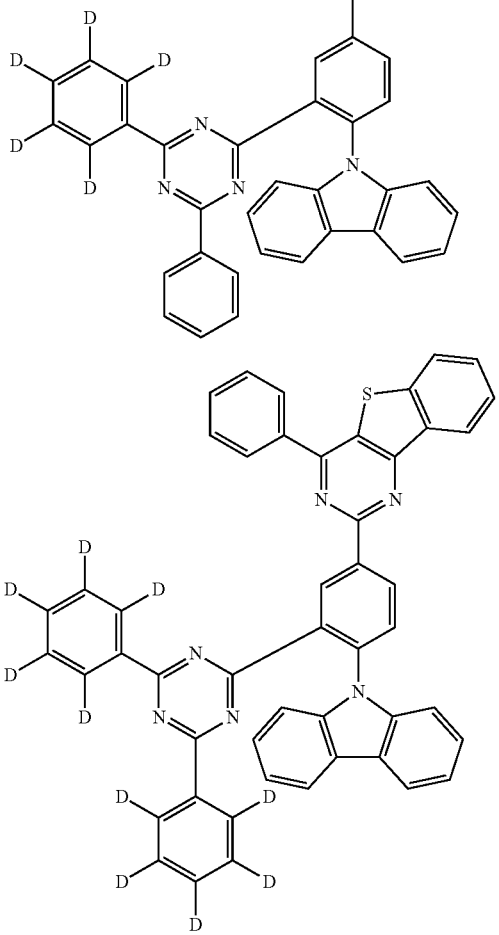
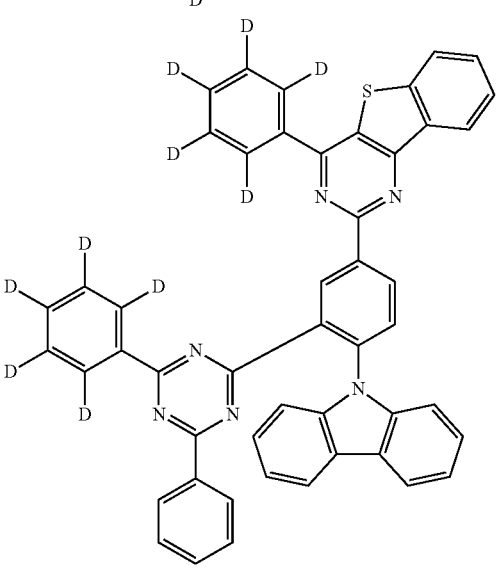

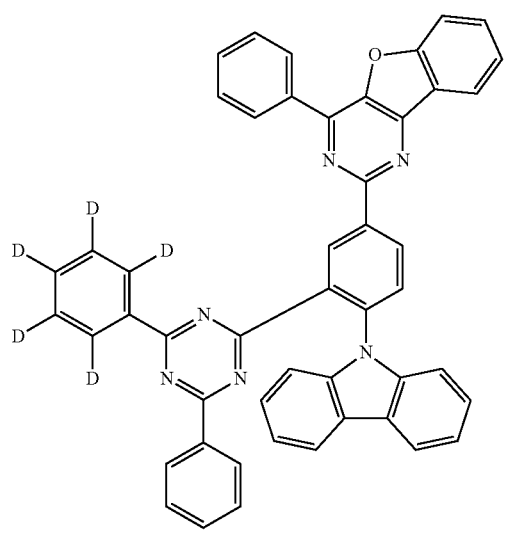
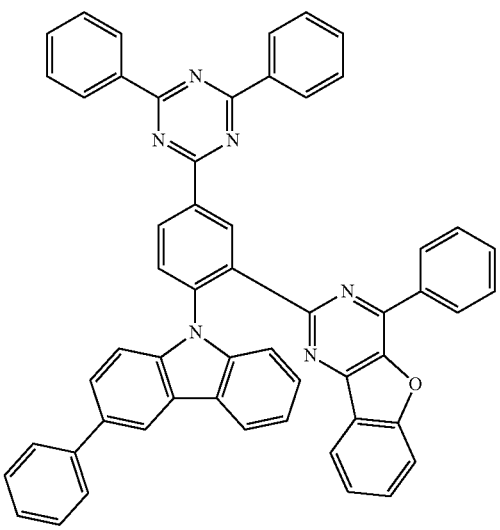
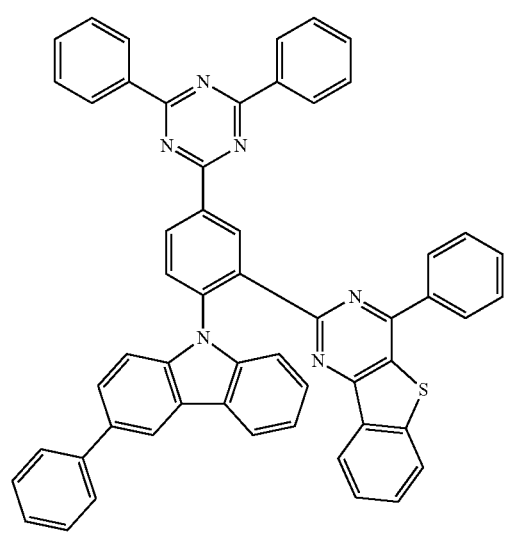
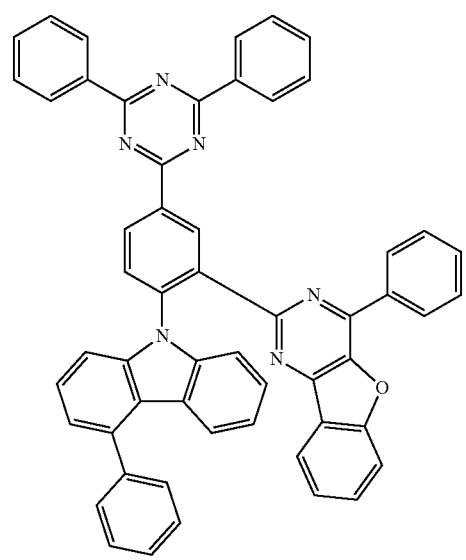
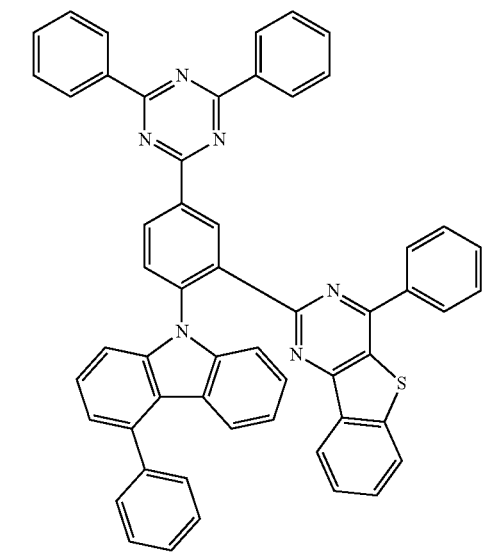
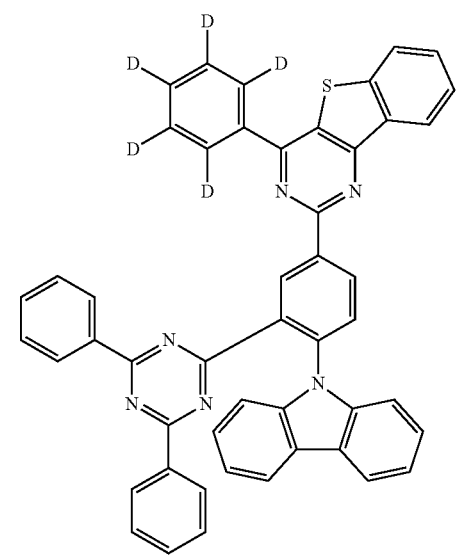

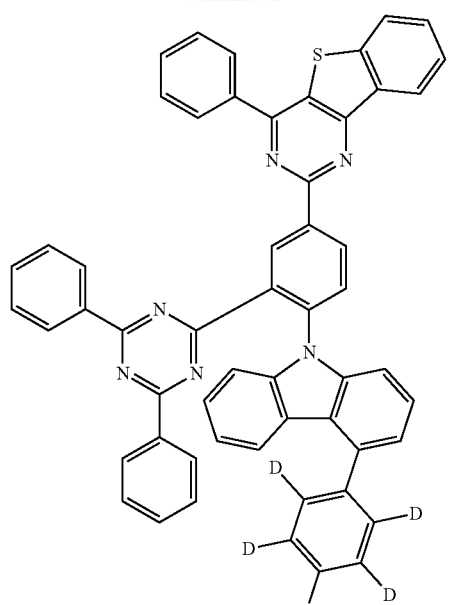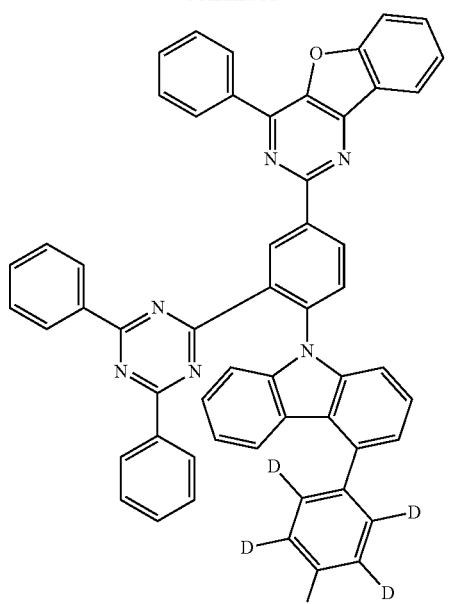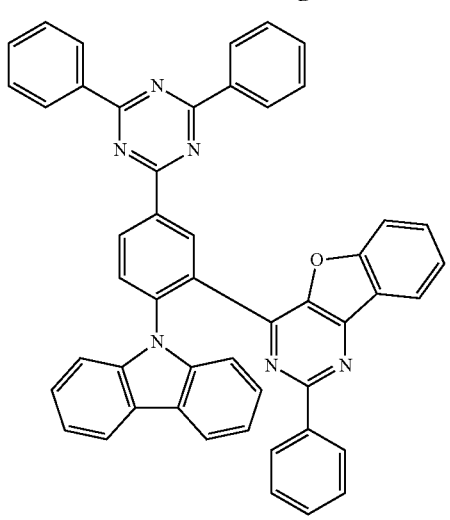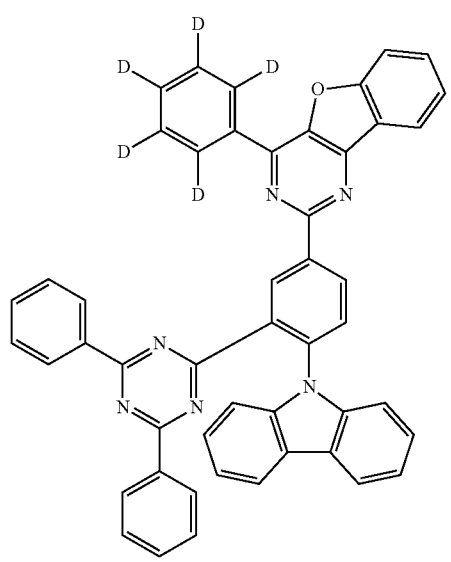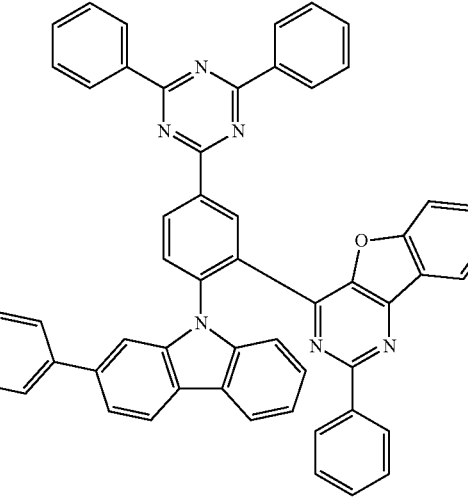

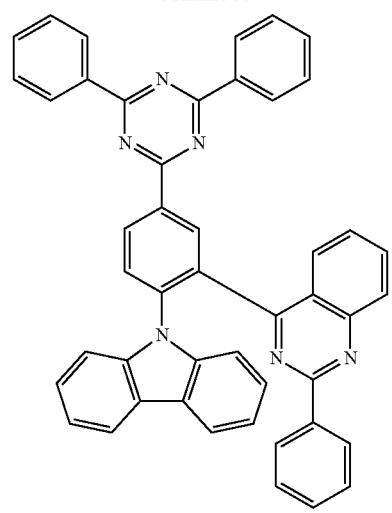
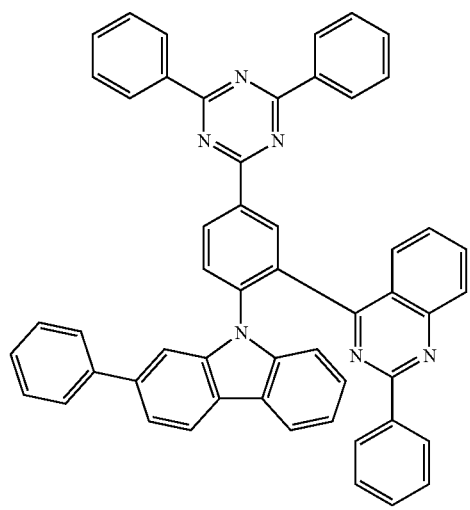
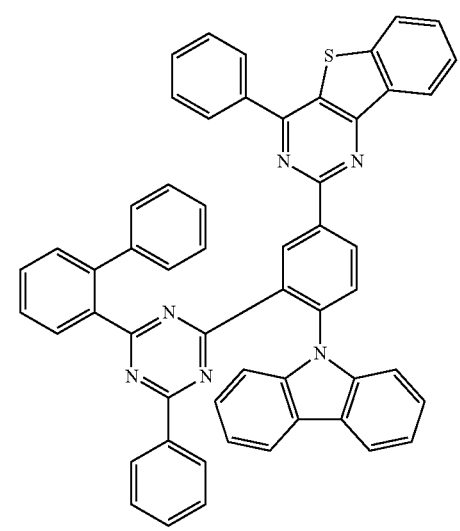
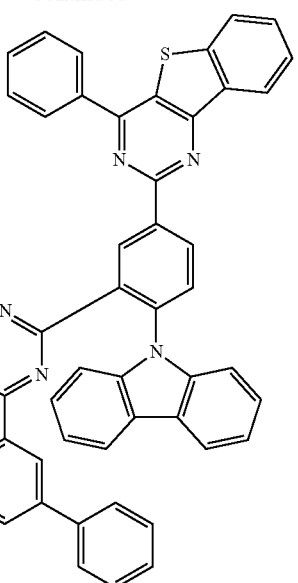
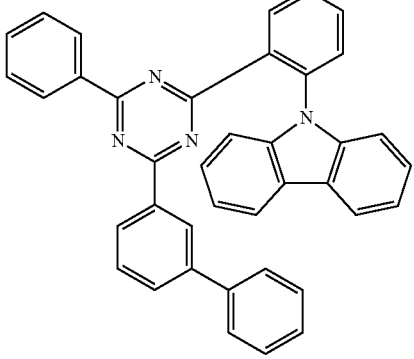
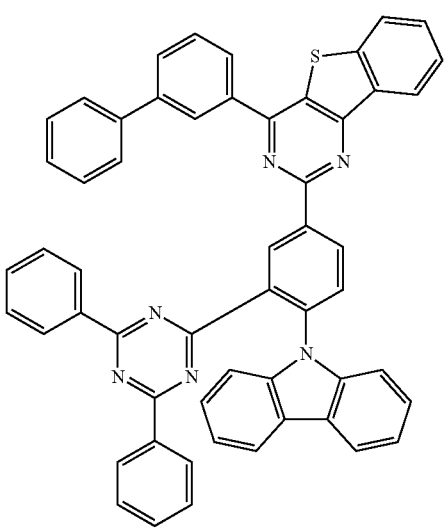
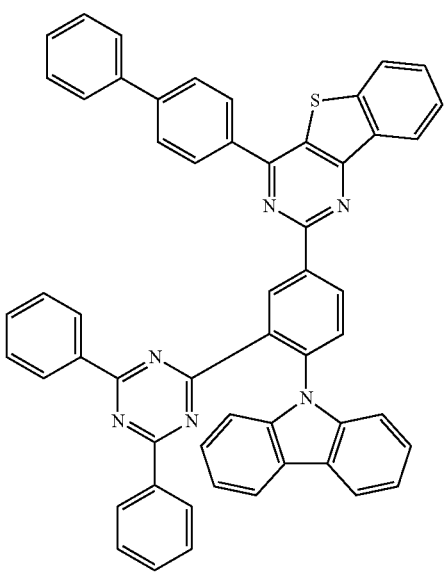

87
-continued
88
-continued
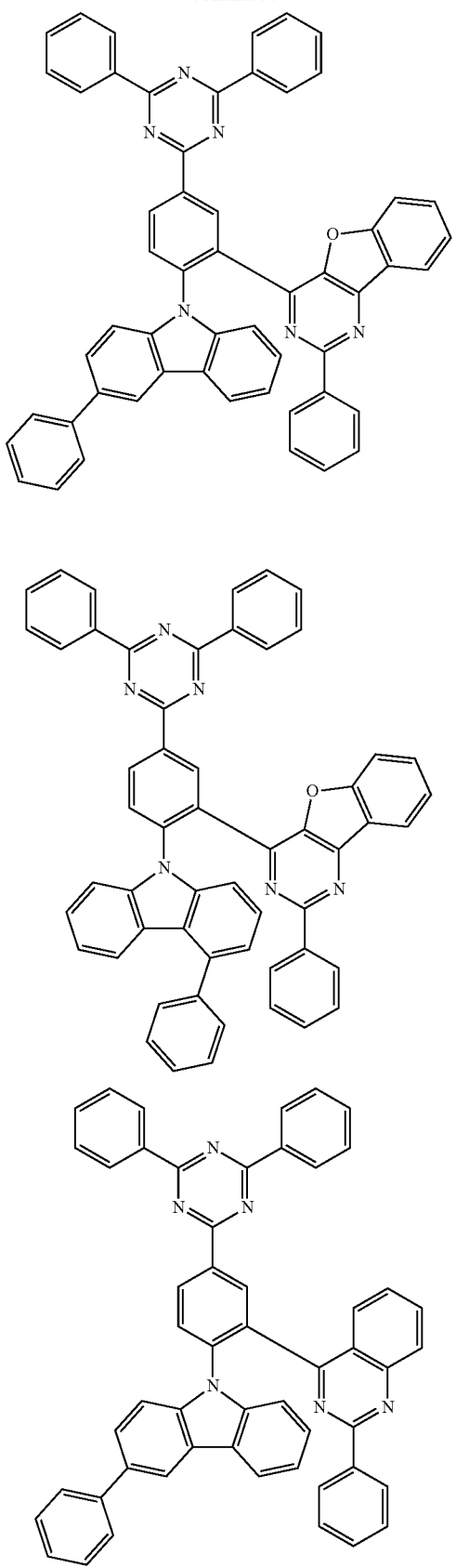
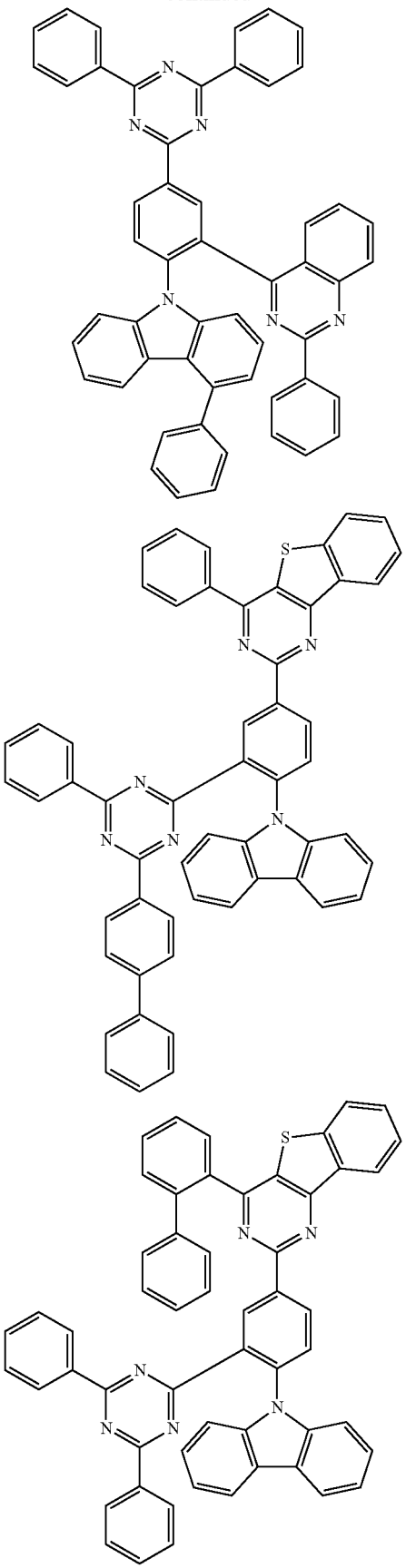

89
-continued
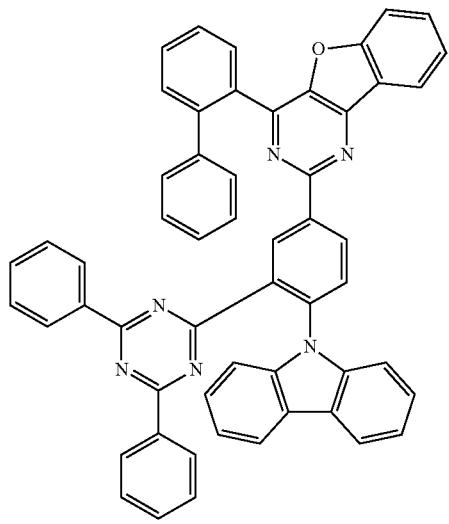
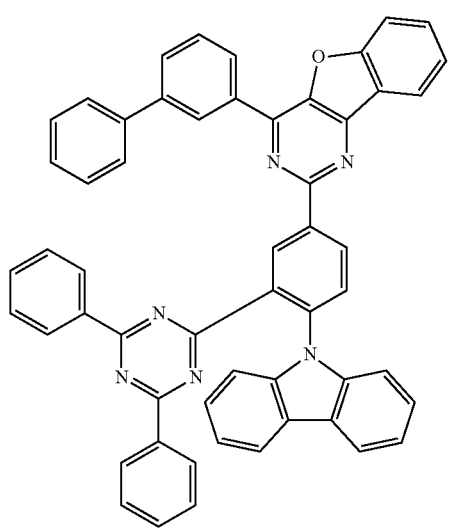
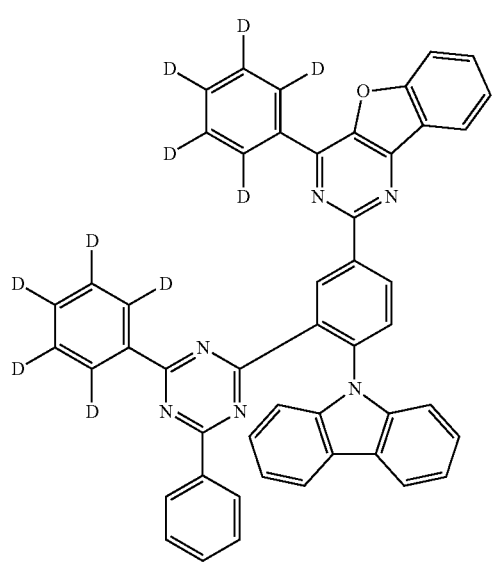
90
-continued
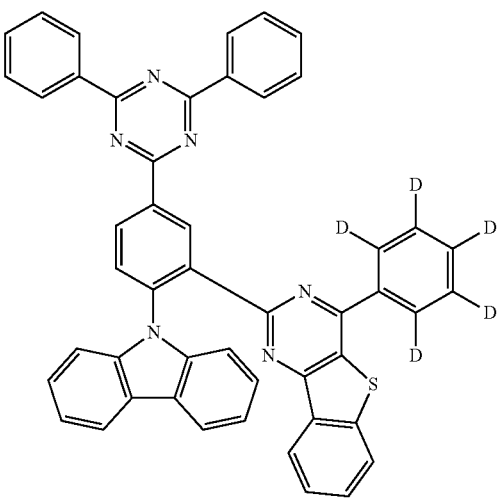
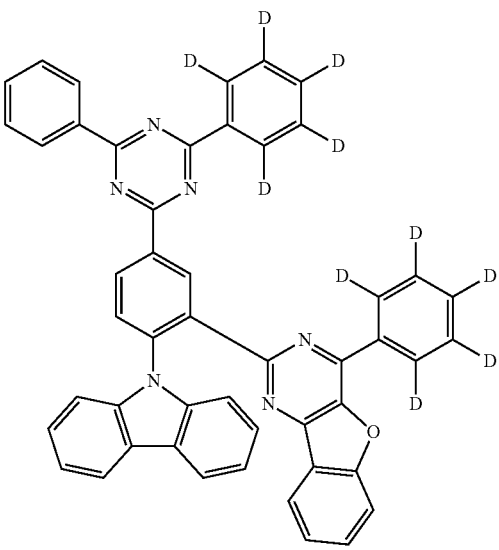

91
-continued
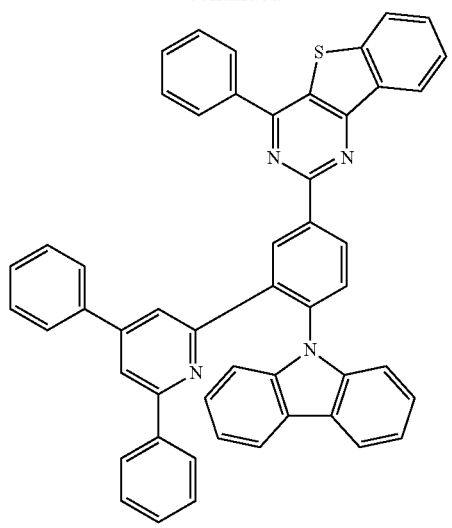
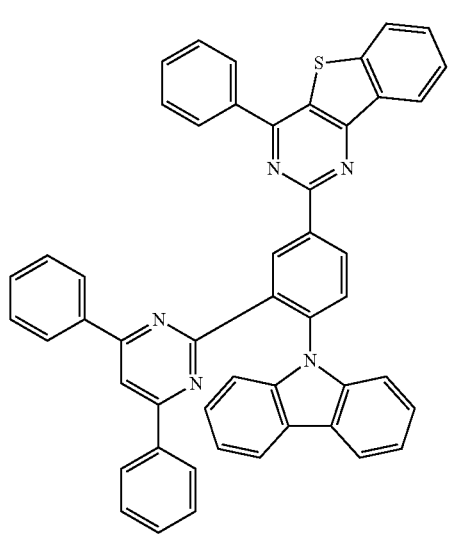
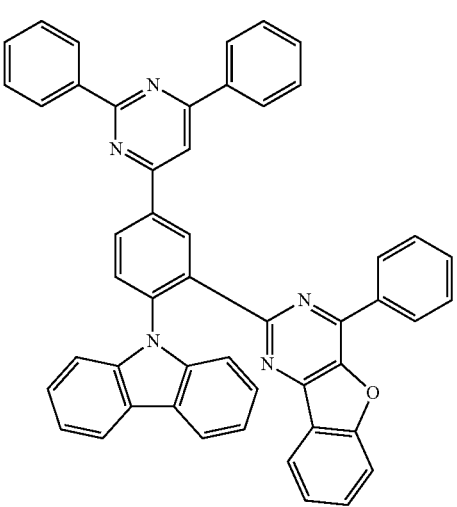
92
-continued
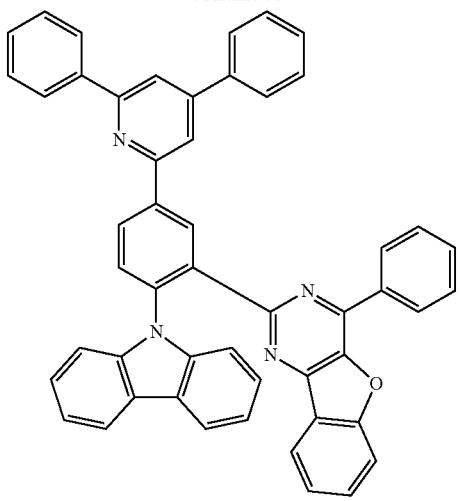
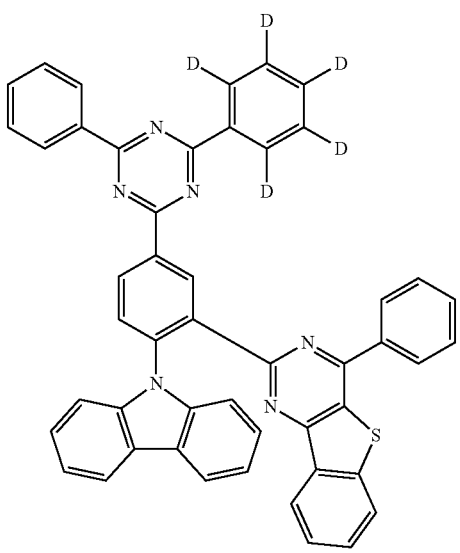
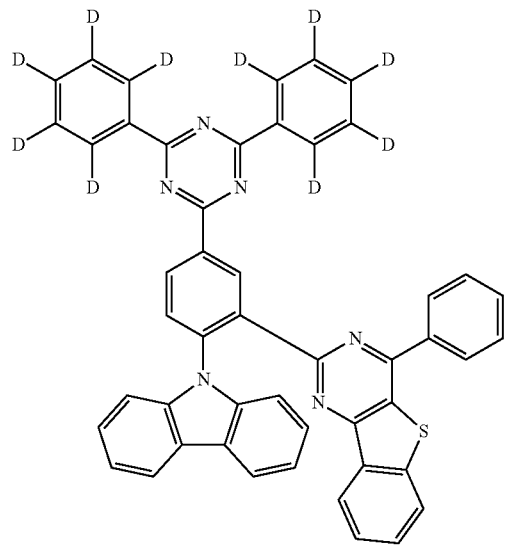

93
-continued
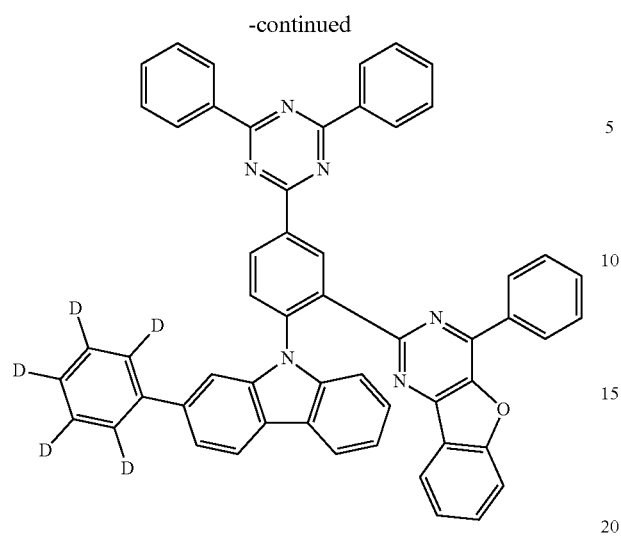
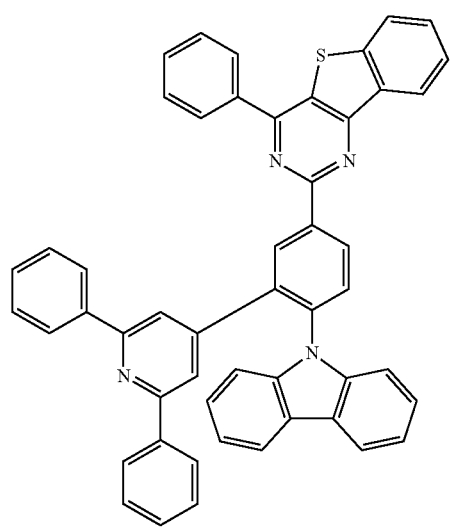
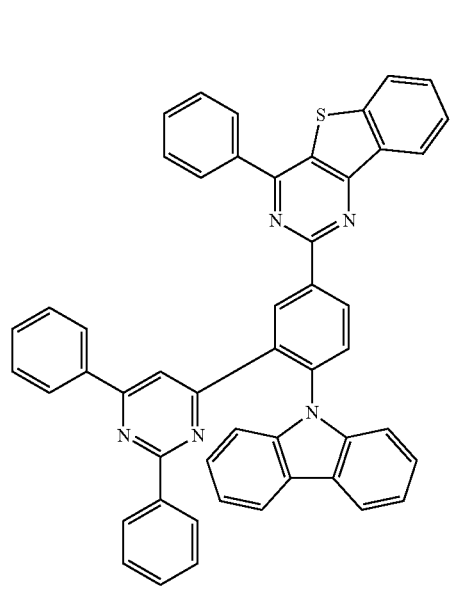
94
-continued
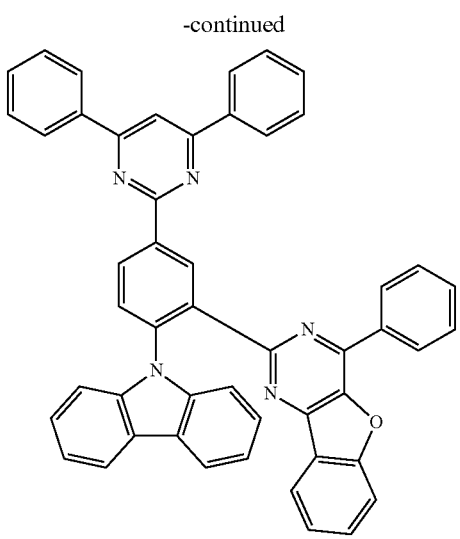
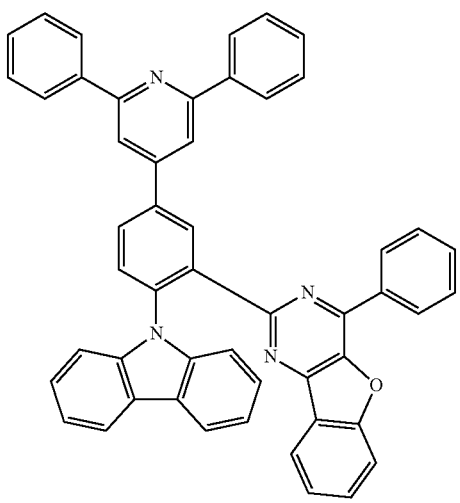
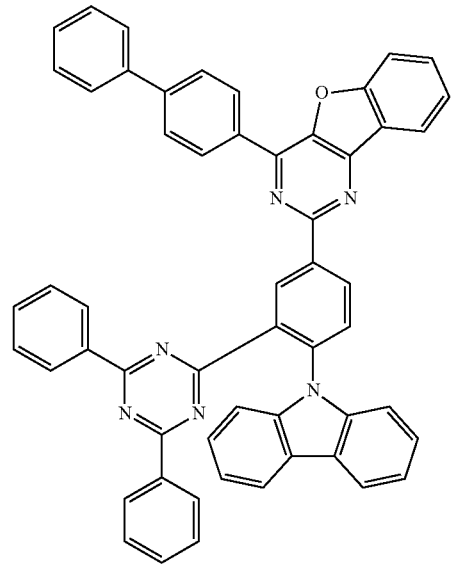

95
-continued
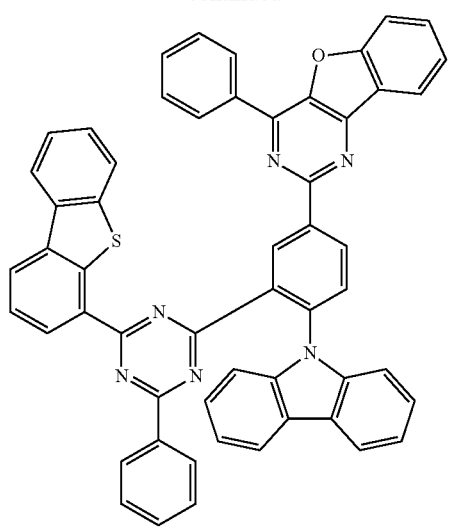
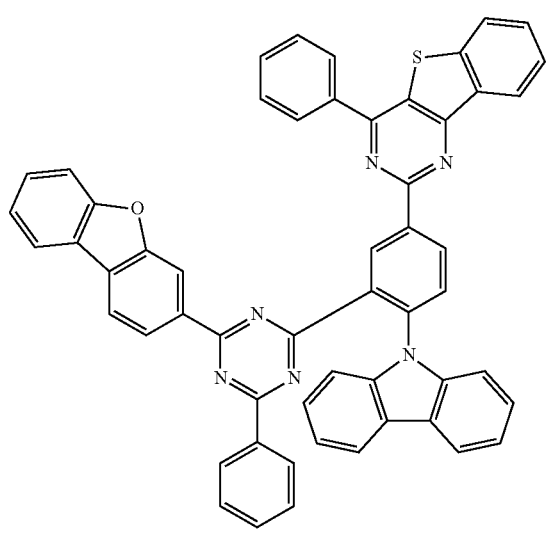
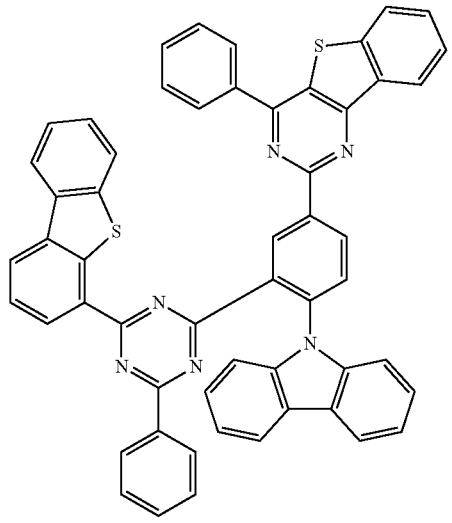
96
-continued
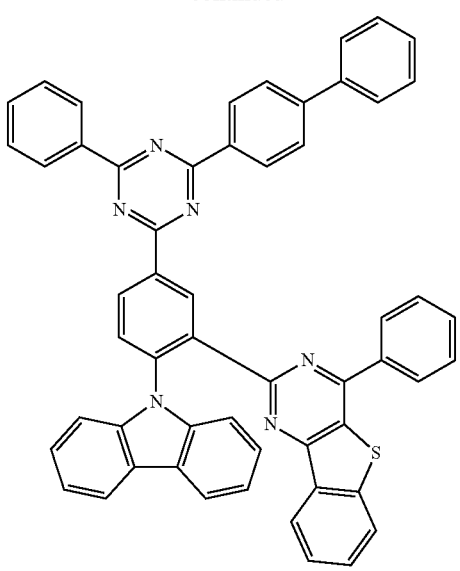
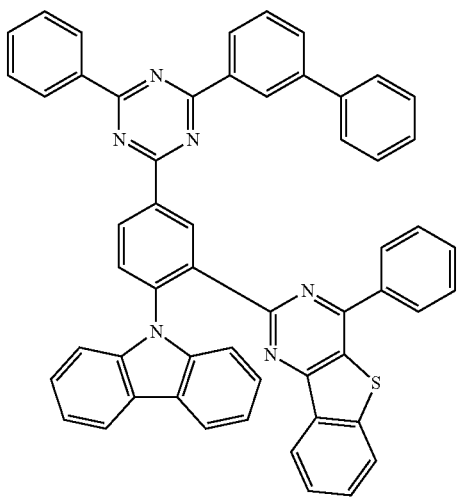
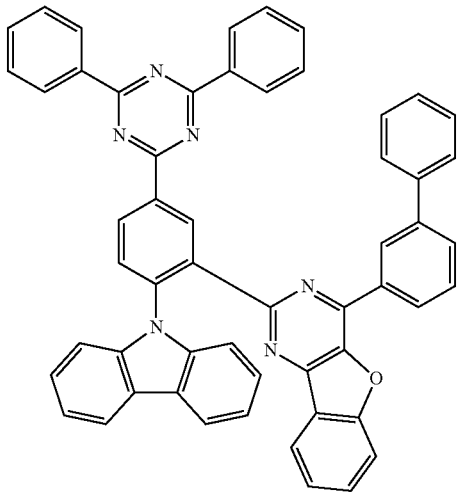

97
-continued
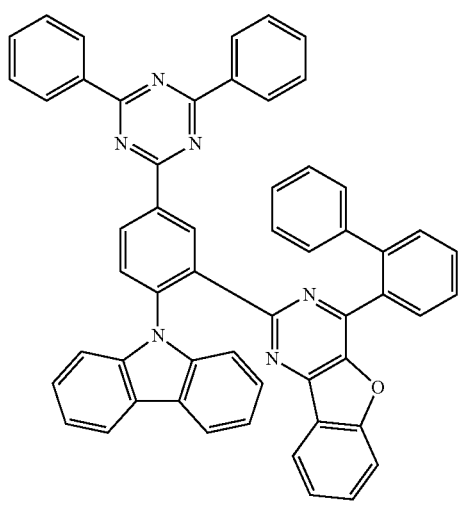
98
-continued
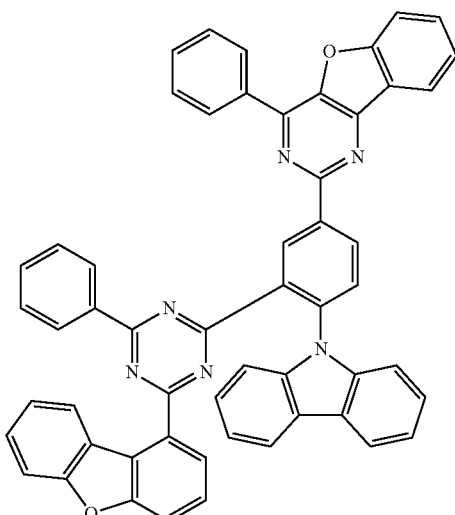
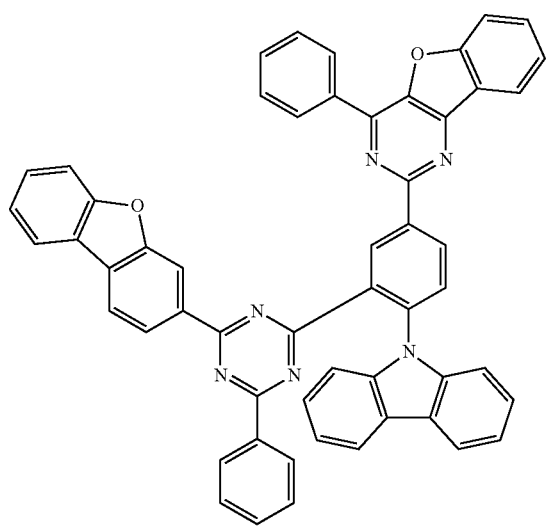
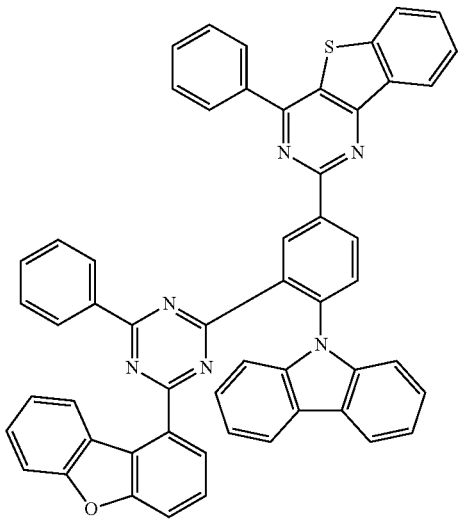

99
-continued
100
-continued
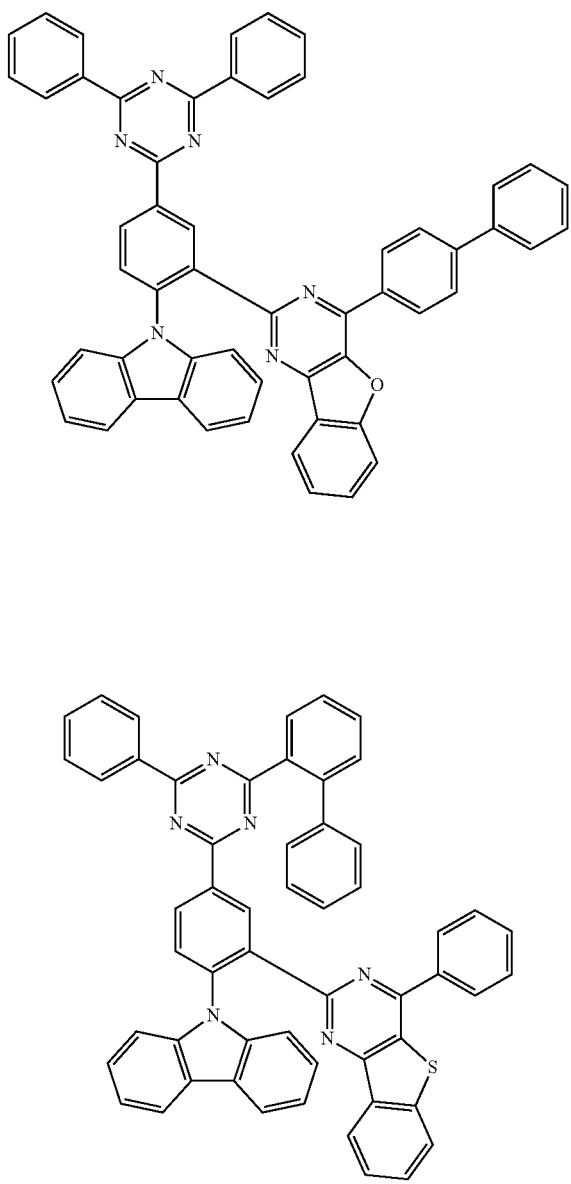
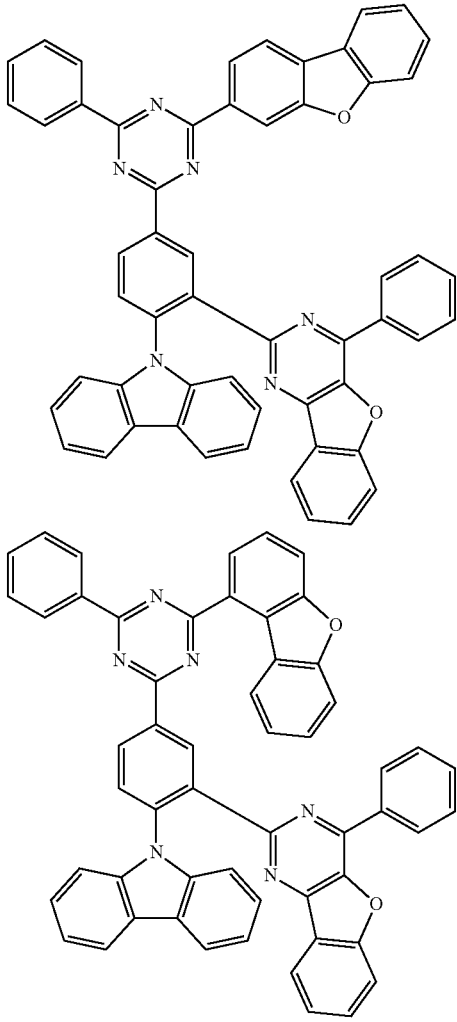
9. An organic light emitting device comprising a first electrode; a second electrode provided to face the first electrode; and one or more organic material layers provided between the first electrode and the second electrode, wherein at least one layer of the organic material layers includes the compound according to claim 1.
* * * * *